US009353401B2

(12) United States Patent
Walia

(10) Patent No.: US 9,353,401 B2
(45) Date of Patent: May 31, 2016

(54) MULTIPLEX ASSAYS WITH MULTIPLE LUCIFERASES REPORTERS AND USES THEREOF

(75) Inventor: Rampyari Walia, Alpine, CA (US)

(73) Assignee: Targeting Systems, El Cajon, CA (US)

(*) Notice: Subject to any disclaimer, the term of this patent is extended or adjusted under 35 U.S.C. 154(b) by 43 days.

(21) Appl. No.: 13/393,170

(22) PCT Filed: Aug. 27, 2010

(86) PCT No.: PCT/US2010/047033
§ 371 (c)(1),
(2), (4) Date: Feb. 28, 2012

(87) PCT Pub. No.: WO2011/025980
PCT Pub. Date: Mar. 3, 2011

(65) Prior Publication Data
US 2012/0156705 A1 Jun. 21, 2012

Related U.S. Application Data

(60) Provisional application No. 61/238,146, filed on Aug. 29, 2009.

(51) Int. Cl.
*C12Q 1/66* (2006.01)
*C12N 9/02* (2006.01)

(52) U.S. Cl.
CPC ............... *C12Q 1/66* (2013.01); *C12N 9/0069* (2013.01)

(58) Field of Classification Search
USPC .......................................................... 435/8
See application file for complete search history.

(56) References Cited

U.S. PATENT DOCUMENTS

| 5,604,123 | A | * | 2/1997 | Kazami et al. | 435/189 |
|---|---|---|---|---|---|
| 6,495,355 | B1 | * | 12/2002 | Contag et al. | 435/189 |
| 7,723,502 | B2 | * | 5/2010 | Coleman et al. | 536/23.1 |
| 8,367,357 | B2 | * | 2/2013 | Ohmiya et al. | 435/8 |
| 2005/0037355 | A1 | * | 2/2005 | Day et al. | 435/6 |
| 2005/0112551 | A1 | * | 5/2005 | Blair et al. | 435/5 |
| 2005/0153310 | A1 | * | 7/2005 | Fan et al. | 435/6 |
| 2008/0193956 | A1 | * | 8/2008 | Kricka et al. | 435/8 |
| 2008/0274485 | A1 | | 11/2008 | Walia | |
| 2009/0081715 | A1 | * | 3/2009 | Burns-Guydish et al. | 435/8 |
| 2009/0136998 | A1 | * | 5/2009 | Gambhir et al. | 435/69.1 |
| 2010/0055693 | A1 | * | 3/2010 | Leu et al. | 435/6 |
| 2010/0092967 | A1 | * | 4/2010 | Leu et al. | 435/6 |

OTHER PUBLICATIONS

Bennett et al., "Development of a dual-luciferase fusion gene as a sensitive marker for site-directed DNA repair strategies", The Journal of Gene Medicine, vol. 5, pp. 723-732, 2003.*
GenBank Accession No. AAB86460.1, published Nov. 17, 1997.*

(Continued)

*Primary Examiner* — Robert Mondesi
*Assistant Examiner* — Richard Ekstrom
(74) *Attorney, Agent, or Firm* — Pepper Hamilton LLP

(57) ABSTRACT

The present invention encompasses modified luciferases, methods for making modified luciferases, and assays utilizing modified luciferases. Modified luciferases of the invention show increased activity over wildtype luciferases and also show increased stability of signal. The present invention also encompasses multiplex assays utilizing multiple luciferases reporters with different emission spectra and different substrates for simultaneous luciferase measurements.

1 Claim, 42 Drawing Sheets

(56) References Cited

OTHER PUBLICATIONS

Branchini, B.R., et al., "Thermostable red and green light-producing firefly luciferase mutants for bioluminescent reporter applications," *Anal. Biochem.* Feb. 15, 2007;361(2):253-262.

Kitayama et al., "An in vivo dual-reporter system of cyanobacteria using two ralroad-worm luciferases with different color emission," *Plant Cell Physiology*, 2004, vol. 45, No. 1, pp. 109-113.

Michelini et al., "Spectral-Resolved Gene Technology for Multiplexed Bioluminexcence and High-Content Screening," *Analytical Chemistry*, 2008, vol. 80, No. 1, pp. 260-267.

Stern et al., "Improving mammalian cell factories: The selection of signal peptide has a major impact on recombinant protein synthesis and secretion in mammalian cells," *Trends in Cell and Molecular Biology* (online), 2007, http://unitargeting.com/Resources/Trends07.pdf, p. 6, col. 2, para 5 to p. 7, col. 1, para 1; p. 7, col. 1, para 4; p. 8, col. 1, para 1; p. 9, col. 1, para 3; Table 1.

Wu, C., et al., "Dual-reporter assay using two secreted luciferase genes," *Biotechniques.* Mar. 2007;42(3):290-292.

Relevant Portion of International Search Report, PCT/US2010/047033, mailed Nov. 18, 2010.

\* cited by examiner

FIG. 2A. Sample volume 20 μl
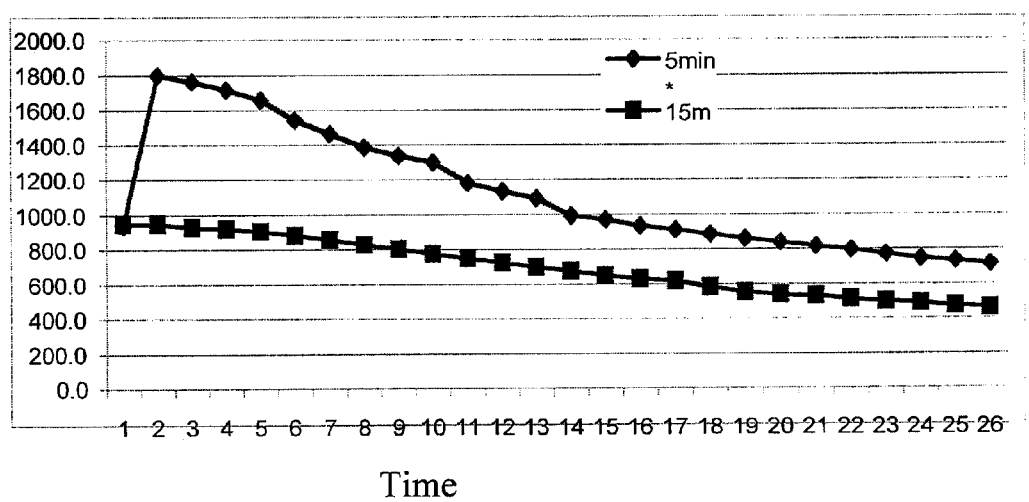
Time
FIG. 2B. Sample volume 5 μl
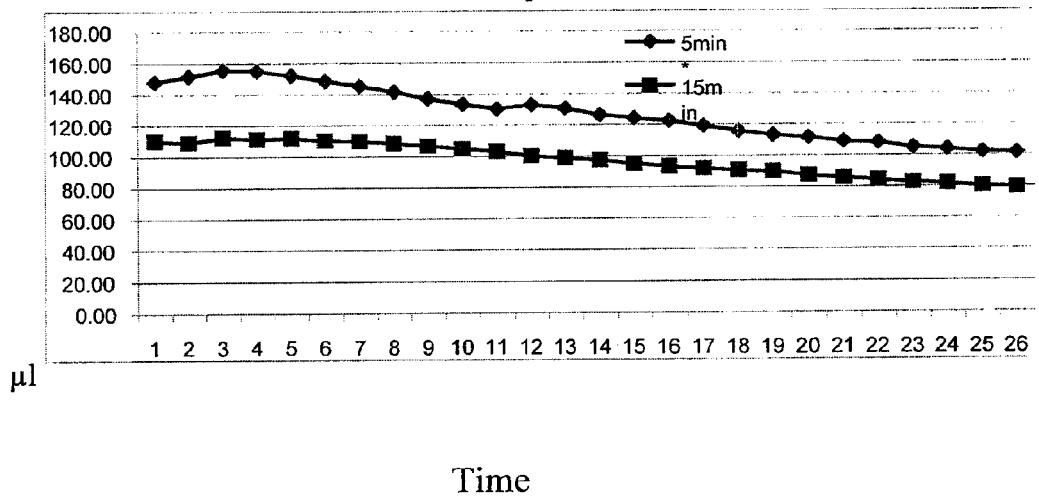
Time

FIG. 3A pCMV Green Renilla Luciferase plasmid Sequence (SEQ ID NO: 1):

```
   1 gacggatcgg gagatctccc gatccoctat ggtcgactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggac tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc ctacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aaatgtcgta acaactccgc cccattgacg caaatgggcg
 781 gtaggcgtgt acggtgggag gtctatataa gcagagctct ctggctaact agagaaccca
 841 ctgcttactg gcttatcgaa attaatacga ctcactatag ggagacccaa gcttggtacc
 901 gagctcggat ccatgttgtt gaaagttgtg tttgctattg gatgtatcgt agtgcaggct
 961 atggcctcaa aagtgtacga tccggagcag cggaagagga tgatcacggg gccccaatgg
1021 tgggcacgat gcaagcagat gaatgtgttg gacagtttca ttaactacta cgacagcgag
1081 aaacacgcgg agaacgcagt gatattcctg cacggcaatg caaccagtag ctatctgtgg
1141 agacacgtgg tgcctcatat tgagccggtc gctagatgca ttattcccga tcttattgga
1201 atggggaaat ccggaaagag tggaaatgga tcatataggc tcctcgatca ttataaatat
1261 ctgactgctt ggtttgaatt gctcaatctg cccaagaaaa tcatctttgt aggacatgat
1321 tggggctccg cccttgcttt tcattatgcc tatgaacacc aggatcggat caaggctatt
1381 gttcacatgg agagcgtggt ggatgtgatt gaatcatgga tgggttggcc ggatatagaa
1441 gaagagctgg cgctgattaa atctgaggag ggcgagaaga tggtactcga aaataacttc
1501 tttgtcgaga cggtactgcc cagtaagatc atgcgcaaac tggagcctga agagtttgcg
1561 gcttacctgg aaccctttca aggagaaggga gaggtgagga gaccgaccct gtcatggcct
1621 cgggaaattc cgctggtcaa aggagggaag ccagacgtcg tcgccattgt ccggaattac
1681 aacgcttacc tccgcgctag tgacgacctg cctaaactct tcatcgaatc agatcctggt
1741 ttctttagta acgccatcgt cgagggcgcc aagaagtttc caaacaccga atttgttaaa
1801 gtcaaaggac ttcacttcct ccaggaggat gcgcccgatg aaatgggaaa gtatatcaaa
1861 tccttcgtgg agagggtctt gaagaatgag cagaggtcca tctagtctag aaataattct
1921 tactgtcatg ccaagtaaga tgcttttctg tgctgcaata gcaggcatgc tggggatgcg
1981 gtgggctcta tggcttctga gcggaaaga accagctggg gctctagggg gtatccccac
2041 gcgccctgta gcggcgcatt aagcgcggcg ggtgtggtgg ttacgcgcag cgtgaccgct
2101 acacttgcca gcgccctagc gcccgctcct ttcgctttct tcccttcctt tctcgccacg
2161 ttcgccggct ttccccgtca gctctaaat cggggcatcc ctttagggtt ccgatttagt
2221 gctttacggc acctcgaccc caaaaaactt gattagggtg atggttcacg tagtgggcca
2281 tcgccctgat agacggtttt tcgccctttg acgttggagt ccacgttctt taatagtgga
2341 ctcttgttcc aaactggaac aacactcaac cctatctcgg tctattcttt tgatttataa
2401 gggattttgg ggatttcggc ctattggtta aaaaatgagc tgatttaaca aaaatttaac
2461 gcgaattaat tctgtggaat gtgtgtcagt tagggtgtgg aaagtcccca ggctccccag
2521 gcaggcagaa gtatgcaaag catgcatctc aattagtcag caaccaggtg tggaaagtcc
2581 ccaggctccc cagcaggcag aagtatgcaa agcatgcatc tcaattagtc agcaaccata
2641 gtcccgcccc taactccgcc catcccgccc ctaactccgc ccagttccgc ccattctccg
2701 ccccatggct gactaatttt ttttatttat gcagaggccg aggccgcctc tgcctctgag
2761 ctattccaga agtagtgagg aggcttttt ggaggcctag gcttttgcaa aaagctcccg
2821 ggagcttgta tatccatttt cggatctgat caagagacag gatgaggatc gtttcgcatg
2881 attgaacaag atggattgca cgcaggttct ccggccgctt gggtggagag gctattcggc
2941 tatgactggg cacaacagac aatcggctgc tctgatgccg ccgtgttccg gctgtcagcg
3001 caggggcgcc cggttctttt tgtcaagacc gacctgtccg gtgccctgaa tgaactgcag
3061 gacgaggcag cgcggctatc gtggctggcc acgacgggcg ttccttgcgc agctgtgctc
3121 gacgttgtca ctgaagcggg aagggactgg ctgctattgg gcgaagtgcc ggggcaggat
```

FIG. 3B

```
3181 ctcctgtcat ctcaccttgc tcctgccgag aaagtatcca tcatggctga tgcaatgcgg
3241 cggctgcata cgcttgatcc ggctacctgc ccattcgacc accaagcgaa acatcgcatc
3301 gagcgagcac gtactcggat ggaagccggt cttgtcgatc aggatgatct ggacgaagag
3361 catcaggggc tcgcgccagc cgaactgttc gccaggctca aggcgcgcat gcccgacggc
3421 gaggatctcg tcgtgaccca tggcgatgcc tgcttgccga atatcatggt ggaaaatggc
3481 cgcttttctg gattcatcga ctgtggccgg ctgggtgtgg cggaccgcta tcaggacata
3541 gcgttggcta cccgtgatat tgctgaagag cttggcggcg aatgggctga ccgcttcctc
3601 gtgctttacg gtatcgccgc tcccgattcg cagcgcatcg ccttctatcg ccttcttgac
3661 gagttcttct gagcgggact ctggggttcg aaatgaccga ccaagcgacg cccaacctgc
3721 catcacgaga tttcgattcc accgccgcct tctatgaaag gttgggcttc ggaatcgttt
3781 tccgggacgc cggctggatg atcctccagc gcggggatct catgctggag ttcttcgccc
3841 accccaactt gtttattgca gcttataatg gttacaaata aagcaatagc atcacaaatt
3901 tcacaaataa agcattttt tcactgcatt ctagttgtgg tttgtccaaa ctcatcaatg
3961 tatcttatca tgtctgtata ccgtcgacct ctagctagag cttggcgtaa tcatggtcat
4021 agctgtttcc tgtgtgaaat tgttatccgc tcacaattcc acacaacata cgagccggaa
4081 gcataaagtg taaagcctgg ggtgcctaat gagtgagcta actcacatta attgcgttgc
4141 gctcactgcc cgctttccag tcgggaaacc tgtcgtgcca gctgcattaa tgaatcggcc
4201 aacgcgcggg gagaggcggt ttgcgtattg ggcgctcttc cgcttcctcg ctcactgact
4261 cgctgcgctc ggtcgttcgg ctgcggcgag cggtatcagc tcactcaaag gcggtaatac
4321 ggttatccac agaatcaggg gataacgcag gaaagaacat gtgagcaaaa ggccagcaaa
4381 aggccaggaa ccgtaaaaag gccgcgttgc tggcgttttt ccataggctc cgcccccctg
4441 acgagcatca caaaaatcga cgctcaagtc agaggtggcg aaacccgaca ggactataaa
4501 gataccaggc gtttccccct ggaagctccc tcgtgcgctc tcctgttccg accctgccgc
4561 ttaccggata cctgtccgcc tttctccctt cgggaagcgt ggcgctttct caatgctcac
4621 gctgtaggta tctcagttcg gtgtaggtcg ttcgctccaa gctgggctgt gtgcacgaac
4681 cccccgttca gcccgaccgc tgcgccttat ccggtaacta tcgtcttgag tccaacccgg
4741 taagacacga cttatcgcca ctggcagcag ccactggtaa caggattagc agagcgaggt
4801 atgtaggcgg tgctacagag ttcttgaagt ggtggcctaa ctacggctac actagaagga
4861 cagtatttgg tatctgcgct ctgctgaagc cagttacctt cggaaaaaga gttggtagct
4921 cttgatccgg caaacaaacc accgctggta gcggtggttt ttttgtttgc aagcagcaga
4981 ttacgcgcag aaaaaaagga tctcaagaag atcctttgat cttttctacg gggtctgacg
5041 ctcagtggaa cgaaaactca cgttaaggga ttttggtcat gagattatca aaaaggatct
5101 tcacctagat ccttttaaat taaaaatgaa gttttaaatc aatctaaagt atatatgagt
5161 aaacttggtc tgacagttac caatgcttaa tcagtgaggc acctatctca gcgatctgtc
5221 tatttcgttc atccatagtt gcctgactcc ccgtcgtgta gataactacg atacgggagg
5281 gcttaccatc tggccccagt gctgcaatga taccgcgaga cccacgctca ccggctccag
5341 atttatcagc aataaaccag ccagccggaa gggccgagcg cagaagtggt cctgcaactt
5401 tatccgcctc catccagtct attaattgtt gccgggaagc tagagtaagt agttcgccag
5461 ttaatagttt gcgcaacgtt gttgccattg ctacaggcat cgtggtgtca cgctcgtcgt
5521 ttggtatggc ttcattcagc tccggttccc aacgatcaag gcgagttaca tgatccccca
5581 tgttgtgcaa aaaagcggtt agctccttcg gtcctccgat cgttgtcaga gtaagttgg
5641 ccgcagtgtt atcactcatg gttatggcag cactgcataa ttctcttact gtcatgccat
5701 ccgtaagatg cttttctgtg actggtgagt actcaaccaa gtcattctga gaatagtgta
5761 tgcggcgacc gagttgctct tgcccggcgt caatacggga taataccgcg ccacatagca
5821 gaactttaaa agtgctcatc attggaaaac gttcttcggg gcgaaaactc tcaaggatct
5881 taccgctgtt gagatccagt tcgatgtaac ccactcgtgc acccaactga tcttcagcat
5941 cttttacttt caccagcgtt tctgggtgag caaaaacagg aaggcaaaat gccgcaaaaa
6001 agggaataag ggcgacacgg aaatgttgaa tactcatact cttccttttt caatattatt
6061 gaagcattta tcagggttat tgtctcatga gcggatacat atttgaatgt atttagaaaa
6121 ataaacaaat aggggttccg cgcacatttc cccgaaaagt gccacctgac gtc
```

FIG. 4A
Modified red firefly luciferase with secretory signal (SEQ ID NO: 2)

```
   1 gacggatcgg gagatctccc gatcccctat ggtcgactct cagtacaatc tgctctgatg
  61 ccgcatagtt aagccagtat ctgctccctg cttgtgtgtt ggaggtcgct gagtagtgcg
 121 cgagcaaaat ttaagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggac tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc ctacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aaatgtcgta acaactccgc cccattgacg caaatgggcg
 781 gtaggcgtgt acggtgggag gtctatataa gcagagctct ctggctaact agagaaccca
 841 ctgcttactg gcttatcgaa attaatacga ctcactatag ggagacccaa gcttggtacc
 901 gagctcggat cc atggccttcctgtggctgctgtcctgctgggccctgctgggcaccaccttcggc
 961 tacccgatcg aggagggctc tgccggcatc caattgcaca agtacatgca acaatacgcc
1021 aagctcggcg ccatcgcctt cagtaacgcc ctgacaggcg tcgacatcag ctaccagcag
1081 tacttcgaca tcacgtgcag actcgccgag gctatgaaga actacggcat gaagccagaa
1141 ggacacatcg ctctctgtag cgagaactgc gaagagttct tcattcctgt tctggctggt
1201 ctttacatcg gagttacagt cgcgccaact aacgaaattt atacacttag agagctgaac
1261 cacagtctgg ggatagccca acctactatc gtattctcta gcaggaaggg cctgcccaaa
1321 gtgcttgagg tgcagaagac cgtgacttgc atcaaaacca ttgtcatcct ggacagtaag
1381 gtcaacttcg gcggttatga ctgcgtagag accttcatta agaaacacgt cgagctgggc
1441 tttcctgcca cctcatttgt gcccatcgac gtcaaagacc ggaagcacca cattgctctg
1501 cttatgaact cttccggttc cacagggctg cccaaaggag tagagatcac tcacgaggcc
1561 ctggtcacga gattctctca cgctaaggac cctatatacg gcaatcaggt ggccccaggt
1621 accgctatcc tgactgtcgt gcctttccac cacggcttcg gaatgttcac tactttgggc
1681 tactttgcct gcggttaccg gattgtcatg cttactaagt tcgacgagga gcttttcctg
1741 cgcacacttc aggattacaa gtgcactaca gtaatcctgg tgccgacact gttcgcaatt
1801 cttaataggt ctgagctcct tgataagttt gacctctcta acctgactga aatagccagc
1861 ggtggtgctc cacttgccaa ggagatcggc gaggctgttg caagaagatt caacctccca
1921 ggcgtccggc agggatatgg actcaccgag actaccagtg cctttatcat cactcctaag
1981 ggcgacgaca gccgggagc cagcggcaag gtcgtgcctc tgttcaaggt gaagattatt
2041 gacctcgata ccaagaaaac gttgggtgtc aacagacggg gagaaatctg cgtgaaagga
2101 ccatctctta tgttgggata cacgaacaat cctgaagcca ccagagaaac tattgacgag
2161 gaaggctggc tgcacacggg tgacatcggg tactacgacg aggatgagca cttctttata
2221 gtcgaccgcc tgaaatctct cattaagtat aaaggatacc aagtgccacc agctgaactg
2281 gagtctgtgc tcctgcaaca ccctaacatt agagatgctg gtgtggccgg ggttcccgac
2341 agcgaggcag gcgagctgcc tggagccgtc gttgtgatgg aaaagggaaa gacaatgact
2401 gagaaagaaa tcgtagacta tgtaaactcc caggtggtca accacaagcg gctgaggggc
2461 ggcgtgcggt tcgtagatga agtccccaag gggctcacag gaaagatcga cgcgaaagtt
2521 atcagggaga tactcaagaa acctcaagca ggtgggtagt ctagatctag aaataattct
2581 tactgtcatg ccaagtaaga tgcttttctg tgctgcaata gcaggcatgc tggggatgcg
2641 gtgggctcta tggcttctga ggcggaaaga accagctggg gctctagggg gtatccccac
2701 gcgccctgta gcggcgcatt aagcgcggcg ggtgtggtgg ttacgcgcag cgtgaccgct
2761 acacttgcca gcgccctagc gcccgctcct ttcgctttct tcccttcctt tctcgccacg
2821 ttcgccggct ttccccgtca agctctaaat cggggcatcc ctttagggtt ccgatttagt
2881 gctttacggc acctcgaccc caaaaaactt gattagggtg atggttcacg tagtgggcca
2941 tcgccctgat agacggtttt tcgcccttg acgttggagt ccacgttctt taatagtgga
3001 ctcttgttcc aaactggaac aacactcaac cctatctcgg tctattcttt tgatttataa
3061 gggattttgg ggatttcggc ctattggtta aaaaatgagc tgatttaaca aaaatttaac
3121 gcgaattaat tctgtggaat gtgtgtcagt tagggtgtgg aaagtcccca ggctccccag
3181 gcaggcagaa gtatgcaaag catgcatctc aattagtcag caaccaggtg tggaaagtcc
```

FIG. 4B

```
3241 ccaggctccc cagcaggcag aagtatgcaa agcatgcatc tcaattagtc agcaaccata
3301 gtcccgcccc taactccgcc catcccgccc ctaactccgc ccagttccgc ccattctccg
3361 ccccatggct gactaatttt ttttatttat gcagaggccg aggccgcctc tgcctctgag
3421 ctattccaga agtagtgagg aggcttttt ggaggcctag gcttttgcaa aaagctcccg
3481 ggagcttgta tatccatttt cggatctgat caagagacag gatgaggatc gtttcgcatg
3541 attgaacaag atggattgca cgcaggttct ccggccgctt gggtggagag gctattcggc
3601 tatgactggg cacaacagac aatcggctgc tctgatgccg ccgtgttccg gctgtcagcg
3661 caggggcgcc cggttctttt tgtcaagacc gacctgtccg gtgccctgaa tgaactgcag
3721 gacgaggcag cgcggctatc gtggctggcc acgacgggcg ttccttgcgc agctgtgctc
3781 gacgttgtca ctgaagcggg aagggactgg ctgctattgg gcgaagtgcc ggggcaggat
3841 ctcctgtcat ctcaccttgc tcctgccgag aaagtatcca tcatggctga tgcaatgcgg
3901 cggctgcata cgcttgatcc ggctacctgc ccattcgacc accaagcgaa acatcgcatc
3961 gagcgagcac gtactcggat ggaagccggt cttgtcgatc aggatgatct ggacgaagag
4021 catcaggggc tcgcgccagc cgaactgttc gccaggctca aggcgcgcat gcccgacggc
4081 gaggatctcg tcgtgaccca tggcgatgcc tgcttgccga atatcatggt ggaaaatggc
4141 cgcttttctg gattcatcga ctgtggccgg ctgggtgtgg cggaccgcta tcaggacata
4201 gcgttggcta cccgtgatat tgctgaagag cttggcggcg aatgggctga ccgcttcctc
4261 gtgctttacg gtatcgccgc tcccgattcg cagcgcatcg ccttctatcg ccttcttgac
4321 gagttcttct gagcgggact ctggggttcg aaatgaccga ccaagcgacg cccaacctgc
4381 catcacgaga tttcgattcc accgccgcct tctatgaaag gttgggcttc ggaatcgttt
4441 tccggacgc cggctgatg atcctccagc gcggggatct catgctggag ttcttcgccc
4501 accccaactt gtttattgca gcttataatg gttacaaata aagcaatagc atcacaaatt
4561 tcacaaataa agcatttttt tcactgcatt ctagttgtgg tttgtccaaa ctcatcaatg
4621 tatcttatca tgtctgtata ccgtcgacct ctagctagag cttggcgtaa tcatggtcat
4681 agctgtttcc tgtgtgaaat tgttatccgc tcacaattcc acacaacata cgagccggaa
4741 gcataaagtg taaagcctgg ggtgcctaat gagtgagcta actcacatta attgcgttgc
4801 gctcactgcc cgctttccag tcgggaaacc tgtcgtgcca gctgcattaa tgaatcggcc
4861 aacgcgcggg gagaggcggt ttgcgtattg gcgctcttc cgcttcctcg ctcactgact
4921 cgctgcgctc ggtcgttcgg ctgcggcgag cggtatcagc tcactcaaag gcggtaatac
4981 ggttatccac agaatcaggg gataacgcag gaaagaacat gtgagcaaaa ggccagcaaa
5041 aggccaggaa ccgtaaaaag gccgcgttgc tggcgttttt ccataggctc cgcccccctg
5101 acgagcatca caaaaatcga cgctcaagtc agaggtggcg aaacccgaca ggactataaa
5161 gataccaggc gtttccccct ggaagctccc tcgtgcgctc tcctgttccg accctgccgc
5221 ttaccggata cctgtccgcc tttctccctt cgggaagcgt ggcgctttct caatgctcac
5281 gctgtaggta tctcagttcg gtgtaggtcg ttcgctccaa gctgggctgt gtgcacgaac
5341 cccccgttca gcccgaccgc tgcgccttat ccggtaacta tcgtcttgag tccaacccgg
5401 taagacacga cttatcgcca ctggcagcag ccactggtaa caggattagc agagcgaggt
5461 atgtaggcgg tgctacagag ttcttgaagt ggtggcctaa ctacggctac actagaagga
5521 cagtatttgg tatctgcgct ctgctgaagc cagttacctt cggaaaaaga gttggtagct
5581 cttgatccgg caaacaaacc accgctggta gcggtggttt ttttgtttgc aagcagcaga
5641 ttacgcgcag aaaaaaagga tctcaagaag atcctttgat cttttctacg ggtctgacg
5701 ctcagtggaa cgaaaactca cgttaaggga ttttggtcat gagattatca aaaaggatct
5761 tcacctagat ccttttaaat taaaaatgaa gttttaaatc aatctaaagt atatatgagt
5821 aaacttggtc tgacagttac caatgcttaa tcagtgaggc acctatctca gcgatctgtc
5881 tatttcgttc atccatagtt gcctgactcc ccgtcgtgta gataactacg atacgggagg
5941 gcttaccatc tggccccagt gctgcaatga taccgcgaga cccacgctca ccggctccag
6001 atttatcagc aataaaccag ccagccggaa gggccgagcg cagaagtggt cctgcaactt
6061 tatccgcctc catccagtct attaattgtt gccgggaagc tagagtaagt agttcgccag
6121 ttaatagttt gcgcaacgtt gttgccattg ctacaggcat cgtggtgtca cgctcgtcgt
6181 ttggtatggc ttcattcagc tccggttccc aacgatcaag gcgagttaca tgatccccca
6241 tgttgtgcaa aaaagcggtt agctccttcg gtcctccgat cgttgtcaga agtaagttgg
6301 ccgcagtgtt atcactcatg gttatggcag cactgcataa ttctcttact gtcatgccat
6361 ccgtaagatg cttttctgtg actggtgagt actcaaccaa gtcattctga gaatagtgta
6421 tgcggcgacc gagttgctct tgcccggcgt caatacggga taataccgcg ccacatagca
6481 gaactttaaa agtgctcatc attggaaaac gttcttcggg gcgaaaactc tcaaggatct
6541 taccgctgtt gagatccagt tcgatgtaac ccactcgtgc acccaactga tcttcagcat
```

FIG. 4C

```
6601 cttttactttt caccagcgtt tctgggtgag caaaaacagg aaggcaaaat gccgcaaaaa
6661 agggaataag ggcgacacgg aaatgttgaa tactcatact cttccttttt caatattatt
6721 gaagcattta tcagggttat tgtctcatga gcggatacat atttgaatgt atttagaaaa
6781 ataaacaaat aggggttccg cgcacatttc cccgaaaagt gccacctgac gtc
```

Firefly Luciferase Assay reagent (FLAR-1)

Dual Assay for Cypridina-Renilla Luciferase (DLAR-5)

Panel A

Panel B

FIG. 27A

CMV Red Firefly Luciferase plasmid sequence:

ORIGIN
```
   1 gacggatcgg gagatctccc gatccctat ggtcgactct cagtacaatc tgctctgatg
  61 ccgcatagtt aagccagtat ctgctccctg cttgtgtgtt ggaggtcgct gagtagtgcg
 121 cgagcaaaat taagctaca acaaggcaag gcttgaccga caattgcatg aagaatctgc
 181 ttagggttag gcgttttgcg ctgcttcgcg atgtacgggc cagatatacg cgttgacatt
 241 gattattgac tagttattaa tagtaatcaa ttacggggtc attagttcat agcccatata
 301 tggagttccg cgttacataa cttacggtaa atggcccgcc tggctgaccg cccaacgacc
 361 cccgcccatt gacgtcaata atgacgtatg ttcccatagt aacgccaata gggactttcc
 421 attgacgtca atgggtggac tatttacggt aaactgccca cttggcagta catcaagtgt
 481 atcatatgcc aagtacgccc cctattgacg tcaatgacgg taaatggccc gcctggcatt
 541 atgcccagta catgacctta tgggactttc tacttggca gtacatctac gtattagtca
 601 tcgctattac catggtgatg cggttttggc agtacatcaa tgggcgtgga tagcggtttg
 661 actcacgggg atttccaagt ctccacccca ttgacgtcaa tgggagtttg ttttggcacc
 721 aaaatcaacg ggactttcca aatgtcgta acaactccgc cccattgacg caaatgggcg
 781 gtaggcgtgt acggtgggag gtctatataa gcagagctct ctggctaact agagaaccca
 841 ctgcttactg gcttatcgaa attaatacga ctcactatag ggagacccaa gcttggtacc
 901 gagctcggat ccagccacca tggaaacaga agagaagaa aacgttgtct acggcccact
 961 gccattctac ccgatcgagg agggctctgc cggcatccaa ttgcacaagt acatgcaaca
1021 atacgccaag ctcggcgcca tcgccttcag taacgccctg acaggcgtcg acatcagcta
1081 ccagcagtac ttcgacatca cgtgcagact cgccgaggct atgaagaact acggcatgaa
1141 gccagaagga cacatcgctc tctgtagcga gaactgcgaa gagttcttca ttcctgttct
1201 ggctggtctt tacatcggag ttacagtcgc gccaactaac gaaatttata cacttagaga
1261 gctgaaccac agtctgggga tagcccaacc tactatcgta ttctctagca ggaagggcct
1321 gcccaaagtg cttgaggtgc agaagaccgt gacttgcatc aaaaccattg tcatcctgga
1381 cagtaaggtc aacttcggcg gttatgactg cgtagagacc ttcattaaga aacacgtcga
1441 gctggcttt cctgccacct catttgtgcc catcgacgtc aaagaccgga agcaccacat
1501 tgctctgctt atgaactctt ccggttccac agggctgccc aaaggagtag agatcactca
1561 cgaggccctg gtcacgagat tctctcacgc taaggaccct atatacggca atcaggtggc
1621 cccaggtacc gctatcctga ctgtcgtgcc tttccaccac ggcttcggaa tgttcactac
1681 tttgggctac tttgcctgcg gttaccggat tgtcatgctt actaagttcg acgaggagct
1741 ttcctgcgc acacttcagg attacaagtg cactacagta atcctggtgc cgacactgtt
1801 cgcaattctt aataggtctg agctccttga taagtttgac ctctctaacc tgactgaaat
1861 agccagcggt ggtgctccac ttgccaagga gatcggcgag gctgttgcaa gaagattcaa
1921 cctcccaggc gtccggcagg gatatggact caccgagact accagtgcct tatcatcac
1981 tcctaagggc gacgacaagc cgggagccag cggcaaggtc gtgcctctgt tcaaggtgaa
2041 gattattgac ctcgatacca agaaaacgtt gggtgtcaac agacggggag aaatctgcgt
2101 gaaaggacca tctcttatgt tgggatacac gaacaatcct gaagccacca gagaaactat
2161 tgacgaggaa ggctggctgc acacgggtga catcgggtac tacgacgagg atgagcactt
2221 ctttatagtc gaccgcctga aatctctcat taagtataaa ggataccaag tgccaccagc
2281 tgaactggag tctgtgctcc tgcaacaccc taacattaga gatgctggtg tggccggggt
2341 tcccgacagc gaggcaggcg agctgcctgg agccgtcgtt gtgatggaaa agggaaagac
2401 aatgactgag aaagaaatcg tagactatgt aaactcccag gtggtcaacc acaagcggct
2461 gaggggcggc gtgcggttcg tagatgaagt ccccaagggg ctcacaggaa agatcgacgc
2521 gaaagttatc agggagatac tcaagaaacc tcaagcaggt gggtagtcta gaaataattc
2581 ttactgtcat gccaagtaag atgcttttct gtgctgcaat gcaggcatg ctggggatgc
2641 ggtgggctct atggcttctg aggcggaaag aaccagctgg ggctctaggg ggtatcccca
2701 cgcgccctgt agcggcgcat taagcgcggc gggtgtggtg gttacgcgca gcgtgaccgc
2761 tacacttgcc agcgccctag cgcccgctcc tttcgctttc ttcccttcct ttctcgccac
2821 gttcgccggc tttccccgtc aagctctaaa tcggggcatc cctttagggt tccgatttag
2881 tgctttacgg cacctcgacc ccaaaaaact tgattagggt gatggttcac gtagtgggcc
2941 atcgccctga tagacggttt ttcgcccttt gacgttggag tccacgttct ttaatagtgg
3001 actcttgttc caaactggaa caacactcaa ccctatctcg gtctattctt ttgatttata
3061 agggattttg gggatttcgg cctattggtt aaaaaatgag ctgatttaac aaaaatttaa
```

FIG. 27B

```
3121 cgcgaattaa ttctgtggaa tgtgtgtcag ttagggtgtg gaaagtcccc aggctcccca
3181 ggcaggcaga agtatgcaaa gcatgcatct caattagtca gcaaccaggt gtggaaagtc
3241 cccaggctcc ccagcaggca gaagtatgca aagcatgcat ctcaattagt cagcaaccat
3301 agtcccgccc ctaactccgc ccatcccgcc cctaactccg cccagttccg cccattctcc
3361 gccccatggc tgactaattt tttttattta tgcagaggcc gaggccgcct ctgcctctga
3421 gctattccag aagtagtgag gaggcttttt tggaggccta ggcttttgca aaaagctccc
3481 gggagcttgt atatccattt tcggatctga tcaagagaca ggatgaggat cgtttcgcat
3541 gattgaacaa gatggattgc acgcaggttc tccggccgct tgggtggaga ggctattcgg
3601 ctatgactgg gcacaacaga caatcggctg ctctgatgcc gccgtgttcc ggctgtcagc
3661 gcaggggcgc ccggttcttt ttgtcaagac cgacctgtcc ggtgccctga tgaactgca
3721 ggacgaggca gcgcggctat cgtggctggc cacgacgggc gttccttgcg cagctgtgct
3781 cgacgttgtc actgaagcgg gaagggactg gctgctattg ggcgaagtgc cggggcagga
3841 tctcctgtca tctcaccttg ctcctgccga gaaagtatcc atcatggctg atgcaatgcg
3901 gcggctgcat acgcttgatc cggctacctg cccattcgac caccaagcga acatcgcat
3961 cgagcgagca cgtactcgga tggaagccgg tcttgtcgat caggatgatc tggacgaaga
4021 gcatcagggg ctcgcgccag ccgaactgtt cgccaggctc aaggcgcgca tgcccgacgg
4081 cgaggatctc gtcgtgaccc atggcgatgc ctgcttgccg aatatcatgg tggaaaatgg
4141 ccgcttttct ggattcatcg actgtggccg gctgggtgtg gcggaccgct atcaggacat
4201 agcgttggct acccgtgata ttgctgaaga gcttggcggc gaatgggctg accgcttcct
4261 cgtgctttac ggtatcgccg ctcccgattc gcagcgcatc gccttctatc gccttcttga
4321 cgagttcttc tgagcgggac tctggggttc gaaatgaccg accaagcgac gcccaacctg
4381 ccatcacgag atttcgattc caccgccgcc ttctatgaaa ggttgggctt cggaatcgtt
4441 ttccgggacg ccggctggat gatcctccag cgcggggatc tcatgctgga gttcttcgcc
4501 caccccaact tgtttattgc agcttataat ggttacaaat aaagcaatag catcacaaat
4561 ttcacaaata aagcattttt tcactgcat tctagttgtg gtttgtccaa actcatcaat
4621 gtatcttatc atgtctgtat accgtcgacc tctagctaga gcttggcgta atcatggtca
4681 tagctgtttc ctgtgtgaaa ttgttatccg ctcacaattc cacacaacat acgagccgga
4741 agcataaagt gtaaagcctg gggtgcctaa tgagtgagct aactcacatt aattgcgttg
4801 cgctcactgc ccgctttcca gtcgggaaac ctgtcgtgcc agctgcatta atgaatcggc
4861 caacgcgcgg ggagaggcgg tttgcgtatt gggcgctctt ccgcttcctc gctcactgac
4921 tcgctgcgct cggtcgttcg gctgcggcga gcggtatcag ctcactcaaa ggcggtaata
4981 cggttatcca cagaatcagg ggataacgca ggaaagaaca tgtgagcaaa aggccagcaa
5041 aaggccagga accgtaaaaa ggccgcgttg ctggcgtttt tccataggct ccgcccccct
5101 gacgagcatc acaaaaatcg acgctcaagt cagaggtggc gaaacccgac aggactataa
5161 agataccagg cgtttccccc tggaagctcc ctcgtgcgct ctcctgttcc gaccctgccg
5221 cttaccggat acctgtccgc ctttctccct tcgggaagcg tggcgctttc tcaatgctca
5281 cgctgtaggt atctcagttc ggtgtaggtc gttcgctcca agctgggctg tgtgcacgaa
5341 ccccccgttc agcccgaccg ctgcgcctta tccggtaact atcgtcttga gtccaacccg
5401 gtaagacacg acttatcgcc actggcagca gccactggta acaggattag cagagcgagg
5461 tatgtaggcg gtgctacaga gttcttgaag tggtggccta actacggcta cactagaagg
5521 acagtatttg gtatctgcgc tctgctgaag ccagttacct tcggaaaaag agttggtagc
5581 tcttgatccg gcaaacaaac caccgctggt agcggtggtt tttttgtttg caagcagcag
5641 attacgcgca gaaaaaaagg atctcaagaa gatcctttga tcttttctac ggggtctgac
5701 gctcagtgga acgaaaactc acgttaaggg attttggtca tgagattatc aaaaaggatc
5761 ttcacctaga tccttttaaa ttaaaaatga agttttaaat caatctaaag tatatatgag
5821 taaacttggt ctgacagtta ccaatgctta atcagtgagg cacctatctc agcgatctgt
5881 ctatttcgtt catccatagt tgcctgactc cccgtcgtgt agataactac gatacgggag
5941 ggcttaccat ctggccccag tgctgcaatg ataccgcgag acccacgctc accggctcca
6001 gatttatcag caataaacca gccagccgga agggccgagc gcagaagtgg tcctgcaact
6061 ttatccgcct ccatccagtc tattaattgt tgccgggaag ctagagtaag tagttcgcca
6121 gttaatagtt tgcgcaacgt tgttgccatt gctacaggca tcgtggtgtc acgctcgtcg
6181 tttggtatgg cttcattcag ctccggttcc caacgatcaa ggcgagttac atgatccccc
6241 atgttgtgca aaaaagcggt tagctccttc ggtcctccga tcgttgtcag aagtaagttg
6301 gccgcagtgt tatcactcat ggttatggca gcactgcata attctcttac tgtcatgcca
```

FIG. 27C

```
6361 tccgtaagat gcttttctgt gactggtgag tactcaacca agtcattctg agaatagtgt
6421 atgcggcgac cgagttgctc ttgcccggcg tcaatacggg ataataccgc gccacatagc
6481 agaactttaa aagtgctcat cattggaaaa cgttcttcgg ggcgaaaact ctcaaggatc
6541 ttaccgctgt tgagatccag ttcgatgtaa cccactcgtg cacccaactg atcttcagca
6601 tcttttactt tcaccagcgt ttctgggtga gcaaaaacag gaaggcaaaa tgccgcaaaa
6661 aagggaataa gggcgacacg gaaatgttga atactcatac tcttcctttt tcaatattat
6721 tgaagcattt atcagggtta ttgtctcatg agcggataca tatttgaatg tatttagaaa
6781 aataaacaaa taggggttcc gcgcacattt ccccgaaaag tgccacctga cgtc
```

FIG. 30A

A mammalian expression vector expressing Red emitting firefly luciferase (human codon optimized signal) under control of the CMV promoter) (SEQ ID NO: 3)

Size: 6827 bases

```
   1  gacggatcgg gagatctccc gatccctat ggtcgactct cagtacaatc tgctctgatg
  61  ccgcatagtt aagccagtat ctgctccctg cttgtgtgtt ggaggtcgct gagtagtgcg
 121  cgagcaaaat ttaagctaca acaaggcaag gcttgaccga caattgcatg aagaatctgc
 181  ttagggttag gcgttttgcg ctgcttcgcg atgtacgggc cagatatacg cgttgacatt
 241  gattattgac tagttattaa tagtaatcaa ttacggggtc attagttcat agcccatata
 301  tggagttccg cgttacataa cttacggtaa atggcccgcc tggctgaccg cccaacgacc
 361  cccgcccatt gacgtcaata atgacgtatg ttcccatagt aacgccaata gggactttcc
 421  attgacgtca atgggtggac tatttacggt aaactgccca cttggcagta catcaagtgt
 481  atcatatgcc aagtacgccc cctattgacg tcaatgacgg taaatggccc gcctggcatt
 541  atgcccagta catgacctta tgggactttc ctacttggca gtacatctac gtattagtca
 601  tcgctattac catggtgatg cggttttggc agtacatcaa tgggcgtgga tagcggtttg
 661  actcacgggg atttccaagt ctccacccca ttgacgtcaa tgggagtttg ttttggcacc
 721  aaaatcaacg ggactttcca aatgtcgta acaactccgc cccattgacg caaatgggcg
 781  gtaggcgtgt acggtgggag gtctatataa gcagagctct ctggctaact agagaaccca
 841  ctgcttactg gcttatcgaa attaatacga ctcactatag ggagacccaa gcttggtacc
 901  gagctcggat ccatggaaac agaaagagaa gaaaacgttg tctacggccc actgccattc
 961  tacccgatcg aggagggctc tgccggcatc caattgcaca agtacatgca acaatacgcc
1021  aagctcggcg ccatcgcctt cagtaacgcc ctgacaggcg tcgacatcag ctaccagcag
1081  tacttcgaca tcacgtgcag actcgccgag gctatgaaga actacggcat gaagccagaa
1141  ggacacatcg ctctctgtag cgagaactgc gaagagttct tcattcctgt tctggctggt
1201  ctttacatcg gagttacagt cgcgccaact aacgaaaatt atacacttag agagctgaac
1261  cacagtctgg ggatagccca acctactatc gtattctcta gcaggaaggg cctgcccaaa
1321  gtgcttgagg tgcagaagac cgtgacttgc atcaaaacca ttgtcatcct ggacagtaag
1381  gtcaacttcg gcggttatga ctgcgtagag accttcatta agaaacacgt cgagctgggc
1441  ttcctgcca cctcatttgt gccatcgac gtcaaagacc ggaagcacca cattgctctg
1501  cttatgaact cttccggttc cacagggctg cccaaaggag tagagatcac tcacgaggcc
1561  ctggtcacga gattctctca cgctaaggac cctatatacg gcaatcaggt ggccccaggt
1621  accgctatcc tgactgtcgt gcctttccac cacggcttcg gaatgttcac tactttgggc
1681  tactttgcct gcggttaccg gattgtcatg cttactaagt tcgacgagga gcttttcctg
1741  cgcacacttc aggattacaa gtgcactaca gtaatcctgg tgccgacact gttcgcaatt
1801  cttaataggt ctgagctcct tgataagttt gacctctcta acctgactga aatagccagc
1861  ggtggtgctc cacttgccaa ggagatcggc gaggctgttg caagaagatt caacctccca
1921  ggcgtccggc agggatatgg actcaccgag actaccagtg cctttatcat cactcctaag
1981  ggcgacgaca agccgggagc cagcggcaag gtcgtgcctc tgttcaaggt gaagattatt
2041  gacctctgata ccaagaaaac gttgggtgtc aacagacggg gagaaatctg cgtgaaagga
2101  ccatctctta tgttgggata cacgaacaat cctgaagcca ccagagaaac tattgacgag
2161  gaaggctggc tgcacacggg tgacatcggg tactacgacg aggatgagca cttctttata
2221  gtcgaccgcc tgaaatctct cattaagtat aaaggatacc aagtgccacc agctgaactg
2281  gagtctgtgc tcctgcaaca ccctaacatt agagatgctg gtgtggccgg ggttcccgac
2341  agcgaggcag gcgagctgcc tggagccgtc gttgtgatgg aaaagggaaa gacaatgact
2401  gagaaagaaa tcgtagacta tgtaaactcc caggtggtca accacaagcg gctgagggc
2461  ggcgtgcggt tcgtagatga agtccccaag gggctcacag gaaagatcga cgcgaaagtt
2521  atcagggaga tactcaagaa acctcaagca ggtgggtagt ctagatctag aaataattct
2581  tactgtcatg ccaagtaaga tgcttttctg tgctgcaata gcaggcatgc tggggatgcg
2641  gtgggctcta tggcttctga ggcggaaaga accagctggg gctctagggg gtatccccac
2701  gcgccctgta gcggcgcatt aagcgcggcg ggtgtggtgg ttacgcgcag cgtgaccgct
2761  acacttgcca gcgccctagc gcccgctcct ttcgctttct tcccttcctt tctcgccacg
2821  ttcgccggct ttccccgtca gctctaaat cggggcatcc ctttagggtt ccgatttagt
2881  gctttacggc acctcgaccc caaaaaactt gattagggtg atggttcacg tagtgggcca
2941  tcgccctgat agacggtttt tcgccctttg acgttggagt ccacgttctt taatagtgga
3001  ctcttgttcc aaactggaac aacactcaac cctatctcgg tctattcttt tgatttataa
3061  gggattttgg ggatttcggc ctattggtta aaaaatgagc tgatttaaca aaaatttaac
3121  gcgaattaat tctgtggaat gtgtgtcagt tagggtgtgg aaagtcccca ggctcccag
3181  gcaggcagaa gtatgcaaag catgcatctc aattagtcag caaccaggtg tggaaagtcc
3241  ccaggctccc cagcaggcag aagtatgcaa agcatgcatc tcaattagtc agcaaccata
3301  gtcccgcccc taactccgcc catcccgccc ctaactccgc ccagttccgc ccattctccg
```

FIG. 30B

```
3361  ccccatggct gactaatttt ttttatttat gcagaggccg aggccgcctc tgcctctgag
3421  ctattccaga agtagtgagg aggctttttt ggaggcctag gcttttgcaa aaagctcccg
3481  ggagcttgta tatccatttt cggatctgat caagagacag gatgaggatc gtttcgcatg
3541  attgaacaag atggattgca cgcaggttct ccggccgctt gggtggagag gctattcggc
3601  tatgactggg cacaacagac aatcggctgc tctgatgccg ccgtgttccg gctgtcagcg
3661  caggggcgcc cggttctttt tgtcaagacc gacctgtccg gtgccctgaa tgaactgcag
3721  gacgaggcag cgcggctatc gtggctggcc acgacggggcg ttccttgcgc agctgtgctc
3781  gacgttgtca ctgaagcggg aagggactgg ctgctattgg gcgaagtgcc ggggcaggat
3841  ctcctgtcat ctcaccttgc tcctgccgag aaagtatcca tcatggctga tgcaatgcgg
3901  cggctgcata cgcttgatcc ggctacctgc ccattcgacc accaagcgaa acatcgcatc
3961  gagcgagcac gtactcggat ggaagccggt cttgtcgatc aggatgatct ggacgaagag
4021  catcaggggc tcgcgccagc cgaactgttc gccaggctca aggcgcgcat gcccgacggc
4081  gaggatctcg tcgtgaccca tggcgatgcc tgcttgccga atatcatggt ggaaaatggc
4141  cgcttttctg gattcatcga ctgtggccgg ctgggtgtgg cggaccgcta tcaggacata
4201  gcgttggcta cccgtgatat tgctgaagag cttggcggcg aatgggctga ccgcttcctc
4261  gtgctttacg gtatcgccgc tcccgattcg cagcgcatcg ccttctatcg ccttcttgac
4321  gagttcttct gagcgggact ctggggttcg aaatgaccga ccaagcgacg cccaacctgc
4381  catcacgaga tttcgattcc accgccgcct tctatgaaag gttgggcttc ggaatcgttt
4441  tccgggacgc cggctggatg atcctccagc gcggggatct catgctggag ttcttcgccc
4501  accccaactt gtttattgca gcttataatg gttacaaata aagcaatagc atcacaaatt
4561  tcacaaataa agcatttttt tcactgcatt ctagttgtgg tttgtccaaa ctcatcaatg
4621  tatcttatca tgtctgtata ccgtcgacct ctagctagag cttggcgtaa tcatggtcat
4681  agctgtttcc tgtgtgaaat tgttatccgc tcacaattcc acacaacata cgagccggaa
4741  gcataaagtg taaagcctgg ggtgcctaat gagtgagcta actcacatta attgcgttgc
4801  gctcactgcc cgctttccag tcgggaaacc tgtcgtgcca gctgcattaa tgaatcggcc
4861  aacgcgcggg gagaggcggt ttgcgtattg ggcgctcttc cgcttcctcg ctcactgact
4921  cgctgcgctc ggtcgttcgg ctgcggcgag cggtatcagc tcactcaaag gcggtaatac
4981  ggttatccac agaatcaggg gataacgcag gaaagaacat gtgagcaaaa ggccagcaaa
5041  aggccaggaa ccgtaaaaag gccgcgttgc tggcgttttt ccataggctc cgcccccctg
5101  acgagcatca caaaaatcga cgctcaagtc agaggtggcg aaacccgaca ggactataaa
5161  gataccaggc gtttccccct ggaagctccc tcgtgcgctc tcctgttccg accctgccgc
5221  ttaccggata cctgtccgcc tttctccctt cgggaagcgt ggcgctttct caatgctcac
5281  gctgtaggta tctcagttcg gtgtaggtcg ttcgctccaa gctgggctgt gtgcacgaac
5341  cccccgttca gcccgaccgc tgcgccttat ccggtaacta tcgtcttgag tccaacccgg
5401  taagacacga cttatcgcca ctggcagcag ccactggtaa caggattagc agagcgaggt
5461  atgtaggcgg tgctacagag ttcttgaagt ggtggcctaa ctacggctac actagaagga
5521  cagtatttgg tatctgcgct ctgctgaagc cagttacctt cggaaaaaga gttggtagct
5581  cttgatccgg caaacaaacc accgctggta gcggtggttt ttttgtttgc aagcagcaga
5641  ttacgcgcag aaaaaaagga tctcaagaag atcctttgat cttttctacg gggtctgacg
5701  ctcagtggaa cgaaaactca cgttaagggga ttttggtcat gagattatca aaaaggatct
5761  tcacctagat ccttttaaat taaaaatgaa gttttaaatc aatctaaagt atatatgagt
5821  aaacttggtc tgacagttac caatgcttaa tcagtgaggc acctatctca gcgatctgtc
5881  tatttcgttc atccatagtt gcctgactcc ccgtcgtgta gataactacq atacgggagg
5941  gcttaccatc tggccccagt gctgcaatga taccgcgaga cccacgctca ccggctccag
6001  atttatcagc aataaaccag ccagccggaa gggccgagcg cagaagtggt cctgcaactt
6061  tatccgcctc catccagtct attaattgtt gccgggaagc tagagtaagt agttcgccag
6121  ttaatagttt gcgcaacgtt gttgccattg ctacaggcat cgtggtgtca cgctcgtcgt
6181  ttggtatggc ttcattcagc tccggttccc aacgatcaag gcgagttaca tgatccccca
6241  tgttgtgcaa aaaagcggtt agctccttcg gtcctccgat cgttgtcaga agtaagttgg
6301  ccgcagtgtt atcactcatg gttatggcag cactgcataa ttctcttact gtcatgccat
6361  ccgtaagatg cttttctgtg actggtgagt actcaaccaa gtcattctga aatagtgta
6421  tgcggcgacc gagttgctct tgcccggcgt caatacggga taataccgcg ccacatagca
6481  gaactttaaa agtgctcatc attggaaaac gttcttcggg gcgaaaactc tcaaggatct
6541  taccgctgtt gagatccagt tcgatgtaac ccactcgtgc acccaactga tcttcagcat
6601  cttttacttt caccagcgtt tctgggtgag caaaaacagg aaggcaaaat gccgcaaaaa
6661  agggaataag ggcgacacgg aaatgttgaa tactcatact cttcctttt caatattat
6721  gaagcattta tcagggttat tgtctcatga gcggatacat atttgaatgt atttagaaaa
6781  ataaacaaat aggggttccg cgcacatttc cccgaaaagt gccacctgac gtc
```

FIG. 31A

Sequence and Features of pCMV GrFLUC Vector:
A mammalian expression vector expressing human codon optimized green firefly luciferase (Luciola Italica) under control of the CMV promoter (SEQ ID NO: 4)
Size: 6827 bases pCMV-GrFLuc (6827 bp)
CMV promoter bases: 209-863
Green emitting firefly luciferase gene: 907-2560
T7 promoter bases: 1827-1845
Polylinker bases: 1852-1870
SP6 promoter: 2576-2593
Synthetic polyadenylation site: 2560-2604
SV40 promoter bases: 3145-3480
SV40 origin of replication: bases: 3259-3344
Neomycin ORF : bases 3516- 4310
SV40 PolyA: bases 4365-4737
ColE1 origin: bases 3934-4607
Ampicillin ORF: bases 4752-5612

```
   1  gacggatcgg gagatctccc gatcccctat ggtcgactct cagtacaatc tgctctgatg
  61  ccgcatagtt aagccagtat ctgctccctg cttgtgtgtt ggaggtcgct gagtagtgcg
 121  cgagcaaaat ttaagctaca caaaggcaag gcttgaccga caattgcatg aagaatctgc
 181  ttagggttag gcgttttgcg ctgcttcgcg atgtacgggc cagatatacg cgttgacatt
 241  gattattgac tagttattaa tagtaatcaa ttacggggtc attagttcat agcccatata
 301  tggagttccg cgttacataa cttacggtaa atggcccgcc tggctgaccg cccaacgacc
 361  cccgcccatt gacgtcaata atgacgtatg ttcccatagt aacgccaata gggactttcc
 421  attgacgtca atgggtggac tatttacggt aaactgccca cttggcagta catcaagtgt
 481  atcatatgcc aagtacgccc cctattgacg tcaatgacgg taaatggccc gcctggcatt
 541  atgcccagta catgacctta tgggactttc ctacttggca gtacatctac gtattagtca
 601  tcgctattac catggtgatg cggttttggc agtacatcaa tgggcgtgga tagcggtttg
 661  actcacgggg atttccaagt ctccaccca ttgacgtcaa tgggagtttg ttttggcacc
 721  aaaatcaacg ggactttcca aatgtcgta acaactccgc cccattgacg caaatgggcg
 781  gtaggcgtgt acggtgggag gtctatataa gcagagctct ctggctaact agagaaccca
 841  ctgcttactg gcttatcgaa attaatacga ctcactatag ggagacccaa gcttggtacc
 901  gagctcggat ccatggaaac agaaagagaa gaaaacgttg tctacggccc actgccattc
 961  tacccgatcg aggagggctc tgccggcatc caattgcaca agtacatgca acaatacgcc
1021  aagctcggcg ccatcgcctt cagtaacgcc ctgacaggcg tcgacatcag ctaccagcag
1081  tacttcgaca tcacgtgcag actcgccgag gctatgaaga actacggcat gaagccagaa
1141  ggacacatcg ctctctgtag cgagaactgc gaagagttct tcattcctgt tctggctggt
1201  ctttacatcg gagttacagt cgccgcaact aacgaaattt atacacttag agagctgaac
1261  cacagtctgg ggatagccca acctactatc gtattctcta gcaggaaggg cctgcccaaa
1321  gtgcttgagg tgcagaagac cgtgacttgc atcaaaacca ttgtcatcct ggacagtaag
1381  gtcaacttcg gcggttatga ctgcgtagag accttcatta agaaacacgt cgagctgggc
1441  tttcctgcca cctcatttgt gcccatcgac gtcaaagacc ggaagcacca cattgctctg
1501  cttatgaact cttccggttc cacagggctg cccaaaggag tagagatcac tcacgaggcc
1561  ctggtcacga gattctctca cgctaaggac cctatatacg gcaatcaggt ggcccaggt
1621  accgctatcc tgactgtcat ccctttccac cacgccttcg gaatgagcac tactttgggc
1681  tactttgcct gcggttaccg gattgtcatg cttactaagt tcgacgagga gcttttcctg
1741  cgcacacttc aggattacaa gtgcactagc gtaatcctgg tgccgacact gttcgcaatt
1801  cttaataggt ctgagctcct tgataagttt gacctctcta acctgactga aatagccagc
1861  ggtggtgctc cacttgccaa ggagatcggc gaggctgttg caagaagatt caacctccca
1921  ggcgtccggc agggatatgg actcaccgag actaccagtg cctttatcat cactcctaag
1981  ggcgacgaca agccgggagc cagcggcaag gtcgtgcctc tgttcaaggt gaagattatt
2041  gacctcgata ccaagaaaac gttgggtgtc aacagacggg gagaaatctg cgtgaaagga
2101  ccatctctta tgttgggata cacgaacaat cctgaagcca ccagagaaac tattgacgag
2161  gaaggctggc tgcacacggg tgacatcggg tactacgacg aggatgagca cttctttata
2221  gtcgaccgcc tgaaatctct cattaagtat aaaggatacc aagtgccacc agctgaactg
2281  gagtctgtgc tcctgcaaca ccctaacatt agagatgctg gtgtggccgg ggttccccgac
2341  agcgaggcag gcgagctgcc tggagccgtc gttgtgatgg aaaagggaaa gacaatgact
2401  gagaaagaaa tcgtagacta tgtaaactcc caggtggtca accacaagcg gctgaggggc
2461  ggcgtgcggt tcgtagatga agtccccaag gggctcacag gaaagatcga cgcgaaagtt
```

FIG. 31B

```
2521  atcagggaga tactcaagaa acctcaagca ggtgggtagt ctagaaataa ttcttactgt
2581  catgccaagt aagatgcttt tctgtgctgc aatagcaggc atgctgggga tgcggtgggc
2641  tctatggctt ctgaggcgga aagaaccagc tggggctcta gggggtatcc ccacgcgccc
2701  tgtagcggcg cattaagcgc ggcgggtgtg gtggttacgc gcagcgtgac cgctacactt
2761  gccagcgccc tagcgcccgc tcctttcgct ttcttccctt cctttctcgc cacgttcgcc
2821  ggctttcccc gtcaagctct aaatcggggc atccctttag ggttccgatt tagtgcttta
2881  cggcacctcg accccaaaaa acttgattag ggtgatggtt cacgtagtgg gccatcgccc
2941  tgatagacgg ttttcgccc tttgacgttg gagtccacgt tctttaatag tggactcttg
3001  ttccaaactg gaacaacact caaccctatc tcggtctatt cttttgattt ataagggatt
3061  ttggggattt cggcctattg gttaaaaaat gagctgattt aacaaaaatt taacgcgaat
3121  taattctgtg gaatgtgtgt cagttagggt gtggaaagtc cccaggctcc ccaggcaggc
3181  agaagtatgc aaagcatgca tctcaattag tcagcaacca ggtgtggaaa gtcccaggc
3241  tccccagcag gcagaagtat gcaaagcatg catctcaatt agtcagcaac catagtcccg
3301  cccctaactc cgcccatccc gcccctaact ccgcccagtt ccgcccattc tccgccccat
3361  ggctgactaa tttttttat ttatgcagag gccgaggccg cctctgcctc tgagctattc
3421  cagaagtagt gaggaggctt ttttggaggc ctaggctttt gcaaaaagct cccgggagct
3481  tgtatatcca ttttcggatc tgatcaagag acaggatgag gatcgtttcg catgattgaa
3541  caagatggat tgcacgcagg ttctccggcc gcttgggtgg agaggctatt cggctatgac
3601  tgggcacaac agacaatcgg ctgctctgat gccgccgtgt tccggctgtc agcgcagggg
3661  cgcccggttc ttttgtcaa gaccgacctg tccggtgccc tgaatgaact gcaggacgag
3721  gcagcgcggc tatcgtggct ggccacgacg ggcgttcctt gcgcagctgt gctcgacgtt
3781  gtcactgaag cgggaaggga ctggctgcta ttgggcgaag tgccggggca ggatctcctg
3841  tcatctcacc ttgctcctgc cgagaaagta tccatcatgg ctgatgcaat gcggcggctg
3901  catacgcttg atccggctac ctgcccattc gaccaccaag cgaaacatcg catcgagcga
3961  gcacgtactc ggatggaagc cggtcttgtc gatcaggatg atctggacga agagcatcag
4021  gggctcgcgc cagccgaact gttcgccagg ctcaaggcgc gcatgcccga cggcgaggat
4081  ctcgtcgtga cccatggcga tgcctgcttg ccgaatatca tggtggaaaa tggccgcttt
4141  tctggattca tcgactgtgg ccggctgggt gtggcggacc gctatcagga catcgcgttg
4201  gctacccgtg atattgctga agagcttggc ggcgaatggg ctgaccgctt cctcgtgctt
4261  tacggtatcg ccgctcccga ttcgcagcgc atcgccttct atcgccttct tgacgagttc
4321  ttctgagcgg gactctgggg ttcgaaatga ccgaccaagc gacgcccaac ctgccatcac
4381  gagatttcga ttccaccgcc gccttctatg aaaggttggg cttcggaatc gttttccggg
4441  acgccggctg gatgatcctc cagcgcgggg atctcatgct ggagttcttc gcccacccca
4501  acttgtttat tgcagcttat aatggttaca aataaagcaa tagcatcaca aatttcacaa
4561  ataaagcatt ttttcactg cattctagtt gtggtttgtc caaactcatc aatgtatctt
4621  atcatgtctg tataccgtcg acctctagct agagcttggc gtaatcatgg tcatagctgt
4681  ttcctgtgtg aaattgttat ccgctcacaa ttccacacaa catacgagcc ggaagcataa
4741  agtgtaaagc ctggggtgcc taatgagtga gctaactcac attaattgcg ttgcgctcac
4801  tgcccgcttt ccagtcggga aacctgtcgt gccagctgca ttaatgaatc ggccaacgcg
4861  cggggagagg cggtttgcgt attgggcgct cttccgcttc ctcgctcact gactcgctgc
4921  gctcggtcgt tcggctgcgg cgagcggtat cagctcactc aaaggcggta atacggttat
4981  ccacagaatc aggggataac gcaggaaaga acatgtgagc aaaaggccag caaaaggcca
5041  ggaaccgtaa aaaggccgcg ttgctggcgt ttttccatag gctccgcccc cctgacgagc
5101  atcacaaaaa tcgacgctca agtcagaggt ggcgaaaccc gacaggacta taaagatacc
5161  aggcgtttcc ccctggaagc tccctcgtgc gctctcctgt tccgaccctg ccgcttaccg
5221  gatacctgtc cgcctttctc ccttcgggaa gcgtggcgct ttctcaatgc tcacgctgta
5281  ggtatctcag ttcggtgtag gtcgttcgct ccaagctggg ctgtgtgcac gaaccccccg
5341  ttcagcccga ccgctgcgcc ttatccggta actatcgtct tgagtccaac ccggtaagac
5401  acgacttatc gccactggca gcagccactg gtaacaggat tagcagagcg aggtatgtag
5461  gcggtgctac agagttcttg aagtggtggc ctaactacgg ctacactaga aggacagtat
5521  ttggtatctg cgctctgctg aagccagtta ccttcggaaa aagagttggt agctcttgat
5581  ccggcaaaca aaccaccgct ggtagcggtg gtttttttgt ttgcaagcag cagattacgc
5641  gcagaaaaaa aggatctcaa gaagatcctt tgatcttttc tacggggtct gacgctcagt
5701  ggaacgaaaa ctcacgttaa gggattttgg tcatgagatt atcaaaaagg atcttcacct
5761  agatcctttt aaattaaaaa tgaagtttta aatcaatcta agtatatat gagtaaactt
5821  ggtctgacag ttaccaatgc ttaatcagtg aggcacctat ctcagcgatc tgtctatttc
5881  gttcatccat agttgcctga ctccccgtcg tgtagataac tacgatacgg gagggcttac
5941  catctggccc cagtgctgca atgataccgc gagacccacg ctcaccggct ccagatttat
6001  cagcaataaa ccagccagcc ggaagggccg agcgcagaag tggtcctgca actttatccg
6061  cctccatcca gtctattaat tgttgccggg aagctagagt aagtagttcg ccagttaata
6121  gtttgcgcaa cgttgttgcc attgctacag gcatcgtggt gtcacgctcg tcgtttggta
```

FIG. 31C

```
6181    tggcttcatt cagctccggt tcccaacgat caaggcgagt tacatgatcc cccatgttgt
6241    gcaaaaaagc ggttagctcc ttcggtcctc cgatcgttgt cagaagtaag ttggccgcag
6301    tgttatcact catggttatg gcagcactgc ataattctct tactgtcatg ccatccgtaa
6361    gatgcttttc tgtgactggt gagtactcaa ccaagtcatt ctgagaatag tgtatgcggc
6421    gaccgagttg ctcttgcccg gcgtcaatac gggataatac cgcgccacat agcagaactt
6481    taaaagtgct catcattgga aaacgttctt cggggcgaaa actctcaagg atcttaccgc
6541    tgttgagatc cagttcgatg taacccactc gtgcacccaa ctgatcttca gcatctttta
6601    ctttcaccag cgtttctggg tgagcaaaaa caggaaggca aaatgccgca aaaaagggaa
6661    taagggcgac acggaaatgt tgaatactca tactcttcct ttttcaatat tattgaagca
6721    tttatcaggg ttattgtctc atgagcggat acatatttga atgtatttag aaaaataaac
6781    aaatagggggt tccgcgcaca tttccccgaa aagtgccacc tgacgtc
```

FIG. 32A

The sequence of the CMV expression vector expressing human codon optimized Vargula luciferase under control of the CMV promoter (not the vargula luciferase sequence) is in bold.

CMV promoter bases: 209-863
Vargula luciferase gene: 907–
T7 promoter bases: 864-882
Polylinker bases: 889-907 gacggatcgggagatctcccgatccccctatggtcgactctcagtacaatc tgctctgatgccgcatagttaagccagtatctgctccctgcttgtgtgtt
ggaggtcgctgagtagtgcgcgagcaaaatttaagctacaacaaggcaag gcttgaccgacaattgcatgaagaatctgcttaggggttaggcgttttgcg
ctgcttcgcgatgtacgggccagatatacgcgttgacattgattattgac tagttattaatagtaatcaattacggggtcattagttcatagcccatata
tggagttccgcgttacataacttacggtaaatggcccgcctggctgaccg cccaacgacccccgcccattgacgtcaataatgacgtatgttcccatagt
aacgccaataggggactttccattgacgtcaatgggtggactatttacggt aaactgcccacttggcagtacatcaagtgtatcatatgccaagtacgccc
cctattgacgtcaatgacggtaaatggcccgcctggcattatgcccagta catgaccttatgggactttcctacttggcagtacatctacgtattagtca
tcgctattaccatggtgatgcggttttggcagtacatcaatgggcgtgga tagcggtttgactcacggggatttccaagtctccaccccattgacgtcaa
tgggagtttgttttggcaccaaaatcaacgggactttccaaaatgtcgta acaactccgccccattgacgcaaatgggcggtaggcgtgtacggtgggag
gtctatataagcagagctctctggctaactagagaacccactgcttactg gcttatcgaaattaatacgactcactatagggagacccaagcttggtacc
gagctc ATGAAGATAATTATCCTTTCTGTGATTCTGGCTTACTGTGTTAC
AGTGAATTGTCAGGATGCATGTCCAGTAGAGGCGGAACCGCCATCTTCTA
CCCCGACCGTACCAACCTCCTGCGAAGCTAAAGAAGGGGAGTGCATCGAT
ACAAGGTGCGCTACCTGCAAACGGGATATCCTGTCCGACGGACTTTGCGA
AAATAAACCCGGGAAGACCTGCTGTCGAATGTGTCAGTATGTCATCGAAT
GCCGGGTCGAGGCCGCCGGTTATTTTAGAACATTTTACGGTAAACGGTTT
AATTTCCAGGAACCCGGCAAATACGTACTGGCTCGCGGCACCAAGGGTGG
CGACTGGAGCGTCACCCTGACAATGGAAAACCTGGACGGGCAGAAAGGAG
CCGTGCTTACTAAAACTACCCTGGAGGTGGCGGGAGACGTAATTGACATC
ACTCAGGCAACGGCTGACCCAATAACCGTGAACGGAGGAGCTGATCCCGT
GATTGCAAACCCTTTCACTATTGGCGAGGTCACGATTGCCGTCGTCGAAA
TTCCAGGCTTCAACATCACAGTGATCGAGTTCTTCAAGCTGATCGTCATT
GATATCCTCGGCGGACGGTCCGTTCGCATCGCACCTGACACAGCCAACAA
GGGCCTGATCTCTGGCATTTGTGGTAACTTGGAAATGAATGATGCTGATG
ACTTCACAACGGACGCCGACCAACTGGCCATTCAACCTAATATCAACAAA
GAGTTTGATGGATGTCCCTTTTACGGAAATCCTTCAGACATCGAATACTG
CAAAGGCCTCATGGAACCGTACCGGCCGTTTGCAGAAATAACATCAACT
TCTACTATTATACTCTGAGCTGCGCATTTGCATACTGTATGGGCGGTGAG
GAGAGAGCCAAACATGTGCTTTTCGACTATGTGGAGACCTGCGCCGCCCC
GGAGACTCGCGGTACCTGCGTCCTGAGCGGCCATACCTTCTATGACACCT
TCGATAAGGCTAGGTACCAGTTCCAAGGGCCTTGCAAAGAGCTCCTGATG
GCCGCAGATTGTTACTGGAACACTTGGGACGTCAAAGTTTCCCATCGGGA
CGTAGAGAGCTACACGGAAGTTGAGAAGGTGACCATCAGGAAGCAGAGTA
CCGTCGTAGACCTGATCGTCGACGGCAAGCAGGTAAAGGTAGGAGGCGTG
GACGTTAGTATTCCGTATTCTTCTGAAAATACGAGCATCTACTGGCAGGA
TGGAGACATTCTGACAACCGCCATCCTTCCAGAAGCTCTGGTGGTGAAGT
TTAACTTCAAGCAGCTGCTGGTAGTGCACATTCGCGACCCATTCGACGGG
AAAACCTGTGGGATTTGCGGCAACTACAACCAGGACTCAACTGACGATTT
CTTTGACGCCGAAGGGGCTTGCGCTCTTACCCCAAATCCGCCTGGATGCA
CCGAAGAGCAAAAGCCTGAAGCGGAACGGCTGTGCAATTCACTGTTTGAT
TCTTCAATAGATGAGAAATGCAACGTGTGTTACAAACCTGACCGCATCGC
ACGCTGCATGTATGAGTATTGCCTGAGAGGTCAACAAGGGTTCTGCGATC
ACGCGTGGGAATTTAAGAAAGAATGCTACATAAAGCACGGGGATACATTG
GAGGTGCCGCCAGAATGCCAGTAGtctagaaataattcttactgtcatgccaagtaagatgcttttctgtgctgcaat
agcaggcatgctggggatgcggtgggctctatggcttctgaggcggaaag aaccagctggggctctaggggtatcccacgcgccctgtagcggcgcat
taagcgcggcgggtgtggtggttacgcgcagcgtgaccgctacacttgcc agcgccctagcgcccgctcctttcgctttcttcccttccttctcgccac
gttcgccggctttccccgtcaagctctaaatcggggcatcccttaggggt tccgatttagtgctttacggcacctcgacccaaaaaacttgattagggt
gatggttcacgtagtgggccatcgccctgatagacggtttttcgccctt gacgttggagtccacgttctttaatagtggactcttgttccaaactggaa
caacactcaaccctatctcggtctattctttgatttataagggattttg gggatttcggcctattggttaaaaaatgagctgatttaacaaaaatttaa
cgcgaattaattctgtggaatgtgtgtcagttagggtgtggaaagtccc aggctcccaggcaggcagaagtatgcaaagcatgcatctcaattagtca
gcaaccaggtgtggaaagtccccaggctccccagcaggcagaagtatgca aagcatgcatctcaattagtcagcaaccatagtcccgcccctaactccgc
ccatcccgcccctaactccgcccagttccgcccattctccgccccatggc tgactaatttttttatttatgcagaggccgaggccgcctctgcctctga
gctattccagaagtagtgaggaggcttttttggaggcctaggcttttgca aaaagctcccgggagcttgtatatccatttcggatctgatcaagagaca
ggatgaggatcgtttcgcatgattgaacaagatggattgcacgcaggttc tccggccgcttgggtggagaggctattcggctatgactgggcacaacaga

FIG. 32B caatcggctgctctgatgccgccgtgttccggctgtcagcgcaggggcgc ccggttcttttttgtcaagaccgacctgtccggtgccctgaatgaactgca
ggacgaggcagcgcggctatcgtggctggccacgacgggcgttccttgcg cagctgtgctcgacgttgtcactgaagcgggaagggactggctgctattg
ggcgaagtgccggggcaggatctcctgtcatctcaccttgctcctgccga gaaagtatccatcatggctgatgcaatgcggcggctgcatacgcttgatc
cggctacctgccccattcgaccaccaagcgaaacatcgcatcgagcgagca cgtactcggatggaagccggtcttgtcgatcaggatgatctggacgaaga
gcatcaggggctcgcgccagccgaactgttcgccaggctcaaggcgcgca tgcccgacggcgaggatctcgtcgtgacccatggcgatgcctgcttgccg
aatatcatggtggaaaatggccgcttttctggattcatcgactgtggccg gctgggtgtggcggaccgctatcaggacatagcgttggctaccgtgata
ttgctgaagagcttggcggcgaatgggctgaccgcttcctcgtgctttac ggtatcgccgctcccgattcgcagcgcatcgccttctatcgccttcttga
cgagttcttctgagcgggactctggggttcgaaatgaccgaccaagcgac gcccaacctgccatcacgagatttcgattccaccgccgccttctatgaaa
ggttgggcttcggaatcgttttccgggacgccggctggatgatcctccag cgcgggggatctcatgctggagttcttcgcccacccaacttgtttattgc
agcttataatggttacaaataaagcaatagcatcacaaatttcacaaata aagcattttttcactgcattctagttgtggtttgtccaaactcatcaat
gtatcttatcatgtctgtataccgtcgacctctagctagagcttggcgta atcatggtcatagctgtttcctgtgtgaaattgttatccgctcacaattc
cacacaacatacgagccggaagcataaagtgtaaagcctggggtgcctaa tgagtgagctaactcacattaattgcgttgcgctcactgcccgctttcca
gtcgggaaacctgtcgtgccagctgcattaatgaatcggccaacgcgcgg ggagaggcggtttgcgtattgggcgctcttccgcttcctcgctcactgac
tcgctgcgctcggtcgttcggctgcggcgagcggtatcagctcactcaaa ggcggtaatacggttatccacagaatcaggggataacgcaggaaagaaca
tgtgagcaaaaggccagcaaaaggccaggaaccgtaaaaaggccgcgttg ctggcgtttttccataggctccgcccccctgacgagcatcacaaaaatcg
acgctcaagtcagaggtggcgaaacccgacaggactataaagataccagg cgtttccccctggaagctccctcgtgcgctctcctgttccgaccctgccg
cttaccggatacctgtccgcctttctcccttcgggaagcgtggcgctttc tcaatgctcacgctgtaggtatctcagttcggtgtaggtcgttcgctcca
agctgggctgtgtgcacgaaccccccgttcagcccgaccgctgcgcctta tccggtaactatcgtcttgagtccaacccggtaagacacgacttatcgcc
actggcagcagccactggtaacaggattagcagagcgaggtatgtaggcg gtgctacagagttcttgaagtggtggcctaactacggctacactagaagg
acagtatttggtatctgcgctctgctgaagccagttaccttcggaaaaag agttggtagctcttgatccggcaaacaaaccaccgctggtagcggtggtt
tttttgtttgcaagcagcagattacgcgcagaaaaaaaggatctcaagaa gatcctttgatcttttctacggggtctgacgctcagtggaacgaaaactc
acgttaagggattttggtcatgagattatcaaaaaggatcttcacctaga tccttttaaattaaaaatgaagttttaaatcaatctaaagtatatatgag
taaacttggtctgacagttaccaatgcttaatcagtgaggcacctatctc agcgatctgtctatttcgttcatccatagttgcctgactccccgtcgtgt
agataactacgatacgggagggcttaccatctggccccagtgctgcaatg ataccgcgagacccacgctcaccggctccagatttatcagcaataaacca
gccagccggaagggccgagcgcagaagtggtcctgcaactttatccgcct ccatccagtctattaattgttgccgggaagctagagtaagtagttcgcca
gttaatagtttgcgcaacgttgttgccattgctacaggcatcgtggtgtc acgctcgtcgtttggtatggcttcattcagctccggttcccaacgatcaa
ggcgagttacatgatcccccatgttgtgcaaaaaagcggttagctccttc ggtcctccgatcgttgtcagaagtaagttggccgcagtgttatcactcat
ggttatggcagcactgcataattctcttactgtcatgccatccgtaagat gcttttctgtgactggtgagtactcaaccaagtcattctgagaatagtgt
atgcggcgaccgagttgctcttgcccggcgtcaatacgggataataccgc gccacatagcagaactttaaaagtgctcatcattggaaaacgttcttcgg
ggcgaaaactctcaaggatcttaccgctgttgagatccagttcgatgtaa cccactcgtgcacccaactgatcttcagcatcttttactttcaccagcgt
ttctgggtgagcaaaaacaggaaggcaaaatgccgcaaaaaagggaataa gggcgacacggaaatgttgaatactcatactcttcctttttcaatattat
tgaagcatttatcagggttattgtctcatgagcggatacatatttgaatg tatttagaaaaataaacaaataggggttccgcgcacatttccccgaaaag
tgccacctgacgtc

SEQUENCE LISTING

```
<160> NUMBER OF SEQ ID NOS: 7

<210> SEQ ID NO 1
<211> LENGTH: 6173
<212> TYPE: DNA
<213> ORGANISM: Renilla reniformis

<400> SEQUENCE: 1
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacggga atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gcttggtacc     900
gagctcggat ccatgttgtt gaaagttgtg tttgctattg gatgtatcgt agtgcaggct     960
atggcctcaa aagtgtacga tccggagcag cggaagagga tgatcacggg gcccaatgg    1020 tgggcacgat gcaagcagat gaatgtgttg gacagtttca ttaactacta cgacagcgag    1080
aaacacgcgg agaacgcagt gatattcctg cacggcaatg caaccagtag ctatctgtgg    1140
agacacgtgg tgcctcatat tgagccggtc gctagatgca ttattcccga tcttattgga    1200 atgggaaat ccggaaagag tggaaatgga tcatataggc tcctcgatca ttataaatat    1260
ctgactgctt ggtttgaatt gctcaatctg cccaagaaaa tcatctttgt aggacatgat    1320
tggggctccg cccttgcttt tcattatgcc tatgaacacc aggatcggat caaggctatt    1380
gttcacatgg agagcgtggt ggatgtgatt gaatcatgga tgggttggcc ggatatagaa    1440
gaagagctgg cgctgattaa atctgaggag ggcgagaaga tggtactcga aaataacttc    1500
tttgtcgaga cggtactgcc cagtaagatc atgcgcaaac tggagcctga agagtttgcg    1560
gcttacctgg aacccttcaa ggagaaggga gaggtgagga gaccgaccct gtcatggcct    1620
```

```
cgggaaattc cgctggtcaa aggagggaag ccagacgtcg tcgccattgt ccggaattac    1680
aacgcttacc tccgcgctag tgacgacctg cctaaactct tcatcgaatc agatcctggt    1740
ttctttagta acgccatcgt cgagggcgcc aagaagtttc caaacaccga atttgttaaa    1800
gtcaaaggac ttcacttcct ccaggaggat gcgcccgatg aaatgggaaa gtatatcaaa    1860
tccttcgtgg agagggtctt gaagaatgag cagaggtcca tctagtctag aaataattct    1920
tactgtcatg ccaagtaaga tgcttttctg tgctgcaata gcaggcatgc tggggatgcg    1980
gtgggctcta tggcttctga ggcggaaaga accagctggg gctctagggg gtatccccac    2040
gcgccctgta gcggcgcatt aagcgcggcg ggtgtggtgg ttacgcgcag cgtgaccgct    2100
acacttgcca gcgccctagc gcccgctcct ttcgctttct tcccttcctt tctcgccacg    2160
ttcgccggct ttccccgtca agctctaaat cggggcatcc ctttagggtt ccgatttagt    2220
gctttacggc acctcgaccc caaaaaactt gattagggtg atggttcacg tagtgggcca    2280
tcgccctgat agacggtttt tcgccctttg acgttggagt ccacgttctt taatagtgga    2340
ctcttgttcc aaactggaac aacactcaac cctatctcgg tctattcttt tgatttataa    2400
gggattttgg ggatttcggc ctattggtta aaaaatgagc tgatttaaca aaaatttaac    2460
gcgaattaat tctgtggaat gtgtgtcagt tagggtgtgg aaagtcccca ggctcccag    2520 gcaggcagaa gtatgcaaag catgcatctc aattagtcag caaccaggtg tggaaagtcc    2580
ccaggctccc cagcaggcag aagtatgcaa agcatgcatc tcaattagtc agcaaccata    2640
gtcccgcccc taactccgcc catcccgccc ctaactccgc ccagttccgc ccattctccg    2700
ccccatggct gactaatttt ttttatttat gcagaggccg aggccgcctc tgcctctgag    2760
ctattccaga agtagtgagg aggctttttt ggaggcctag gcttttgcaa aaagctcccg    2820
ggagcttgta tatccatttt cggatctgat caagagacag gatgaggatc gtttcgcatg    2880
attgaacaag atggattgca cgcaggttct ccggccgctt gggtggagag gctattcggc    2940
tatgactggg cacaacagac aatcggctgc tctgatgccg ccgtgttccg gctgtcagcg    3000
caggggcgcc cggttctttt tgtcaagacc gacctgtccg gtgccctgaa tgaactgcag    3060
gacgaggcag cgcggctatc gtggctggcc acgacgggcg ttccttgcgc agctgtgctc    3120
gacgttgtca ctgaagcggg aagggactgg ctgctattgg gcgaagtgcc ggggcaggat    3180
ctcctgtcat ctcaccttgc tcctgccgag aaagtatcca tcatggctga tgcaatgcgg    3240
cggctgcata cgcttgatcc ggctacctgc ccattcgacc accaagcgaa acatcgcatc    3300
gagcgagcac gtactcggat ggaagccggt cttgtcgatc aggatgatct ggacgaagag    3360
catcaggggc tcgcgccagc cgaactgttc gccaggctca aggcgcgcat gcccgacggc    3420
gaggatctcg tcgtgaccca tggcgatgcc tgcttgccga atatcatggt ggaaaatggc    3480
cgcttttctg gattcatcga ctgtggccgg ctgggtgtgg cggaccgcta tcaggacata    3540
gcgttggcta cccgtgatat tgctgaagag cttggcggcg aatgggctga ccgcttcctc    3600
gtgctttacg gtatcgccgc tcccgattcg cagcgcatcg ccttctatcg ccttcttgac    3660
gagttcttct gagcgggact ctggggttcg aaatgaccga ccaagcgacg cccaacctgc    3720
catcacgaga tttcgattcc accgccgcct tctatgaaag gttgggcttc ggaatcgttt    3780
tccgggacgc cggctggatg atcctccagc gcggggatct catgctggag ttcttcgccc    3840
accccaactt gtttattgca gcttataatg gttacaaata aagcaatagc atcacaaatt    3900
tcacaaataa agcatttttt tcactgcatt ctagttgtgg tttgtccaaa ctcatcaatg    3960
```

```
tatcttatca tgtctgtata ccgtcgacct ctagctagag cttggcgtaa tcatggtcat    4020
agctgtttcc tgtgtgaaat tgttatccgc tcacaattcc acacaacata cgagccggaa    4080
gcataaagtg taaagcctgg ggtgcctaat gagtgagcta actcacatta attgcgttgc    4140
gctcactgcc cgctttccag tcgggaaacc tgtcgtgcca gctgcattaa tgaatcggcc    4200
aacgcgcggg gagaggcggt ttgcgtattg ggcgctcttc cgcttcctcg ctcactgact    4260
cgctgcgctc ggtcgttcgg ctgcggcgag cggtatcagc tcactcaaag gcggtaatac    4320
ggttatccac agaatcaggg gataacgcag gaaagaacat gtgagcaaaa ggccagcaaa    4380
aggccaggaa ccgtaaaaag gccgcgttgc tggcgttttt ccataggctc cgcccccctg    4440
acgagcatca caaaaatcga cgctcaagtc agaggtggcg aaacccgaca ggactataaa    4500
gataccaggc gtttccccct ggaagctccc tcgtgcgctc tcctgttccg accctgccgc    4560
ttaccggata cctgtccgcc tttctccctt cgggaagcgt ggcgctttct caatgctcac    4620
gctgtaggta tctcagttcg gtgtaggtcg ttcgctccaa gctgggctgt gtgcacgaac    4680
cccccgttca gcccgaccgc tgcgccttat ccggtaacta tcgtcttgag tccaacccgg    4740
taagacacga cttatcgcca ctggcagcag ccactggtaa caggattagc agagcgaggt    4800
atgtaggcgg tgctacagag ttcttgaagt ggtggcctaa ctacggctac actagaagga    4860
cagtatttgg tatctgcgct ctgctgaagc cagttacctt cggaaaaaga gttggtagct    4920
cttgatccgg caaacaaacc accgctggta gcggtggttt ttttgtttgc aagcagcaga    4980
ttacgcgcag aaaaaaagga tctcaagaag atcctttgat cttttctacg gggtctgacg    5040
ctcagtggaa cgaaaactca cgttaaggga ttttggtcat gagattatca aaaaggatct    5100
tcacctagat ccttttaaat taaaaatgaa gttttaaatc aatctaaagt atatatgagt    5160
aaacttggtc tgacagttac caatgcttaa tcagtgaggc acctatctca gcgatctgtc    5220
tatttcgttc atccatagtt gcctgactcc ccgtcgtgta gataactacg atacgggagg    5280
gcttaccatc tggccccagt gctgcaatga taccgcgaga cccacgctca ccggctccag    5340
atttatcagc aataaaccag ccagccggaa gggccgagcg cagaagtggt cctgcaactt    5400
tatccgcctc catccagtct attaattgtt gccgggaagc tagagtaagt agttcgccag    5460
ttaatagttt gcgcaacgtt gttgccattg ctacaggcat cgtggtgtca cgctcgtcgt    5520
ttggtatggc ttcattcagc tccggttccc aacgatcaag gcgagttaca tgatccccca    5580
tgttgtgcaa aaaagcggtt agctccttcg gtcctccgat cgttgtcaga agtaagttgg    5640
ccgcagtgtt atcactcatg gttatggcag cactgcataa ttctcttact gtcatgccat    5700
ccgtaagatg cttttctgtg actggtgagt actcaaccaa gtcattctga atagtgta     5760 tgcggcgacc gagttgctct tgcccggcgt caatacggga taataccgcg ccacatagca    5820
gaactttaaa agtgctcatc attggaaaac gttcttcggg gcgaaaactc tcaaggatct    5880
taccgctgtt gagatccagt tcgatgtaac ccactcgtgc acccaactga tcttcagcat    5940
cttttacttt caccagcgtt tctgggtgag caaaaacagg aaggcaaaat gccgcaaaaa    6000
agggaataag ggcgacacgg aaatgttgaa tactcatact cttccttttt caatattatt    6060
gaagcattta tcagggttat tgtctcatga gcggatacat atttgaatgt atttagaaaa    6120
ataaacaaat aggggttccg cgcacatttc cccgaaaagt gccacctgac gtc           6173

<210> SEQ ID NO 2
<211> LENGTH: 6839
<212> TYPE: DNA
<213> ORGANISM: Artificial Sequence
```

<220> FEATURE:
<223> OTHER INFORMATION: Modified red firefly luciferase with secretory
     signal

<400> SEQUENCE: 2

```
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg   120
cgagcaaaat taagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gcttggtacc   900
gagctcggat ccatggcctt cctgtggctg ctgtcctgct gggccctgct gggcaccacc   960
ttcggctacc cgatcgagga gggctctgcc ggcatccaat gcacaagta catgcaacaa  1020
tacgccaagc tcggcgccat cgccttcagt aacgccctga caggcgtcga catcagctac  1080
cagcagtact tcgacatcac gtgcagactc gccgaggcta tgaagaacta cggcatgaag  1140
ccagaaggac acatcgctct ctgtagcgag aactgcgaag agttcttcat tcctgttctg  1200
gctggtcttt acatcggagt tacagtcgcg ccaactaacg aaatttatac acttagagag  1260
ctgaaccaca gtctggggat agcccaacct actatcgtat tctctagcag gaagggcctg  1320
cccaaagtgc ttgaggtgca aagaccgtg acttgcatca aaaccattgt catcctggac  1380
agtaaggtca acttcggcgg ttatgactgc gtagagacct tcattaagaa acacgtcgag  1440
ctgggctttc ctgccacctc atttgtgccc atcgacgtca agaccggaa gcaccacatt  1500
gctctgctta tgaactcttc cggttccaca gggctgccca aggagtaga tcactcac   1560
gaggccctgg tcacgagatt ctctcacgct aaggaccta tatacggcaa tcaggtggcc  1620
ccaggtaccg ctatcctgac tgtcgtgcct ttccaccacg gcttcggaat gttcactact  1680
ttgggctact ttgcctgcgg ttaccggatt gtcatgctta ctaagttcga cgaggagctt  1740
ttcctgcgca cacttcagga ttacaagtgc actacagtaa tcctggtgcc gacactgttc  1800
gcaattctta ataggtctga gctccttgat aagtttgacc tctctaacct gactgaaata  1860
gccagcggtg gtgctccact tgccaaggag atcggcgagg ctgttgcaag aagattcaac  1920
ctcccaggcg tccggcaggg atatggactc accgagacta ccagtgcctt tatcatcact  1980
cctaagggcg acgacaagcc gggagccagc ggcaaggtcg tgcctctgtt caaggtgaag  2040
attattgacc tcgataccaa gaaaacgttg ggtgtcaaca gacggggaga atctgcgtg   2100
aaaggaccat ctcttatgtt gggatacacg aacaatcctg aagccaccag agaaactatt  2160
gacgaggaag gctggctgca cacgggtgac atcgggtact acgacgagga tgagcacttc  2220
```

```
tttatagtcg accgcctgaa atctctcatt aagtataaag gataccaagt gccaccagct    2280
gaactggagt ctgtgctcct gcaacaccct aacattagaa atgctggtgt ggccggggtt    2340
cccgacagcg aggcaggcga gctgcctgga gccgtcgttg tgatggaaaa gggaaagaca    2400
atgactgaga aagaaatcgt agactatgta aactcccagg tggtcaacca caagcggctg    2460
aggggcggcg tgcggttcgt agatgaagtc cccaaggggc tcacaggaaa gatcgacgcg    2520
aaagttatca gggagatact caagaaacct caagcaggtg ggtagtctag atctagaaat    2580
aattcttact gtcatgccaa gtaagatgct tttctgtgct gcaatagcag gcatgctggg    2640
gatgcggtgg gctctatggc ttctgaggcg aaagaaccca gctggggctc tagggggtat    2700
ccccacgcgc cctgtagcgg cgcattaagc gcggcgggtg tggtggttac gcgcagcgtg    2760
accgctacac ttgccagcgc cctagcgccc gctccttccg cttctcttcc ttcctttctc    2820
gccacgttcg ccggctttcc ccgtcaagct ctaaatcggg gcatcccttt agggttccga    2880
tttagtgctt tacggcacct cgaccccaaa aaacttgatt agggtgatgg ttcacgtagt    2940
gggccatcgc cctgatagac ggttttttcgc cctttgacgt tggagtccac gttctttaat    3000
agtggactct tgttccaaac tggaacaaca ctcaacccta tctcggtcta ttcttttgat    3060
ttataaggga ttttggggat tcggcctat tggttaaaaa atgagctgat ttaacaaaaa    3120
tttaacgcga attaattctg tggaatgtgt gtcagttagg gtgtggaaag tccccaggct    3180
ccccaggcag gcagaagtat gcaaagcatg catctcaatt agtcagcaac caggtgtgga    3240
aagtccccag gctccccagc aggcagaagt atgcaaagca tgcatctcaa ttagtcagca    3300
accatagtcc cgcccctaac tccgcccatc ccgcccctaa ctccgcccag ttccgcccat    3360
tctccgcccc atggctgact aatttttttt atttatgcag aggccgaggc cgcctctgcc    3420
tctgagctat tccagaagta gtgaggaggc ttttttggag gcctaggctt ttgcaaaaag    3480
ctcccgggag cttgtatatc cattttcgga tctgatcaag agacaggatg aggatcgttt    3540
cgcatgattg aacaagatgg attgcacgca ggttctccgg ccgcttgggt ggagaggcta    3600
ttcggctatg actgggcaca acagacaatc ggctgctctg atgccgccgt gttccggctg    3660
tcagcgcagg ggcgcccggt tctttttgtc aagaccgacc tgtccggtgc cctgaatgaa    3720
ctgcaggacg aggcagcgcg gctatcgtgg ctggccacga cgggcgttcc ttgcgcagct    3780
gtgctcgacg ttgtcactga agcgggaagg gactggctgc tattgggcga agtgccgggg    3840
caggatctcc tgtcatctca ccttgctcct gccgagaaag tatccatcat ggctgatgca    3900
atgcggcggc tgcatacgct tgatccggct acctgcccat tcgaccacca agcgaaacat    3960
cgcatcgagc gagcacgtac tcggatggaa gccggtcttg tcgatcagga tgatctggac    4020
gaagagcatc aggggctcgc gccagccgaa ctgttcgcca ggctcaaggc gcgcatgccc    4080
gacggcgagg atctcgtcgt gacccatggc gatgcctgct tgccgaatat catggtggaa    4140
aatggccgct tttctggatt catcgactgt ggccggctgg gtgtggcgga ccgctatcag    4200
gacatagcgt tggctacccg tgatattgct gaagagcttg gcggcgaatg ggctgaccgc    4260
ttcctcgtgc tttacggtat cgccgctccc gattcgcagc gcatcgcctt ctatcgcctt    4320
cttgacgagt tcttctgagc gggactctgg ggttcgaaat gaccgaccaa gcgacgccca    4380
acctgccatc acgagatttc gattccaccg ccgccttcta tgaaaggttg ggcttcggaa    4440
tcgtttccgg gacgccggc tggatgatcc tccagcgcgg ggatctcatg ctggagttct    4500
tcgcccaccc caacttgttt attgcagctt ataatggtta caaataaagc aatagcatca    4560
```

```
caaatttcac aaataaagca ttttttttcac tgcattctag ttgtggtttg tccaaactca    4620
tcaatgtatc ttatcatgtc tgtataccgt cgacctctag ctagagcttg gcgtaatcat    4680
ggtcatagct gtttcctgtg tgaaattgtt atccgctcac aattccacac aacatacgag    4740
ccggaagcat aaagtgtaaa gcctggggtg cctaatgagt gagctaactc acattaattg    4800
cgttgcgctc actgcccgct ttccagtcgg gaaacctgtc gtgccagctg cattaatgaa    4860
tcggccaacg cgcggggaga ggcggtttgc gtattgggcg ctcttccgct tcctcgctca    4920
ctgactcgct gcgctcggtc gttcggctgc ggcgagcggt atcagctcac tcaaaggcgg    4980
taatacggtt atccacagaa tcaggggata acgcaggaaa gaacatgtga gcaaaaggcc    5040
agcaaaaggc caggaaccgt aaaaaggccg cgttgctggc gtttttccat aggctccgcc    5100
cccctgacga gcatcacaaa aatcgacgct caagtcagag gtggcgaaac ccgacaggac    5160
tataaagata ccaggcgttt ccccctggaa gctccctcgt gcgctctcct gttccgaccc    5220
tgccgcttac cggatacctg tccgcctttc tcccttcggg aagcgtggcg ctttctcaat    5280
gctcacgctg taggtatctc agttcggtgt aggtcgttcg ctccaagctg gctgtgtgc    5340 acgaaccccc cgttcagccc gaccgctgcg ccttatccgg taactatcgt cttgagtcca    5400
acccggtaag acacgactta tcgccactgg cagcagccac tggtaacagg attagcagag    5460
cgaggtatgt aggcggtgct acagagttct tgaagtggtg gcctaactac ggctacacta    5520
gaaggacagt atttggtatc tgcgctctgc tgaagccagt taccttcgga aaaagagttg    5580
gtagctcttg atccggcaaa caaaccaccg ctggtagcgg tggtttttttt gtttgcaagc    5640 agcagattac gcgcagaaaa aaaggatctc aagaagatcc tttgatcttt tctacggggt    5700
ctgacgctca gtggaacgaa aactcacgtt aagggatttt ggtcatgaga ttatcaaaaa    5760
ggatcttcac ctagatcctt ttaaattaaa aatgaagttt aaatcaatc taaagtatat    5820 atgagtaaac ttggtctgac agttaccaat gcttaatcag tgaggcacct atctcagcga    5880
tctgtctatt tcgttcatcc atagttgcct gactccccgt cgtgtagata actacgatac    5940
gggagggctt accatctggc cccagtgctg caatgatacc gcgagaccca cgctcaccgg    6000
ctccagattt atcagcaata aaccagccag ccggaagggc cgagcgcaga agtggtcctg    6060
caactttatc cgcctccatc cagtctatta attgttgccg ggaagctaga gtaagtagtt    6120
cgccagttaa tagtttgcgc aacgttgttg ccattgctac aggcatcgtg gtgtcacgct    6180
cgtcgtttgg tatggcttca ttcagctccg gttcccaacg atcaaggcga gttacatgat    6240
cccccatgtt gtgcaaaaaa gcggttagct ccttcggtcc tccgatcgtt gtcagaagta    6300
agttggccgc agtgttatca ctcatggtta tggcagcact gcataattct cttactgtca    6360
tgccatccgt aagatgcttt tctgtgactg gtgagtactc aaccaagtca ttctgagaat    6420
agtgtatgcg gcgaccgagt tgctcttgcc cggcgtcaat acgggataat accgcgccac    6480
atagcagaac tttaaaagtg ctcatcattg gaaaacgttc ttcggggcga aaactctcaa    6540
ggatcttacc gctgttgaga tccagttcga tgtaacccac tcgtgcaccc aactgatctt    6600
cagcatcttt tactttcacc agcgtttctg ggtgagcaaa aacaggaagg caaaatgccg    6660
caaaaaaggg aataagggcg acacggaaat gttgaatact catactcttc ctttttcaat    6720
attattgaag catttatcag ggttattgtc tcatgagcgg atacatattt gaatgtattt    6780
agaaaaataa acaaataggg gttccgcgca catttccccg aaaagtgcca cctgacgtc    6839
```

<210> SEQ ID NO 3
<211> LENGTH: 6833

<212> TYPE: DNA
<213> ORGANISM: Artificial Sequence
<220> FEATURE:
<223> OTHER INFORMATION: A mammalian expression vector expressing Red emitting firefly luciferase (human codon optimized signal) under control of the CMV promoter)

<400> SEQUENCE: 3

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccatggaaac agaaagagaa gaaaacgttg tctacggccc actgccattc    960
taccccgatcg aggagggctc tgccggcatc caattgcaca gtacatgca acaatacgcc   1020
aagctcggcg ccatcgcctt cagtaacgcc ctgacaggcg tcgacatcag ctaccagcag   1080
tacttcgaca tcacgtgcag actcgccgag gctatgaaga actacggcat gaagccagaa   1140
ggacacatcg ctctctgtag cgagaactgc gaagagttct tcattcctgt tctggctggt   1200
ctttacatcg gagttacagt cgcgccaact aacgaaattt atacttag agagctgaac    1260
cacagtctgg ggatagccca acctactatc gtattctcta gcaggaaggg cctgcccaaa   1320
gtgcttgagg tgcagaagac cgtgacttgc atcaaaacca ttgtcatcct ggacagtaag   1380
gtcaacttcg gcggttatga ctgcgtagag accttcatta agaaacacgt cgagctgggc   1440
tttcctgcca cctcatttgt gcccatcgac gtcaaagacc ggaagcacca cattgctctg   1500
cttatgaact cttccggttc cacagggctg cccaaggag tagagatcac tcacgaggcc   1560
ctggtcacga gattctctca cgctaaggac cctatatacg caatcaggt ggccccaggt   1620
accgctatcc tgactgtcgt gccttttccac cacggcttcg gaatgttcac tactttgggc   1680
tactttgcct gcggttaccg gattgtcatg cttactaagt cgacgagga cttttcctg   1740
cgcacacttc aggattacaa gtgcactaca gtaatcctgg tgccgacact gttcgcaatt   1800
cttaataggt ctgagctcct tgataagttt gacctctcta acctgactga aatagccagc   1860
ggtggtgctc cacttgccaa ggagatcggc gaggctgttg caagaagatt caacctccca   1920
ggcgtccggc agggatatgg actcaccgag actaccagtg cctttatcat cactcctaag   1980
ggcgacgaca gccgggagc cagcggcaag gtcgtgcctc tgttcaaggt gaagattatt   2040
gacctcgata ccaagaaaac gttgggtgtc aacagacggg agaaatctg cgtgaaagga   2100
```

```
ccatctctta tgttgggata cacgaacaat cctgaagcca ccagagaaac tattgacgag    2160
gaaggctggc tgcacacggg tgacatcggg tactacgacg aggatgagca cttctttata    2220
gtcgaccgcc tgaaatctct cattaagtat aaaggatacc aagtgccacc agctgaactg    2280
gagtctgtgc tcctgcaaca ccctaacatt agagatgctg gtgtggccgg ggttcccgac    2340
agcgaggcag gcgagctgcc tggagccgtc gttgtgatgg aaaagggaaa gacaatgact    2400
gagaaagaaa tcgtagacta tgtaaactcc caggtggtca accacaagcg gctgaggggc    2460
ggcgtgcggt tcgtagatga agtccccaag gggctcacag aaagatcga cgcgaaagtt     2520 atcagggaga tactcaagaa acctcaagca ggtgggtagt ctagatctag aaataattct    2580
tactgtcatg ccaagtaaga tgcttttctg tgctgcaata gcaggcatgc tggggatgcg    2640
gtgggctcta tggcttctga ggcggaaaga accagctggg gctctagggg gtatccccac    2700
gcgccctgta gcggcgcatt aagcgcggcg ggtgtggtgg ttacgcgcag cgtgaccgct    2760
acacttgcca gcgccctagc gcccgctcct ttcgctttct tcccttcctt tctcgccacg    2820
ttcgccggct ttccccgtca agctctaaat cggggcatcc ctttagggtt ccgatttagt    2880
gctttacggc acctcgaccc caaaaaactt gattagggtg atggttcacg tagtgggcca    2940
tcgccctgat agacggtttt tcgccctttg acgttggagt ccacgttctt taatagtgga    3000
ctcttgttcc aaactggaac aacactcaac cctatctcgg tctattcttt tgatttataa    3060
gggattttgg ggatttcggc ctattggtta aaaaatgagc tgatttaaca aaaatttaac    3120
gcgaattaat tctgtggaat gtgtgtcagt tagggtgtgg aaagtcccca ggctccccag    3180
gcaggcagaa gtatgcaaag catgcatctc aattagtcag caaccaggtg tggaaagtcc    3240
ccaggctccc cagcaggcag aagtatgcaa agcatgcatc tcaattagtc agcaaccata    3300
gtcccgcccc taactccgcc catcccgccc taactccgcc cagttccgcc cattctccg    3360 ccccatggct gactaatttt ttttatttat gcagaggccg aggccgcctc tgcctctgag    3420
ctattccaga agtagtgagg aggcttttt ggaggcctag gcttttgcaa aaagctcccg     3480
ggagcttgta tatccatttt cggatctgat caagagacag gatgaggatc gtttcgcatg    3540
attgaacaag atggattgca cgcaggttct ccggccgctt gggtggagag gctattcggc    3600
tatgactggg cacaacagac aatcggctgc tctgatgccg ccgtgttccg gctgtcagcg    3660
caggggcgcc cggttctttt tgtcaagacc gacctgtccg gtgccctgaa tgaactgcag    3720
gacgaggcag cgcggctatc gtggctggcc acgacgggcg ttccttgcgc agctgtgctc    3780
gacgttgtca ctgaagcggg aagggactgg ctgctattgg gcgaagtgcc ggggcaggat    3840
ctcctgtcat ctcaccttgc tcctgccgag aaagtatcca tcatggctga tgcaatgcgg    3900
cggctgcata cgcttgatcc ggctacctgc ccattcgacc accaagcgaa acatcgcatc    3960
gagcgagcac gtactcggat ggaagccggt cttgtcgatc aggatgatct ggacgaagag    4020
catcaggggc tcgcgccagc cgaactgttc gccaggctca aggcgcgcat gcccgacggc    4080
gaggatctcg tcgtgaccca tggcgatgcc tgcttgccga atatcatggt ggaaaatggc    4140
cgcttttctg gattcatcga ctgtggccgg ctgggtgtgg cggaccgcta tcaggacata    4200
gcgttggcta cccgtgatat tgctgaagag cttggcggcg aatgggctga ccgcttcctc    4260
gtgctttacg gtatcgccgc tcccgattcg cagcgcatcg ccttctatcg ccttcttgac    4320
gagttcttct gagcgggact ctggggttcg aaatgaccga ccaagcgacg cccaacctgc    4380
catcacgaga tttcgattcc accgccgcct tctatgaaag gttgggcttc ggaatcgttt    4440
tccgggacgc cggctggatg atcctccagc gcggggatct catgctggag ttcttcgccc    4500
```

```
accccaactt gtttattgca gcttataatg gttacaaata aagcaatagc atcacaaatt    4560
tcacaaataa agcattttt tcactgcatt ctagttgtgg tttgtccaaa ctcatcaatg     4620
tatcttatca tgtctgtata ccgtcgacct ctagctagag cttggcgtaa tcatggtcat    4680
agctgtttcc tgtgtgaaat tgttatccgc tcacaattcc acacaacata cgagccggaa    4740
gcataaagtg taaagcctgg ggtgcctaat gagtgagcta actcacatta attgcgttgc    4800
gctcactgcc cgctttccag tcgggaaacc tgtcgtgcca gctgcattaa tgaatcggcc    4860
aacgcgcggg gagaggcggt ttgcgtattg ggcgctcttc cgcttcctcg ctcactgact    4920
cgctgcgctc ggtcgttcgg ctgcggcgag cggtatcagc tcactcaaag gcggtaatac    4980
ggttatccac agaatcaggg gataacgcag gaaagaacat gtgagcaaaa ggccagcaaa    5040
aggccaggaa ccgtaaaaag gccgcgttgc tggcgttttt ccataggctc cgcccccctg    5100
acgagcatca caaaaatcga cgctcaagtc agaggtggcg aaacccgaca ggactataaa    5160
gataccaggc gtttccccct ggaagctccc tcgtgcgctc tcctgttccg accctgccgc    5220
ttaccggata cctgtccgcc tttctccctt cgggaagcgt ggcgctttct caatgctcac    5280
gctgtaggta tctcagttcg gtgtaggtcg ttcgctccaa gctgggctgt gtgcacgaac    5340
cccccgttca gcccgaccgc tgcgccttat ccggtaacta tcgtcttgag tccaacccgg    5400
taagacacga cttatcgcca ctggcagcag ccactggtaa caggattagc agagcgaggt    5460
atgtaggcgg tgctacagag ttcttgaagt ggtggcctaa ctacggctac actagaagga    5520
cagtatttgg tatctgcgct ctgctgaagc cagttacctt cggaaaaaga gttggtagct    5580
cttgatccgg caaacaaacc accgctggta gcggtggttt ttttgtttgc aagcagcaga    5640
ttacgcgcag aaaaaaagga tctcaagaag atcctttgat cttttctacg ggtctgacg    5700
ctcagtggaa cgaaaactca cgttaaggga ttttggtcat gagattatca aaaaggatct    5760
tcacctagat ccttttaaat taaaaatgaa gttttaaatc aatctaaagt atatatgagt    5820
aaacttggtc tgacagttac caatgcttaa tcagtgaggc acctatctca gcgatctgtc    5880
tatttcgttc atccatagtt gcctgactcc ccgtcgtgta gataactacg atacgggagg    5940
gcttaccatc tggccccagt gctgcaatga taccgcgaga cccacgctca ccggctccag    6000
atttatcagc aataaaccag ccagccggaa gggccgagcg cagaagtggt cctgcaactt    6060
tatccgcctc catccagtct attaattgtt gccgggaagc tagagtaagt agttcgccag    6120
ttaatagttt gcgcaacgtt gttgccattg ctacaggcat cgtggtgtca cgctcgtcgt    6180
ttggtatggc ttcattcagc tccggttccc aacgatcaag gcgagttaca tgatccccca    6240
tgttgtgcaa aaaagcggtt agctccttcg gtcctccgat cgttgtcaga agtaagttgg    6300
ccgcagtgtt atcactcatg gttatggcag cactgcataa ttctcttact gtcatgccat    6360
ccgtaagatg cttttctgtg actggtgagt actcaaccaa gtcattctga gaatagtgta    6420
tgcggcgacc gagttgctct tgcccggcgt caatacggga taataccgcg ccacatagca    6480
gaactttaaa agtgctcatc attggaaaac gttcttcggg gcgaaaactc tcaaggatct    6540
taccgctgtt gagatccagt tcgatgtaac ccactcgtgc acccaactga tcttcagcat    6600
cttttacttt caccagcgtt tctgggtgag caaaaacagg aaggcaaaat gccgcaaaaa    6660
agggaataag ggcgacacgg aaatgttgaa tactcatact cttccttttt caatattatt    6720
gaagcattta tcagggttat tgtctcatga gcggatacat atttgaatgt atttagaaaa    6780
ataaacaaat aggggttccg cgcacatttc cccgaaaagt gccacctgac gtc          6833
```

```
<210> SEQ ID NO 4
<211> LENGTH: 6827
<212> TYPE: DNA
<213> ORGANISM: Luciola italica
<220> FEATURE:
<221> NAME/KEY: CMV promoter bases
<222> LOCATION: (209) .. (863)
<220> FEATURE:
<221> NAME/KEY: Green emitting firefly luciferase gene
<222> LOCATION: (907) .. (2560)
<220> FEATURE:
<221> NAME/KEY: T7 promoter bases
<222> LOCATION: (1827) .. (1845)
<220> FEATURE:
<221> NAME/KEY: Polylinker bases
<222> LOCATION: (1852) .. (1870)
<220> FEATURE:
<221> NAME/KEY: Synthetic polyadenylation site
<222> LOCATION: (2560) .. (2604)
<220> FEATURE:
<221> NAME/KEY: SP6 promoter
<222> LOCATION: (2576) .. (2593)
<220> FEATURE:
<221> NAME/KEY: SV40 promoter bases
<222> LOCATION: (3145) .. (3480)
<220> FEATURE:
<221> NAME/KEY: SV40 origin of replication: bases
<222> LOCATION: (3259) .. (3344)
<220> FEATURE:
<221> NAME/KEY: Neomycin ORF bases
<222> LOCATION: (3516) .. (4310)
<220> FEATURE:
<221> NAME/KEY: ColE1 origin: bases
<222> LOCATION: (3934) .. (4607)
<220> FEATURE:
<221> NAME/KEY: SV40 PolyA: bases
<222> LOCATION: (4365) .. (4737)
<220> FEATURE:
<221> NAME/KEY: Ampicillin ORF: bases
<222> LOCATION: (4752) .. (5612)

<400> SEQUENCE: 4
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccatggaaac agaaagagaa gaaacgttg tctacggccc actgccattc    960
tacccgatcg aggagggctc tgccggcatc caattgcaca agtacatgca acaatacgcc   1020
aagctcggcg ccatcgcctt cagtaacgcc ctgacaggcg tcgacatcag ctaccagcag   1080
```

```
tacttcgaca tcacgtgcag actcgccgag gctatgaaga actacggcat gaagccagaa    1140
ggacacatcg ctctctgtag cgagaactgc gaagagttct tcattcctgt tctggctggt    1200
ctttacatcg gagttacagt cgcgccaact aacgaaattt atacacttag agagctgaac    1260
cacagtctgg ggatagccca acctactatc gtattctcta gcaggaaggg cctgcccaaa    1320
gtgcttgagg tgcagaagac cgtgacttgc atcaaaacca ttgtcatcct ggacagtaag    1380
gtcaacttcg gcggttatga ctgcgtagag accttcatta gaaacacgt cgagctgggc     1440 tttcctgcca cctcatttgt gcccatcgac gtcaaagacc ggaagcacca cattgctctg    1500
cttatgaact cttccggttc cacagggctg cccaaaggag tagagatcac tcacgaggcc    1560
ctggtcacga gattctctca cgctaaggac cctatatacg gcaatcaggt ggccccaggt    1620
accgctatcc tgactgtcat ccctttccac cacgccttcg gaatgagcac tactttgggc    1680
tactttgcct gcggttaccg gattgtcatg cttactaagt tcgacgagga gcttttcctg    1740
cgcacacttc aggattacaa gtgcactagc gtaatcctgg tgccgacact gttcgcaatt    1800
cttaataggt ctgagctcct tgataagttt gacctctcta acctgactga aatagccagc    1860
ggtggtgctc cacttgccaa ggagatcggc gaggctgttg caagaagatt caacctccca    1920
ggcgtccggc agggatatgg actcaccgag actaccagtg cctttatcat cactcctaag    1980
ggcgacgaca agccgggagc cagcggcaag gtcgtgcctc tgttcaaggt gaagattatt    2040
gacctcgata ccaagaaaac gttgggtgtc aacagacggg gagaaatctg cgtgaaagga    2100
ccatctctta tgttgggata cacgaacaat cctgaagcca ccagagaaac tattgacgag    2160
gaaggctggc tgcacacggg tgacatcggg tactacgacg aggatgagca cttctttata    2220
gtcgaccgcc tgaaatctct cattaagtat aaaggatacc aagtgccacc agctgaactg    2280
gagtctgtgc tcctgcaaca ccctaacatt agagatgctg gtgtggccgg ggttcccgac    2340
agcgaggcag gcgagctgcc tggagccgtc gttgtgatgg aaaagggaaa gacaatgact    2400
gagaaagaaa tcgtagacta tgtaaactcc caggtggtca accacaagcg gctgaggggc    2460
ggcgtgcggt tcgtagatga agtccccaag gggctcacag aaagatcga cgcgaaagtt     2520 atcagggaga tactcaagaa acctcaagca ggtgggtagt ctagaaataa ttcttactgt    2580
catgccaagt aagatgcttt tctgtgctgc aatagcaggc atgctgggga tgcggtgggc    2640
tctatggctt ctgaggcgga aagaaccagc tggggctcta gggggtatcc ccacgcgccc    2700
tgtagcggcg cattaagcgc ggcgggtgtg gtggttacgc gcagcgtgac cgctacactt    2760
gccagcgccc tagcgcccgc tcctttcgct ttcttccctt cctttctcgc cacgttcgcc    2820
ggctttcccc gtcaagctct aaatcggggc atccctttag ggttccgatt tagtgcttta    2880
cggcacctcg accccaaaaa acttgattag ggtgatggtt cacgtagtgg gccatcgccc    2940
tgatagacgg ttttcgccc tttgacgttg gagtccacgt tctttaatag tggactcttg     3000
ttccaaactg gaacaacact caaccctatc tcggtctatt cttttgattt ataagggatt    3060
ttggggattt cggcctattg gttaaaaaat gagctgattt aacaaaaatt taacgcgaat    3120
taattctgtg gaatgtgtgt cagttagggt gtggaaagtc cccaggctcc ccaggcaggc    3180
agaagtatgc aaagcatgca tctcaattag tcagcaacca ggtgtggaaa gtccccaggc    3240
tccccagcag gcagaagtat gcaaagcatg catctcaatt agtcagcaac catagtcccg    3300
cccctaactc cgcccatccc gcccctaact ccgcccagtt ccgcccattc tccgccccat    3360
ggctgactaa ttttttttat ttatgcagag gccgaggccg cctctgcctc tgagctattc    3420
```

```
cagaagtagt gaggaggctt ttttggaggc ctaggctttt gcaaaaagct cccgggagct    3480
tgtatatcca ttttcggatc tgatcaagag acaggatgag gatcgtttcg catgattgaa    3540
caagatggat tgcacgcagg ttctccggcc gcttgggtgg agaggctatt cggctatgac    3600
tgggcacaac agacaatcgg ctgctctgat gccgccgtgt tccggctgtc agcgcagggg    3660
cgcccggttc tttttgtcaa gaccgacctg tccggtgccc tgaatgaact gcaggacgag    3720
gcagcgcggc tatcgtggct ggccacgacg ggcgttcctt gcgcagctgt gctcgacgtt    3780
gtcactgaag cgggaaggga ctggctgcta ttgggcgaag tgccggggca ggatctcctg    3840
tcatctcacc ttgctcctgc cgagaaagta tccatcatgg ctgatgcaat gcggcggctg    3900
catacgcttg atccggctac ctgcccattc gaccaccaag cgaaacatcg catcgagcga    3960
gcacgtactc ggatggaagc cggtcttgtc gatcaggatg atctggacga agagcatcag    4020
gggctcgcgc cagccgaact gttcgccagg ctcaaggcgc gcatgcccga cggcgaggat    4080
ctcgtcgtga cccatggcga tgcctgcttg ccgaatatca tggtggaaaa tggccgcttt    4140
tctggattca tcgactgtgg ccggctgggt gtggcggacc gctatcagga catagcgttg    4200
gctacccgtg atattgctga agagcttggc ggcgaatggg ctgaccgctt cctcgtgctt    4260
tacggtatcg ccgctcccga ttcgcagcgc atcgccttct atcgccttct tgacgagttc    4320
ttctgagcgg gactctgggg ttcgaaatga ccgaccaagc gacgcccaac ctgccatcac    4380
gagatttcga ttccaccgcc gccttctatg aaaggttggg cttcggaatc gttttccggg    4440
acgccggctg gatgatcctc cagcgcgggg atctcatgct ggagttcttc gcccacccca    4500
acttgtttat tgcagcttat aatggttaca aataaagcaa tagcatcaca aatttcacaa    4560
ataaagcatt ttttcactg cattctagtt gtggtttgtc caaactcatc aatgtatctt    4620
atcatgtctg tataccgtcg acctctagct agagcttggc gtaatcatgg tcatagctgt    4680
ttcctgtgtg aaattgttat ccgctcacaa ttccacacaa catacgagcc ggaagcataa    4740
agtgtaaagc ctggggtgcc taatgagtga gctaactcac attaattgcg ttgcgctcac    4800
tgcccgcttt ccagtcggga aacctgtcgt gccagctgca ttaatgaatc ggccaacgcg    4860
cggggagagg cggtttgcgt attgggcgct cttccgcttc ctcgctcact gactcgctgc    4920
gctcggtcgt tcggctgcgg cgagcggtat cagctcactc aaaggcggta atacggttat    4980
ccacagaatc aggggataac gcaggaaaga acatgtgagc aaaaggccag caaaaggcca    5040
ggaaccgtaa aaaggccgcg ttgctggcgt ttttccatag gctccgcccc cctgacgagc    5100
atcacaaaaa tcgacgctca agtcagaggt ggcgaaaccc gacaggacta taaagatacc    5160
aggcgtttcc ccctggaagc tccctcgtgc gctctcctgt tccgaccctg ccgcttaccg    5220
gatacctgtc cgcctttctc ccttcgggaa gcgtggcgct ttctcaatgc tcacgctgta    5280
ggtatctcag ttcggtgtag tcgttcgct ccaagctggg ctgtgtgcac gaaccccccg    5340
ttcagcccga ccgctgcgcc ttatccggta actatcgtct tgagtccaac ccggtaagac    5400
acgacttatc gccactggca gcagccactg gtaacaggat tagcagagcg aggtatgtag    5460
gcggtgctac agagttcttg aagtggtggc ctaactacgg ctacactaga aggacagtat    5520
ttggtatctg cgctctgctg aagccagtta ccttcggaaa aagagttggt agctcttgat    5580
ccggcaaaca aaccaccgct ggtagcggtg gtttttttgt ttgcaagcag cagattacgc    5640
gcagaaaaaa aggatctcaa gaagatcctt tgatctttc tacggggtct gacgctcagt    5700
ggaacgaaaa ctcacgttaa gggattttgg tcatgagatt atcaaaaagg atcttcacct    5760
agatcctttt aaattaaaaa tgaagtttta aatcaatcta agtatatat gagtaaactt    5820
```

```
ggtctgacag ttaccaatgc ttaatcagtg aggcacctat ctcagcgatc tgtctatttc    5880
gttcatccat agttgcctga ctccccgtcg tgtagataac tacgatacgg agggcttac     5940 catctggccc cagtgctgca atgataccgc gagacccacg ctcaccggct ccagatttat    6000
cagcaataaa ccagccagcc ggaagggccg agcgcagaag tggtcctgca actttatccg    6060
cctccatcca gtctattaat tgttgccggg aagctagagt aagtagttcg ccagttaata    6120
gtttgcgcaa cgttgttgcc attgctacag gcatcgtggt gtcacgctcg tcgtttggta    6180
tggcttcatt cagctccggt tcccaacgat caaggcgagt tacatgatcc cccatgttgt    6240
gcaaaaaagc ggttagctcc ttcggtcctc cgatcgttgt cagaagtaag ttggccgcag    6300
tgttatcact catggttatg gcagcactgc ataattctct tactgtcatg ccatccgtaa    6360 gatgctttc tgtgactggt gagtactcaa ccaagtcatt ctgagaatag tgtatgcggc     6420
gaccgagttg ctcttgcccg gcgtcaatac gggataatac cgcgccacat agcagaactt    6480
taaaagtgct catcattgga aaacgttctt cggggcgaaa actctcaagg atcttaccgc    6540
tgttgagatc cagttcgatg taacccactc gtgcacccaa ctgatcttca gcatctttta    6600
ctttcaccag cgtttctggg tgagcaaaaa caggaaggca aaatgccgca aaaaagggaa    6660
taagggcgac acggaaatgt tgaatactca tactcttcct ttttcaatat tattgaagca    6720
tttatcaggg ttattgtctc atgagcggat acatatttga atgtatttag aaaaataaac    6780
aaataggggt tccgcgcaca tttccccgaa aagtgccacc tgacgtc                  6827

<210> SEQ ID NO 5
<211> LENGTH: 6834
<212> TYPE: DNA
<213> ORGANISM: Renilla reniformis

<400> SEQUENCE: 5
gacggatcgg gagatctccc gatccctat ggtcgactct cagtacaatc tgctctgatg       60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc      180
ttagggttag gcgttttgcg ctgcttcgcg atgtacgggc cagatatacg cgttgacatt     240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgcc ccattgacg caaatgggcg     780 gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccagccacca tggaaacaga agagaagaa aacgttgtct acggcccact     960
gccattctac ccgatcgagg agggctctgc cggcatccaa ttgcacaagt acatgcaaca    1020
atacgccaag ctcggcgcca tcgccttcag taacgccctg acaggcgtcg acatcagcta    1080
```

```
ccagcagtac ttcgacatca cgtgcagact cgccgaggct atgaagaact acggcatgaa    1140
gccagaagga cacatcgctc tctgtagcga gaactgcgaa gagttcttca ttcctgttct    1200
ggctggtctt tacatcggag ttacagtcgc gccaactaac gaaatttata cacttagaga    1260
gctgaaccac agtctgggga tagcccaacc tactatcgta ttctctagca ggaagggcct    1320
gcccaaagtg cttgaggtgc agaagaccgt gacttgcatc aaaaccattg tcatcctgga    1380
cagtaaggtc aacttcggcg ttatgactg cgtagagacc ttcattaaga aacacgtcga    1440
gctgggcttt cctgccacct catttgtgcc catcgacgtc aaagaccgga agcaccacat    1500
tgctctgctt atgaactctt ccggttccac agggctgccc aaaggagtag agatcactca    1560
cgaggccctg gtcacgagat tctctcacgc taaggaccct atatacggca atcaggtggc    1620
cccaggtacc gctatcctga ctgtcgtgcc tttccaccac ggcttcggaa tgttcactac    1680
tttgggctac tttgcctgcg gttaccggat tgtcatgctt actaagttcg acgaggagct    1740
tttcctgcgc acacttcagg attacaagtg cactacagta atcctggtgc cgacactgtt    1800
cgcaattctt aataggtctg agctccttga taagtttgac ctctctaacc tgactgaaat    1860
agccagcggt ggtgctccac ttgccaagga gatcggcgag gctgttgcaa gaagattcaa    1920
cctcccaggc gtccggcagg gatatggact caccgagact accagtgcct ttatcatcac    1980
tcctaagggc gacgacaagc cgggagccag cggcaaggtc gtgcctctgt caaggtgaa    2040 gattattgac ctcgatacca agaaaacgtt gggtgtcaac agacggggag aaatctgcgt    2100
gaaaggacca tctcttatgt tgggatacac gaacaatcct gaagccacca gagaaactat    2160
tgacgaggaa ggctggctgc acacgggtga catcgggtac tacgacgagg atgagcactt    2220
ctttatagtc gaccgcctga aatctctcat taagtataaa ggataccaag tgccaccagc    2280
tgaactggag tctgtgctcc tgcaacaccc taacattaga gatgctggtg tggccggggt    2340
tcccgacagc gaggcaggcg agctgcctgg agccgtcgtt gtgatggaaa agggaaagac    2400
aatgactgag aaagaaatcg tagactatgt aaactcccag gtggtcaacc acaagcggct    2460
gaggggcggc gtgcggttcg tagatgaagt ccccaagggg ctcacaggaa agatcgacgc    2520
gaaagttatc agggagatac tcaagaaacc tcaagcaggt gggtagtcta gaaataattc    2580
ttactgtcat gccaagtaag atgcttttct gtgctgcaat agcaggcatg ctgggatgc    2640 ggtgggctct atggcttctg aggcggaaag aaccagctgg ggctctaggg ggtatcccca    2700
cgcgccctgt agcggcgcat taagcgcggc gggtgtggtg gttacgcgca gcgtgaccgc    2760
tacacttgcc agcgccctag cgcccgctcc tttcgctttc ttcccttcct ttctcgccac    2820
gttcgccggc tttccccgtc aagctctaaa tcggggcatc cctttagggt tccgatttag    2880
tgctttacgg cacctcgacc ccaaaaaact tgattaggt gatggttcac gtagtgggcc    2940
atcgccctga tagacggttt ttcgcccttt gacgttggag tccacgttct ttaatagtgg    3000
actcttgttc caaactggaa caacactcaa ccctatctcg gtctattctt ttgatttata    3060
agggattttg gggatttcgg cctattggtt aaaaaatgag ctgatttaac aaaaatttaa    3120
cgcgaattaa ttctgtggaa tgtgtgtcag ttagggtgtg gaaagtcccc aggctcccca    3180
ggcaggcaga agtatgcaaa gcatgcatct caattagtca gcaaccaggt gtggaaagtc    3240
cccaggctcc ccagcaggca gaagtatgca aagcatgcat ctcaattagt cagcaaccat    3300
agtcccgccc ctaactccgc ccatcccgcc ctaactccg cccagttccg cccattctcc    3360
gccccatggc tgactaattt tttttattta tgcagaggcc gaggccgcct ctgcctctga    3420
gctattccag aagtagtgag gaggcttttt tggaggccta ggcttttgca aaaagctccc    3480
```

-continued

```
gggagcttgt atatccattt tcggatctga tcaagagaca ggatgaggat cgtttcgcat    3540
gattgaacaa gatggattgc acgcaggttc tccggccgct ggggtggaga ggctattcgg    3600
ctatgactgg gcacaacaga caatcggctg ctctgatgcc gccgtgttcc ggctgtcagc    3660 gcagggcgc ccggttcttt ttgtcaagac cgacctgtcc ggtgccctga atgaactgca    3720
ggacgaggca gcgcggctat cgtggctggc cacgacgggc gttccttgcg cagctgtgct    3780
cgacgttgtc actgaagcgg aagggactg gctgctattg ggcgaagtgc cggggcagga    3840
tctcctgtca tctcaccttg ctcctgccga aaagtatcc atcatggctg atgcaatgcg    3900
gcggctgcat acgcttgatc cggctacctg cccattcgac caccaagcga acatcgcat    3960 cgagcgagca cgtactcgga tggaagccgg tcttgtcgat caggatgatc tggacgaaga    4020
gcatcagggg ctcgcgccag ccgaactgtt cgccaggctc aaggcgcgca tgcccgacgg    4080
cgaggatctc gtcgtgaccc atggcgatgc ctgcttgccg aatatcatgg tggaaaatgg    4140
ccgcttttct ggattcatcg actgtggccg gctgggtgtg gcggaccgct atcaggacat    4200
agcgttggct acccgtgata ttgctgaaga gcttggcggc gaatgggctg accgcttcct    4260
cgtgctttac ggtatcgccg ctcccgattc gcagcgcatc gccttctatc gccttcttga    4320
cgagttcttc tgagcgggac tctggggttc gaaatgaccg accaagcgac gcccaacctg    4380
ccatcacgag atttcgattc caccgccgcc ttctatgaaa ggttgggctt cggaatcgtt    4440
ttccgggacg ccggctggat gatcctccag cgcggggatc tcatgctgga gttcttcgcc    4500 cacccccaact tgtttattgc agcttataat ggttacaaat aaagcaatag catcacaaat    4560
ttcacaaata aagcatttttt ttcactgcat tctagttgtg gtttgtccaa actcatcaat    4620
gtatcttatc atgtctgtat accgtcgacc tctagctaga gcttggcgta atcatggtca    4680
tagctgtttc ctgtgtgaaa ttgttatccg ctcacaattc cacacaacat acgagccgga    4740
agcataaagt gtaaagcctg gggtgcctaa tgagtgagct aactcacatt aattgcgttg    4800
cgctcactgc ccgctttcca gtcgggaaac ctgtcgtgcc agctgcatta atgaatcggc    4860
caacgcgcgg ggagaggcgg tttgcgtatt gggcgctctt ccgcttcctc gctcactgac    4920
tcgctgcgct cggtcgttcg gctgcggcga gcggtatcag ctcactcaaa ggcggtaata    4980
cggttatcca cagaatcagg ggataacgca ggaaagaaca tgtgagcaaa aggccagcaa    5040
aaggccagga accgtaaaaa ggccgcgttg ctggcgtttt tccataggct ccgcccccct    5100
gacgagcatc acaaaaatcg acgctcaagt cagaggtggc gaaacccgac aggactataa    5160
agataccagg cgtttccccc tggaagctcc ctcgtgcgct ctcctgttcc gaccctgccg    5220
cttaccggat acctgtccgc ctttctccct tcgggaagcg tggcgctttc tcaatgctca    5280
cgctgtaggt atctcagttc ggtgtaggtc gttcgctcca agctgggctg tgtgcacgaa    5340
ccccccgttc agcccgaccg ctgcgcctta tccggtaact atcgtcttga gtccaacccg    5400
gtaagacacg acttatcgcc actggcagca gccactggta acaggattag cagagcgagg    5460
tatgtaggcg gtgctacaga gttcttgaag tggtggccta actacggcta cactagaagg    5520
acagtatttg gtatctgcgc tctgctgaag ccagttacct tcggaaaaag agttggtagc    5580
tcttgatccg gcaaacaaac caccgctggt agcggtggtt tttttgtttg caagcagcag    5640
attacgcgca gaaaaaaagg atctcaagaa gatcctttga tcttttctac ggggtctgac    5700
gctcagtgga acgaaaactc acgttaaggg attttggtca tgagattatc aaaaaggatc    5760
ttcacctaga tccttttaaa ttaaaaatga agttttaaat caatctaaag tatatatgag    5820
```

```
taaacttggt ctgacagtta ccaatgctta atcagtgagg cacctatctc agcgatctgt      5880
ctatttcgtt catccatagt tgcctgactc cccgtcgtgt agataactac gatacgggag      5940
ggcttaccat ctggccccag tgctgcaatg ataccgcgag acccacgctc accggctcca      6000
gatttatcag caataaacca gccagccgga agggccgagc gcagaagtgg tcctgcaact      6060
ttatccgcct ccatccagtc tattaattgt tgccgggaag ctagagtaag tagttcgcca      6120
gttaatagtt tgcgcaacgt tgttgccatt gctacaggca tcgtggtgtc acgctcgtcg      6180
tttggtatgg cttcattcag ctccggttcc caacgatcaa ggcgagttac atgatccccc      6240
atgttgtgca aaaagcggt tagctccttc ggtcctccga tcgttgtcag aagtaagttg       6300
gccgcagtgt tatcactcat ggttatggca gcactgcata attctcttac tgtcatgcca      6360
tccgtaagat gcttttctgt gactggtgag tactcaacca agtcattctg agaatagtgt      6420
atgcggcgac cgagttgctc ttgcccggcg tcaatacggg ataataccgc gccacatagc      6480
agaactttaa aagtgctcat cattggaaaa cgttcttcgg ggcgaaaact ctcaaggatc      6540
ttaccgctgt tgagatccag ttcgatgtaa cccactcgtg cacccaactg atcttcagca      6600
tcttttactt tcaccagcgt ttctgggtga gcaaaaacag gaaggcaaaa tgccgcaaaa      6660
aagggaataa gggcgacacg gaaatgttga atactcatac tcttcctttt tcaatattat      6720
tgaagcattt atcagggtta ttgtctcatg agcggataca tatttgaatg tatttagaaa      6780
aataaacaaa taggggttcc gcgcacattt ccccgaaaag tgccacctga cgtc           6834
```

<210> SEQ ID NO 6
<211> LENGTH: 6842
<212> TYPE: DNA
<213> ORGANISM: Artificial Sequence
<220> FEATURE:
<223> OTHER INFORMATION: The sequence of the CMV expression vector
      expressing human codon optimized Vargula luciferase under control
      of the CMV promoter
<220> FEATURE:
<221> NAME/KEY: CMV promoter bases
<222> LOCATION: (209)..(863)
<220> FEATURE:
<221> NAME/KEY: T7 promoter bases
<222> LOCATION: (864)..(882)
<220> FEATURE:
<221> NAME/KEY: Polylinker bases
<222> LOCATION: (889)..(907)
<220> FEATURE:
<221> NAME/KEY: Vargula luciferase gene
<222> LOCATION: (907)..(6842)

<400> SEQUENCE: 6

```
gacggatcgg gagatctccc gatcccctat ggtcgactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc      420
attgacgtca atgggtggac tatttacggt aaactgccca cttggcagta catcaagtgt       480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
```

```
actcacgggg atttccaagt ctccacccca ttgacgtcaa tgggagtttg ttttggcacc      720
aaaatcaacg gacttttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gcttggtacc      900
gagctcatga agataattat cctttctgtg attctggctt actgtgttac agtgaattgt      960
caggatgcat gtccagtaga ggcggaaccg ccatcttcta ccccgaccgt accaacctcc     1020
tgcgaagcta aagaagggga gtgcatcgat acaaggtgcg ctacctgcaa acgggatatc     1080
ctgtccgacg gactttgcga aaataaaccc gggaagacct gctgtcgaat gtgtcagtat     1140
gtcatcgaat gccgggtcga ggccgccggt tattttagaa cattttacgg taaacggttt     1200
aatttccagg aacccggcaa atacgtactg gctcgcggca ccaagggtgg cgactggagc     1260
gtcaccctga caatggaaaa cctggacggg cagaaaggag ccgtgcttac taaaactacc     1320
ctggaggtgg cggagacgt aattgacatc actcaggcaa cggctgaccc aataaccgtg      1380
aacggaggag ctgatcccgt gattgcaaac cctttcacta ttggcgaggt cacgattgcc     1440
gtcgtcgaaa ttccaggctt caacatcaca gtgatcgagt tcttcaagct gatcgtcatt     1500
gatatcctcg gcggacggtc cgttcgcatc gcacctgaca cagccaacaa gggcctgatc     1560
tctggcattt gtggtaactt ggaaatgaat gatgctgatg acttcacaac ggacgccgac     1620
caactggcca ttcaacctaa tatcaacaaa gagtttgatg gatgtccctt ttacggaaat     1680
ccttcagaca tcgaatactg caaaggcctc atggaaccgt accgggccgt ttgcagaaat     1740
aacatcaact tctactatta tactctgagc tgcgcatttg catactgtat gggcggtgag     1800
gagagagcca aacatgtgct tttcgactat gtggagacct cgccgccccc ggagactcgc     1860
ggtacctgcg tcctgagcgg ccataccttc tatgacacct tcgataaggc taggtaccag     1920
ttccaagggc cttgcaaaga gctcctgatg gccgcagatt gttactggaa cacttgggac     1980
gtcaaagttt cccatcggga cgtagagagc tacacgaaag ttgagaaggt gaccatcagg     2040
aagcagagta ccgtcgtaga cctgatcgtc gacggcaagc aggtaaaggt aggaggcgtg     2100
gacgttagta ttccgtattc ttctgaaaat acgagcatct actggcagga tggagacatt     2160
ctgacaaccg ccatccttcc agaagctctg gtggtgaagt ttaacttcaa gcagctgctg     2220
gtagtgcaca ttcgcgaccc attcgacggg aaaacctgtg ggatttgcgg caactacaac     2280
caggactcaa ctgacgattt cttttgacgcc gaaggggctt gcgctcttac cccaaatccg     2340
cctggatgca ccgaagagca aaagcctgaa gcggaacggc tgtgcaattc actgtttgat     2400
tcttcaatag atgagaaatg caacgtgtgt acaaacctg accgcatcgc acgctgcatg     2460
tatgagtatt gcctgagagg tcaacaaggg ttctgcgatc acgcgtggga atttaagaaa     2520
gaatgctaca taaagcacgg ggatacattg gaggtgccgc cagaatgcca gtagtctaga     2580
aataattctt actgtcatgc caagtaagat gcttttctgt gctgcaatag caggcatgct     2640
ggggatgcgg tgggctctat ggcttctgag gcggaaagaa ccagctgggg ctctaggggg     2700
tatccccacg cgccctgtag cggcgcatta agcgcggcgg gtgtggtggt tacgcgcagc     2760
gtgaccgcta cacttgccag cgccctagcg cccgctcctt tcgctttctt cccttccttt     2820
ctcgccacgt tcgccggctt tccccgtcaa gctctaaatc ggggcatccc tttagggttc     2880
```

-continued

```
cgatttagtg ctttacggca cctcgacccc aaaaaacttg attagggtga tggttcacgt    2940
agtgggccat cgccctgata gacggttttt cgcccttgga cgttggagtc cacgttcttt    3000
aatagtggac tcttgttcca aactggaaca acactcaacc ctatctcggt ctattctttt    3060
gatttataag ggattttggg gatttcggcc tattggttaa aaaatgagct gatttaacaa    3120
aaatttaacg cgaattaatt ctgtggaatg tgtgtcagtt agggtgtgga aagtccccag    3180 gctcccccagg caggcagaag tatgcaaagc atgcatctca attagtcagc aaccaggtgt    3240
ggaaagtccc caggctcccc agcaggcaga gtatgcaaa gcatgcatct caattagtca    3300
gcaaccatag tcccgcccct aactccgccc atcccgcccc taactccgcc cagttccgcc    3360
cattctccgc cccatggctg actaattttt tttatttatg cagaggccga ggccgcctct    3420
gcctctgagc tattccagaa gtagtgagga ggcttttttg gaggcctagg cttttgcaaa    3480
aagctcccgg gagcttgtat atccattttc ggatctgatc aagagacagg atgaggatcg    3540
tttcgcatga ttgaacaaga tggattgcac gcaggttctc cggccgcttg ggtggagagg    3600
ctattcggct atgactgggc acaacagaca atcggctgct ctgatgccgc cgtgttccgg    3660
ctgtcagcgc aggggcgccc ggttcttttt gtcaagaccg acctgtccgg tgccctgaat    3720
gaactgcagg acgaggcagc gcggctatcg tggctggcca cgacgggcgt tccttgcgca    3780
gctgtgctcg acgttgtcac tgaagcggga agggactggc tgctattggg cgaagtgccg    3840
gggcaggatc tcctgtcatc tcaccttgct cctgccgaga aagtatccat catggctgat    3900
gcaatgcggc ggctgcatac gcttgatccg gctacctgcc cattcgacca ccaagcgaaa    3960
catcgcatcg agcgagcacg tactcggatg gaagccggtc ttgtcgatca ggatgatctg    4020
gacgaagagc atcaggggct cgcgccagcc gaactgttcg ccaggctcaa ggcgcgcatg    4080
cccgacggcg aggatctcgt cgtgacccat ggcgatgcct gcttgccgaa tatcatggtg    4140
gaaaatggcc gcttttctgg attcatcgac tgtggccggc tgggtgtggc ggaccgctat    4200
caggacatag cgttggctac ccgtgatatt gctgaagagc ttggcggcga atgggctgac    4260
cgcttcctcg tgctttacgg tatcgccgct cccgattcgc agcgcatcgc cttctatcgc    4320
cttcttgacg agttcttctg agcgggactc tggggttcga aatgaccgac caagcgacgc    4380
ccaacctgcc atcacgagat ttcgattcca ccgccgcctt ctatgaaagg ttgggcttcg    4440
gaatcgtttt ccgggacgcc ggctggatga tcctccagcg cggggatctc atgctggagt    4500
tcttcgccca ccccaacttg tttattgcag cttataatgg ttacaaataa agcaatagca    4560
tcacaaattt cacaaataaa gcatttttt cactgcattc tagttgtggt ttgtccaaac    4620
tcatcaatgt atcttatcat gtctgtatac cgtcgacctc tagctagagc ttggcgtaat    4680
catggtcata gctgtttcct gtgtgaaatt gttatccgct cacaattcca cacaacatac    4740
gagccggaag cataaagtgt aaagcctggg gtgcctaatg agtgagctaa ctcacattaa    4800
ttgcgttgcg ctcactgccc gctttccagt cgggaaacct gtcgtgccag ctgcattaat    4860
gaatcggcca acgcgcgggg agaggcggtt tgcgtattgg gcgctcttcc gcttcctcgc    4920
tcactgactc gctgcgctcg gtcgttcggc tgcggcgagc ggtatcagct cactcaaagg    4980
cggtaatacg gttatccaca gaatcagggg ataacgcagg aaagaacatg tgagcaaaag    5040
gccagcaaaa ggccaggaac cgtaaaaagg ccgcgttgct ggcgtttttc cataggctcc    5100
gcccccctga cgagcatcac aaaaatcgac gctcaagtca gaggtggcga aacccgacag    5160
gactataaag ataccaggcg tttccccctg gaagctccct cgtgcgctct cctgttccga    5220
```

```
ccctgccgct taccggatac ctgtccgcct ttctcccttc gggaagcgtg gcgctttctc    5280
aatgctcacg ctgtaggtat ctcagttcgg tgtaggtcgt tcgctccaag ctgggctgtg    5340
tgcacgaacc ccccgttcag cccgaccgct gcgccttatc cggtaactat cgtcttgagt    5400
ccaacccggt aagacacgac ttatcgccac tggcagcagc cactggtaac aggattagca    5460
gagcgaggta tgtaggcggt gctacagagt tcttgaagtg gtggcctaac tacggctaca    5520
ctagaaggac agtatttggt atctgcgctc tgctgaagcc agttaccttc ggaaaaagag    5580
ttggtagctc ttgatccggc aaacaaacca ccgctggtag cggtggtttt tttgtttgca    5640
agcagcagat tacgcgcaga aaaaaggat ctcaagaaga tcctttgatc ttttctacgg     5700
ggtctgacgc tcagtggaac gaaaactcac gttaagggat tttggtcatg agattatcaa    5760
aaaggatctt cacctagatc cttttaaatt aaaaatgaag ttttaaatca atctaaagta    5820
tatatgagta aacttggtct gacagttacc aatgcttaat cagtgaggca cctatctcag    5880
cgatctgtct atttcgttca tccatagttg cctgactccc cgtcgtgtag ataactacga    5940
tacgggaggg cttaccatct ggccccagtg ctgcaatgat accgcgagac ccacgctcac    6000
cggctccaga tttatcagca ataaaccagc cagccggaag ggccgagcgc agaagtggtc    6060
ctgcaacttt atccgcctcc atccagtcta ttaattgttg ccgggaagct agagtaagta    6120
gttcgccagt taatagtttg cgcaacgttg ttgccattgc tacaggcatc gtggtgtcac    6180
gctcgtcgtt tggtatggct tcattcagct ccggttccca acgatcaagg cgagttacat    6240 gatccccat gttgtgcaaa aaagcggtta gctccttcgg tcctccgatc gttgtcagaa     6300
gtaagttggc cgcagtgtta tcactcatgg ttatggcagc actgcataat tctcttactg    6360
tcatgccatc cgtaagatgc ttttctgtga ctggtgagta ctcaaccaag tcattctgag    6420
aatagtgtat gcggcgaccg agttgctctt gcccggcgtc aatacgggat aataccgcgc    6480
cacatagcag aactttaaaa gtgctcatca ttggaaaacg ttcttcgggg cgaaaactct    6540
caaggatctt accgctgttg agatccagtt cgatgtaacc cactcgtgca cccaactgat    6600
cttcagcatc ttttactttc accagcgttt ctgggtgagc aaaaacagga aggcaaaatg    6660
ccgcaaaaaa gggaataagg gcgacacgga aatgttgaat actcatactc ttcctttttc    6720
aatattattg aagcatttat cagggttatt gtctcatgag cggatacata tttgaatgta    6780
tttagaaaaa taaacaaata ggggttccgc gcacatttcc ccgaaaagtg ccacctgacg    6840
tc                                                                   6842
```

<210> SEQ ID NO 7
<211> LENGTH: 16
<212> TYPE: PRT
<213> ORGANISM: Artificial Sequence
<220> FEATURE:
<223> OTHER INFORMATION: Secretory signal

<400> SEQUENCE: 7

```
Met Leu Leu Lys Val Val Phe Ala Ile Gly Cys Ile Val Val Gln Ala
 1               5                  10                  15
```

US 9,353,401 B2

MULTIPLEX ASSAYS WITH MULTIPLE LUCIFERASES REPORTERS AND USES THEREOF

RELATED APPLICATIONS

This application claims the benefit of priority to U.S. Provisional Patent Application No. 61/238,146, filed on Aug. 29, 2009, which is hereby incorporated by reference in its entirety.

FIELD OF THE INVENTION

The present invention concerns the field of luciferase reporters useful in biological and biochemical assays.

BACKGROUND OF THE INVENTION

Luciferases are enzymes that catalyze reactions that emit light. Luciferases are named according to their source organisms such as beetles (firefly) or marine organisms. Examples of bioluminescent marine animals include: *Renilla*, also known as sea pansies, which belong to a class of coelenterates known as the anthozoans. In addition to *Renilla*, other representative bioluminescent genera of the class Anthozoa include *Cavarnularia, Ptilosarcus, Stylatula, Acanthoptilum*, and *Parazoanthus*. All of these organisms are bioluminescent and emit light as a result of the action of an enzyme (luciferase) on a substrate (luciferin) under appropriate biological conditions.

Different luciferases have different properties with regard to substrate specificity and intensity of light emission and stability of the bioluminescent signal, which is commonly measured by a luminometer. Luciferases are useful as transcriptional reporter genes and in imaging reporter gene expression in living subjects and many other applications in molecular biology.

Certain luciferases, such as those that utilize *cypridina* luciferin (vargulin) as a substrate, can be useful reporters because of their strong luminescent signal and the fact that they are secreted in the native form. However *cypridina* luciferin (vargulin) is very difficult to synthesize (usually involving an 18-step chemical synthesis). The limiting supply and the cost of the material have made the assay difficult to commercialize.

SUMMARY OF THE INVENTION

Accordingly, the present invention provides modified luciferases, methods of making modified luciferases, and methods of using modified luciferases.

In one aspect, the present invention provides an isolated polynucleotide that encodes a modified *Luciola Italica* (also referred to as *L. Italica*) luciferase. In a further aspect, the modified *L. Italica* luciferase shows increased luciferase activity when expressed in mammalian cells as compared to a non human codon optimized mutant *L. Italica* luciferase.

In an embodiment and in accordance with any of the above, the present invention provides a modified *L. Italica* luciferase that shows an approximately 1000-fold increased luciferase activity when expressed in mammalian cells as compared to a non human codon optimized mutant *L. Italica* luciferase.

In a further embodiment and in accordance with any of the above, the present invention provides a modified *L. Italica* luciferase that is a red-emitting luciferase with an emission maximum of approximately 617 nm.

In a further embodiment and in accordance with any of the above, the present invention provides a modified *L. Italica* luciferase that is human codon-optimized.

In a further embodiment and in accordance with any of the above, the present invention provides a modified *L. Italica* luciferase that is a green-emitting luciferase with an emission maximum of approximately 550 nm.

In a further embodiment and in accordance with any of the above, the present invention provides a modified *L. Italica* luciferase that includes a secretory signal at its amino terminal end. In a still further embodiment, the secretory signal is a chymotrypsinogen secretory signal.

In one aspect, the present invention provides assays utilizing any of the modified luciferases discussed herein. In a further aspect, the assays are multiplexed reporter assays.

In one aspect, the present invention provides an isolated polynucleotide that encodes a modified *Renilla* luciferase. In a further aspect, the modified *Renilla* luciferase shows increased activity and stability over a native human codon optimized *Renilla* luciferase.

In an exemplary embodiment the present invention provides a modified *Renilla* luciferase that is a green-emitting *Renilla* luciferase.

In a further embodiment and in accordance with any of the above, the invention provides a modified *Renilla* luciferase that includes a secretory signal at its amino terminal end.

In one aspect, the present invention provides multiplexed luciferase assays comprising at least two different luciferase reports, where the at least two different luciferase reporters emit at two different wavelengths and/or utilize different substrates.

BRIEF DESCRIPTION OF THE DRAWINGS

FIG. 2 shows data for time course of activity in a *Cypridina* assay using 5 µl of sample (FIG. 2A) or 20 µl of sample (FIG. 2A).

FIG. 3A-B shows the sequence of a green *Renilla* luciferase plasmid (SEQ ID NO: 1).

FIG. 4 shows the sequence of a modified red firefly luciferase with a secretory signal (SEQ ID NO: 2).

FIG. 27 shows the sequence of a red firefly luciferase of the invention (SEQ ID NO: 5).

FIG. 30 shows the sequence of a red emitting firefly human codon optimized luciferase of the invention (SEQ ID NO: 3).

FIG. 31 shows the sequence of a human codon optimized green firefly luciferase of the invention (SEQ ID NO: 4).

FIG. 32 shows the sequence of a human codon optimized *Vargula* luciferase of the invention (SEQ ID NO: 6).

DETAILED DESCRIPTION

Figure 1:
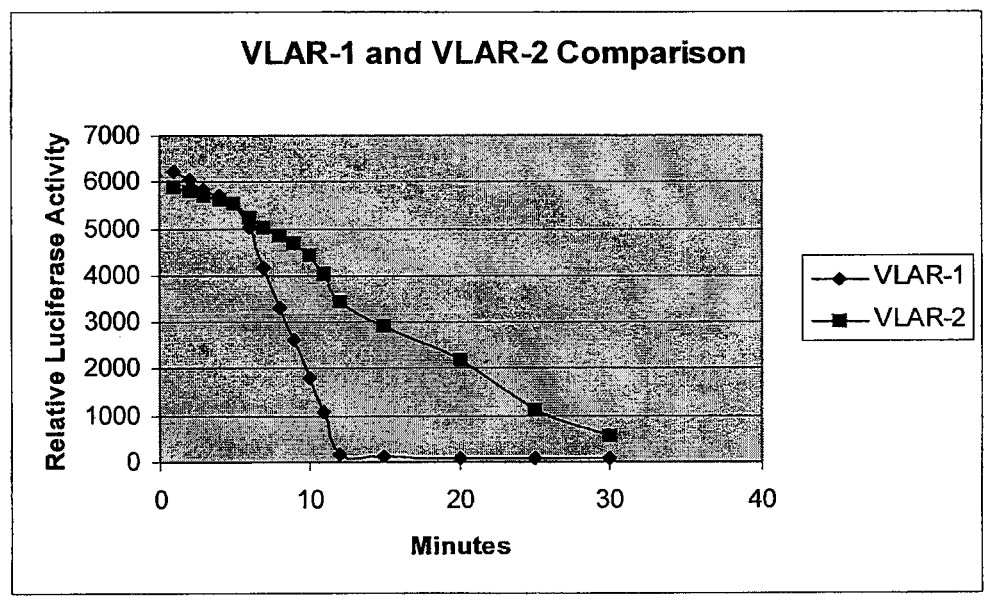
FIG. 1 shows data for relative luciferase stability for a *Cypridina* assay conducted using reagents without sodium chloride (VLAR-1) and with sodium chloride (VLAR-1 with sodium chloride).

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. It will be apparent to one of skill in the art that these additional features are also encompassed by the present invention.

Overview

The present invention provides modified luciferases and/or combinations of luciferases, and methods of utilizing those luciferases in reporter gene assays. In addition, the invention provides reagents that provide increased stability and activity in assays using luciferase reporters.

The present invention provides modified (also referred to herein as "mutant" or "variant") luciferases showing improved activity over wildtype luciferases or other modified luciferases known in the art reported to have improved properties for reporter gene assays or in vivo imaging applications. As used herein, "wildtype luciferases" refers to any luciferase that occurs in nature.

In certain aspects, the present invention provides modified luciferases that show brighter luminescence when expressed in mammalian cells as compared to the luminescence seen when wildtype luciferases are expressed in mammalian cells. The present invention also provides a method of expressing luciferase as a very bright intracellular reporter (not secreted) by sequence modification to increase its utility as an intracellular reporter in multiplexed assays and for imaging applications. The present invention also provides a composition for assays utilizing luciferases that lowers the cost and increases the efficiency and sensitivity of the assay by altering the reaction conditions such that high luminescence is produced using significantly less amount of luciferin.

The present invention further provides reagents for assays utilizing modified luciferases of the invention as well as mammalian expression vectors expressing secreted and intracellular luciferases.

In further embodiments the present invention provides sequence modifications (human codon optimization) to nucleotides encoding luciferases which result in an approximately 1000-fold increase in luciferase expression in transfected mammalian cells compared to the non-human codon optimized versions of these genes.

In further embodiments, the invention provides novel secreted reporter modified luciferases that are about 5 to about 35 fold brighter than wildtype luciferases. Such luciferases are used in accordance with the present invention as stand alone reporters or in multiplexed luciferase assays in combination with one or more other luciferases. As will be appreciated, combinations of luciferases for multiplexed assays of the invention can include both wildtype and modified luciferases.

In further aspects, the present invention provides assay compositions for measurement of modified luciferases of the invention as single luciferase assay formats. In further aspects of the invention, assay compositions are provided that enable simultaneous measurement of at least two different reporters in cell lysates or supernatants using a single assay solution. The luciferase activities of multiple reporters are analyzed by exploiting spectral differences in the emission maxima of the different luciferases.

Improved luciferases used in the present invention include without limitation: (i) a red-emitting firefly luciferase (Red-Fluc) from the Italian firefly *Luciola Italica* (emission max 609 nm), including intracellular (non-secreted) variants and secreted variants generated by fusing a chymotrypsinogen secretory signal sequence to the amino terminal end of the luciferase; (ii) a green-emitting firefly luciferase (Green-Fluc) from the Italian firefly *Luciola Italica* (emission max 550 nm), including intracellular (non-secreted) variants and secreted variants generated by fusing a chymotrypsinogen secretory signal sequence to the amino terminal end of the luciferase; (iii) a *Cypridina* Luciferase or *Vargula* luciferase (VLuc) from the marine ostracod *Vargula Hilgendorfi*, a secreted luciferase (emission max 395 nm or 462 nm depending on the substrate used); (iv) *Vargula* luciferase that has been modified at the C-terminal end with a KDEL sequence (endoplasmic reticulum retention signal) so that it is expressed intracellularly-VLuc-KDEL; (v) a modified secreted blue-emitting (emission max 480 nm) *Renilla* luciferase (B-Rluc) which is brighter and more stable than native *renilla reniformis* luciferase; (vi) a green emitting secreted *Renilla* luciferase (emission max 535 nm) modified to be secreted by fusing a synthetic secretory signal encoding gene sequence in frame with the gene encoding the green emitting modified of *renilla* luciferase; (vii) a *Gaussia* luciferase (emission max 482 nm) either native secreted (Gluc) or modified to be expressed intracellularly (Gluc-KDEL).

Luciferases of the Invention

Modified luciferases of the present invention show increased signal magnitude and stability. In certain embodiments, modified luciferases of the invention show at least a 1, 2, 3, 4, 5, 10, 50, 100, 250, 500, 750, 1000, 2000, 3000, 4000, 5000, 6000, 7000, 8000, 9000, 10,000-fold increase in the magnitude of the signal over signals seen with wildtype luciferases.

Modified luciferases of the invention may be intracellular (i.e., not secreted), or they may be modified to be secreted. In further embodiments, modified luciferases of the invention are engineered to further express a secretory signal, general at the amino terminal end. In some embodiments, the secretory signal is a synthetic sequence. In specific embodiments, the synthetic sequence is MLLK VVFA IGCI WQA (SEQ ID NO: 7). In yet further embodiments, the secretory signal is any signal that can induce secretion of the encoded protein, including without limitation an interleukin-2 secretory signal and a chymotrypsinogen secretory signal.

*Vargula* Luciferases of the Invention

In some aspects, the present invention provides a *Cypridina* Luciferase or *Vargula* luciferase (VLuc) from the marine ostracod *Vargula Hilgendorfi*, which is a secreted luciferase (emission max 395 nm or 462 nm depending on the substrate used).

In further aspects, the present invention provides a modified *Vargula* luciferase that shows increased signal and stability. In certain embodiments, the modified *Vargula* luciferase of the invention is human codon optimized to increase expression in mammalian systems. In further embodiments, a modified *Vargula* luciferase of the invention includes a wildtype or a native human codon optimized luciferase with the last two amino acids have been mutated CQ to SN (S=serine, N=asparagine). In still further embodiments, the present invention provides a mammalian vector expressing modified human codon optimized *Vargula* luciferase expressing intracellular *Vargula* luciferase. This sequence is the same as the wildtype or native human codon *Vargula* luciferase with the last two amino acids mutated CQ to SN (S=serine, N=asparagine) and with a KDEL (endoplasmic reticulum retention) sequence added after the C-terminal asparagine residue.

Firefly Luciferases of the Invention

Figure 8:
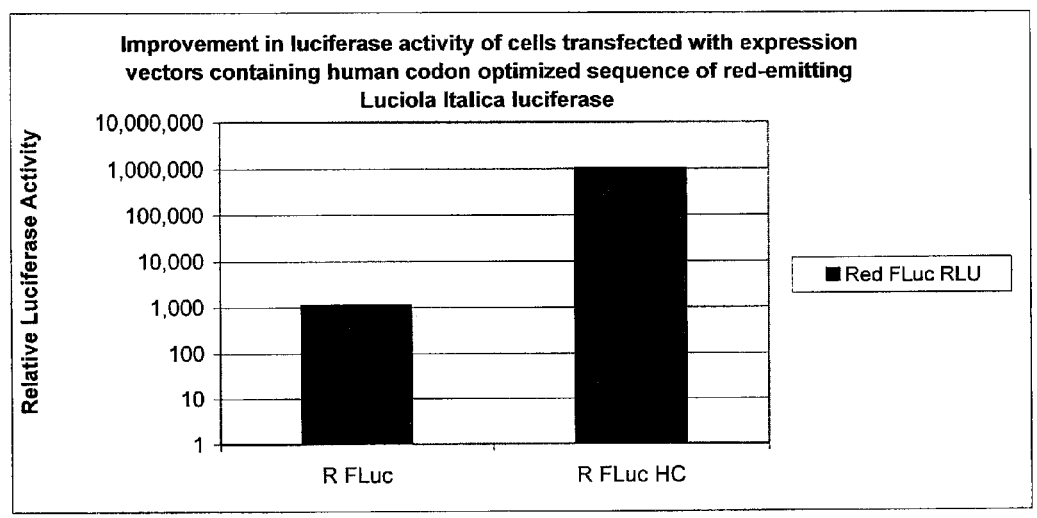
FIG. 8 shows data comparing luciferase activity of human codon optimized and non-human codon optimized red-emitting *L. Italica* luciferase.

In some aspects, the present invention provides a red-emitting firefly luciferase (Red-Fluc) from the Italian firefly *Luciola Italica* (emission max 609 nm) and a green-emitting firefly luciferase (Green-Fluc) from the Italian firefly *Luciola Italica* (emission max 550 nm In further embodiments, the present invention provides human codon optimized sequences of red-emitting *L. Italica* luciferases. Such human codon optimized red-emitting *L. Italica* luciferases show significantly increased activity over wildtype red-emitting *L. Italica* luciferases (see FIG. 8). In still further embodiments, the present invention provides human codon optimized sequences of red-emitting *L. Italica* luciferases according to the sequence provided in FIG. 30 (SEQ ID NO: 3). In still further embodiments, the present invention provides human codon optimized sequences of red-emitting *L. Italica* luciferases encoded by polynucleotides with about 80%-99% sequence identity to SEQ ID NO: 3. In still further embodiments, the present invention provides luciferases that are encoded by polynucleotides with about 80%, 85%, 90%, 95%, 96%, 97%, 98%, and 99% sequence identity to SEQ ID NO: 3.

Figure 10:
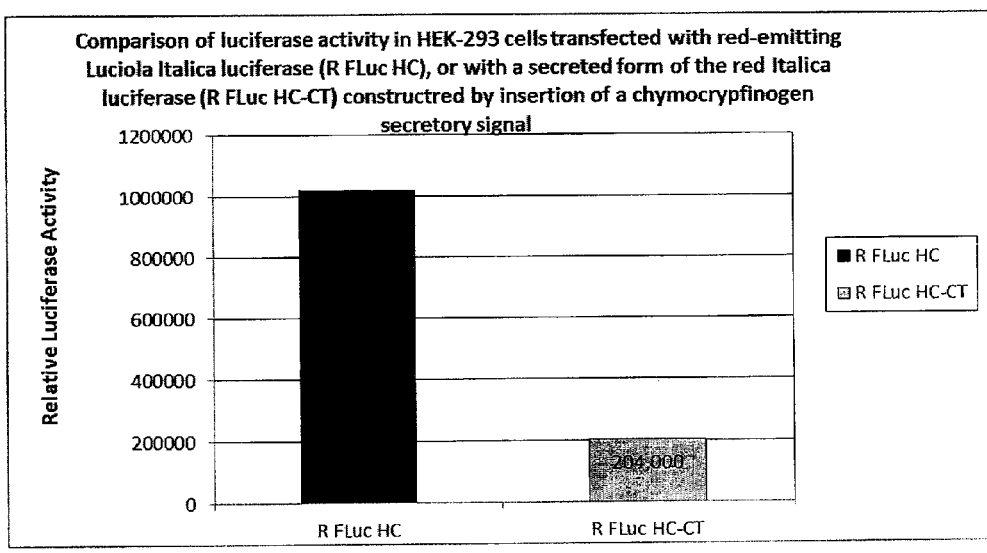
FIG. 10 shows data comparing luciferase activity of intracellular red-emitting *L. Italica* luciferase and secreted red-emitting *L. Italica* luciferase.

In still further embodiments, the present invention provides secreted red-*Italica* luciferases. FIG. 10 shows a comparison of luciferase activity of a human codon optimized red-emitting *L. Italica* luciferases fused to a chymotrypsinogen secretory signal to a non-secreted form of the human codon optimized red-emitting *L. Italica* luciferase. As discussed above, a number of different secretory signals can be used to produce secreted forms of modified luciferases of the invention. However, for red firefly luciferase, not all secretory signals produce a secreted luciferase. For example, popular signal sequences such as the N terminal 16 amino acid sequence of *Gaussia* luciferase and the Interleukin 2 secretory sequence do not successfully produce a secreted form of red emitting firefly luciferase.

Figure 11:
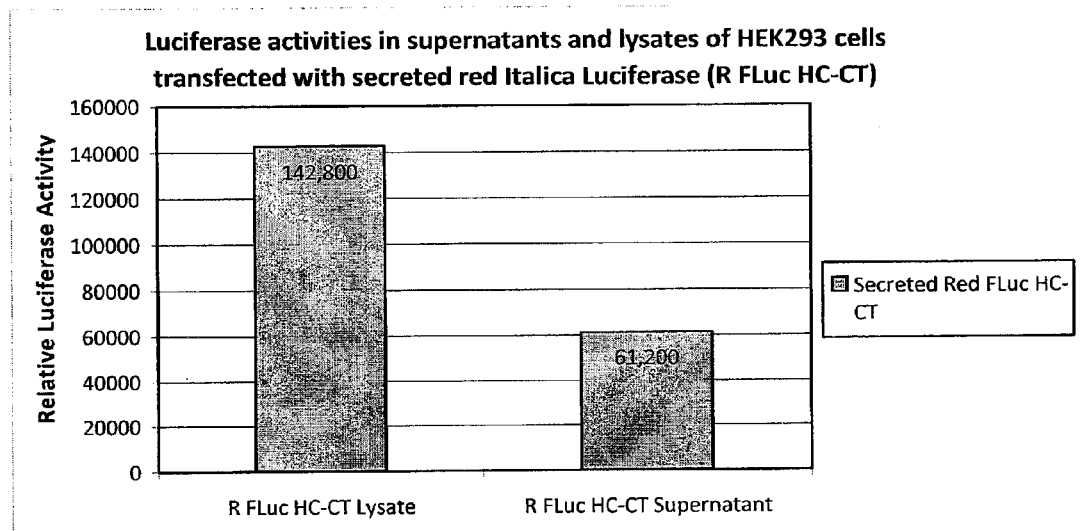
FIG. 11 shows data comparing luciferase activity of secreted red *L. Italica* luciferase in the lysate and the supernatant from HEK293 cells.

Fusing a chymotrypsinogen secretory signal to a human codon optimized red-emitting *L. Italica* luciferases did successfully produce a secreted form of this luciferase. In some embodiments, the present invention provides a red firefly luciferase (also referred to herein as "red-emitting luciferase" and "red-emitting *L. Italica* luciferase") that is modified to include a synthetic secretory signal. In certain embodiments, the modified red firefly luciferase is encoded by the polynucleotide has the sequence provided in FIG. 4 (SEQ ID NO: 2). In still further embodiments, the present invention provides a luciferases encoded by polynucleotides with about 80%-99% sequence identity to SEQ ID NO: 2. In still further embodiments, the present invention provides luciferases that are encoded by polynucleotides with about 80%, 85%, 90%, 95%, 96%, 97%, 98%, and 99% sequence identity to SEQ ID NO: 2. The underlined portion of FIG. 4 is the secretory signal. FIG. 11 shows a comparison of luciferase activities in supernatants and lysates of HEK293 cells transfected with a secreted red *Italica* Luciferase of the invention.

Figure 9:
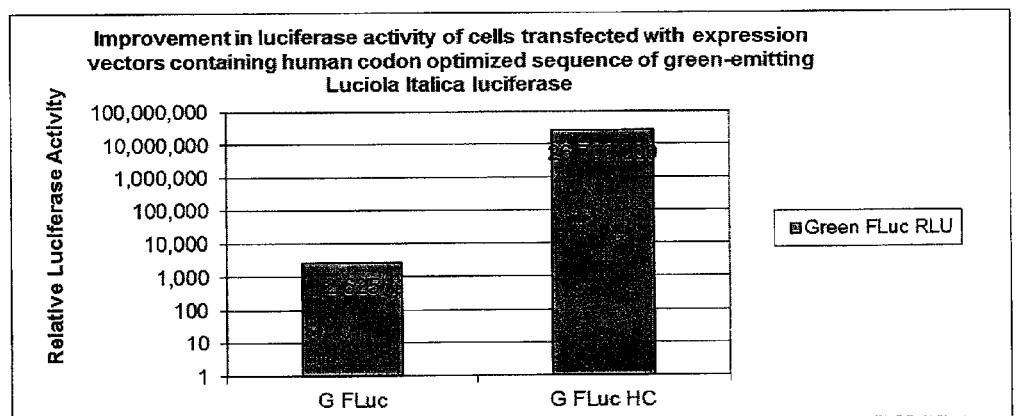
FIG. 9 shows data comparing luciferase activity of human codon optimized and non-human codon optimized green-emitting *L. Italica* luciferase.

In further embodiments, the present invention provides human codon optimized sequences of green-emitting *L. Italica* luciferases. Such human codon optimized green-emitting *L. Italica* luciferases show significantly increased activity over a previously described thermostable mutant of green-emitting *L. Italica* luciferase (B. R. Branchini et al., Analytical Biochemistry, 361 (2): 253-262 (2007)—see FIG. 9). In still further embodiments, the present invention provides human codon optimized sequences of green-emitting *L. Italica* luciferases according to the sequence provided in FIG. 31 (SEQ ID NO: 4). In still further embodiments, the present invention provides human codon optimized sequences of luciferases encoded by polynucleotides with about 80%-99% sequence identity to SEQ ID NO: 4. In still further embodiments, the present invention provides luciferases that are encoded by polynucleotides with about 80%, 85%, 90%, 95%, 96%, 97%, 98%, and 99% sequence identity to SEQ ID NO: 4.

*Renilla* Luciferases of the Invention

In some aspects, the present invention provides a modified efficiently secreted blue-emitting (emission max 480 nm) *Renilla* luciferase (B-Rluc), which more stable than the wildtype *renilla reniformis* luciferase, and a green emitting secreted *Renilla* luciferase (emission max 535 nm) modified to be secreted by fusing a synthetic secretory signal encoding gene sequence in frame with the gene encoding the green emitting modified of *Renilla* luciferase. Mammalian cells transfected with the secreted green *Renilla* luciferase mutant described here show approximately 35-fold higher luciferase activity compared to mammalian cells transfected with the native (human codon optimized) *Renilla* luciferase (see FIG. 7). Further the secreted green *Renilla* luciferase shows excellent stability of the bioluminescent signal (without compromising signal intensity) when assayed using the *Renilla* luciferase assay reagent described in this application (with the stabilizer included, see FIG. 7), thus making it an ideal reporter for High throughput screening applications.

In certain embodiments, the present invention provides a green-emitting *Renilla* luciferase plasmid sequence with the sequence pictured in FIG. 3 (SEQ ID NO: 1).

*Gaussia* Luciferases of the Invention

In some aspects, the present invention provides a *Gaussia* luciferase (emission max 482 nm) that is either native secreted (Gluc) or modified to be expressed intracellularly (Gluc-KDEL). Such *Gaussia* luciferases can be used in single, double and triple reporter assays as discussed in further detail herein in combination with any of the other luciferases discussed herein or known in the art.

Luciferase Assays of the Invention

In certain aspects, the present invention provides compositions that improve stability and signal for assays utilizing wildtype and/or modified luciferases of the present invention.

In some embodiments, sodium chloride is added to improve the stability of luciferase assays of the invention. In such embodiments, a concentration of sodium chloride is utilized that improves the stability of the bioluminescent signal without affecting intensity. In further embodiments, sodium chloride concentrations in the range of about 0.05 M to about 1 M are used to improve stability of luciferase assays of the invention. In still further embodiments, sodium chloride concentrations of about 0.05 to about 0.5, 0.1 to about 0.4, about 0.2 to about 0.3, and about 0.05 to about 0.2M are used in luciferase assays of the invention. In specific embodiments, sodium chloride is added to improve the stability of assays utilizing wildtype and/or modified *Vargula* luciferases.

In further embodiments, certain luciferase substrates are added to luciferase assays to improve the stability of the bioluminescent signal. In such embodiments, the substrate added as a stabilizer may be an additional substrate that is not the substrate upon which the luciferase itself acts. For example, in assays utilizing *Cypridina* luciferase, coelenterazine is added to the assay to stabilize the assay stability. Coelenterazine is an oxidizable luciferin that is easily prone to oxidation but is not a substrate for the *Cypridina* luciferase. As will be appreciated, any luciferase assay described herein can be further modified by adding substrates for other luciferases as a stabilizer.

In some embodiments, the concentration of luciferase substrate is adjusted to improve the magnitude and/or stability of the signal. In further embodiments, low (under 1 μM) concentrations of substrate is used to improve luciferase signals. For example, for *Cypridina* luciferase assays, about 1 to about 25 nM Vargulin are used in assays of the invention. In further embodiments, about 1-100, 5-90, 10-80, 15-70, 20-60, 25-50, and 30-40 nM Vargulin are used in assays of the invention. In further exemplary embodiments, substrates for the luciferase assays described herein (including *Cypridina, Gaussia* and *L. Italica* luciferases) are added in concentrations of from about 1 nM to about 250 μM. In still further embodiments, substrates are added in concentration of about 10 nM-200 μM, 50 nM-150 μM, 100 nm-100 μM, 150 nm-50 μM, 200 nM-25 μM, 300 nM-10 μM, 500 nM-1 μM.

Figure 14:
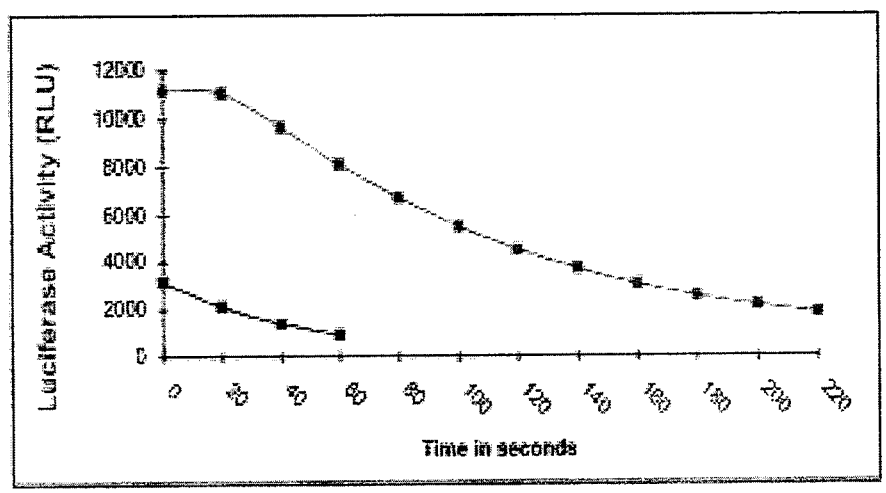
FIG. 14 shows kinetics data of a *Gaussia* luciferase assay using a GAR-1 reagent.

In some embodiments, *Gaussia* luciferases of the invention are used with optimized reagents to produce increased activity. Kinetics of the *Gaussia* luciferase assay using the GAR-1 reagent is shown in FIG. 14. Measurement of the luciferase activity in supernatants of cells (transfected with *Gaussia* luciferase) using GAR-1 reagent from Targeting systems showed increased activity from *Renilla* luciferase assays from another vendor. The data in FIG. 14 is presented as an average of triplicate determinations measured on a Turner TD2020 luminometer. GAR-1 reagent has been described in detail in US Pat Appl Publ 2008074485, which is hereby incorporated by reference in its entirety and in particular for all teachings related to assay reagents for the *Gaussia* luciferase assay.

Figure 12A:
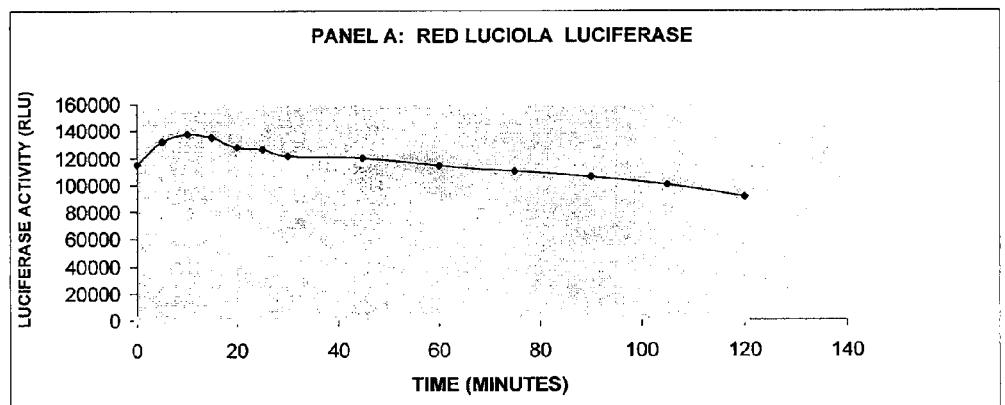
FIG. 12 shows kinetics of luciferase activity in (A) Red *Luciola* luciferase, (B) *Guassia* luciferase, (C) *Cypridina* luciferase, and (D) Green *Renilla* luciferase.
Figure 12B:
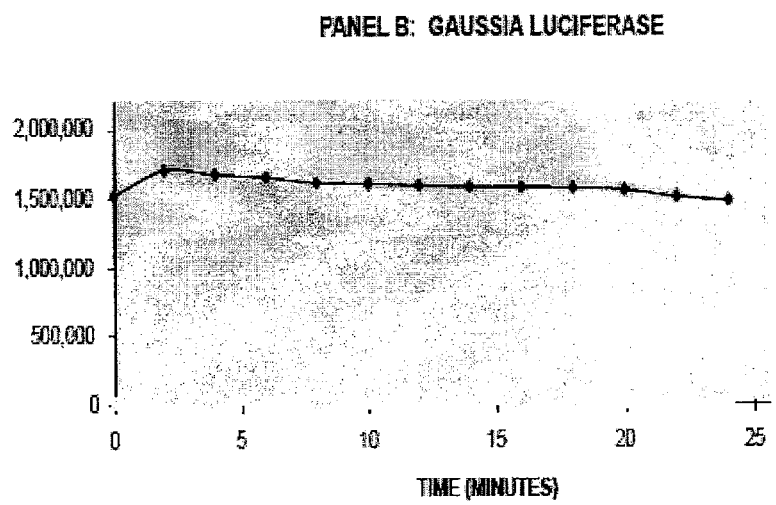
Figure 15A:
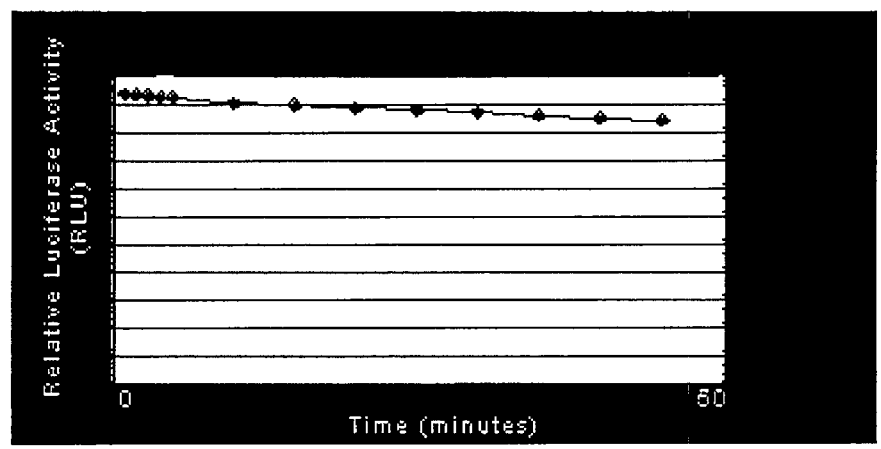
FIG. 15 shows data comparing stabilities of *Gaussia* luciferase assays using the GAR-2 reagent are in the presence of a stabilizer (FIG. 15A) and in the absence of a stabilizer (FIG. 15B).
Figure 15B:
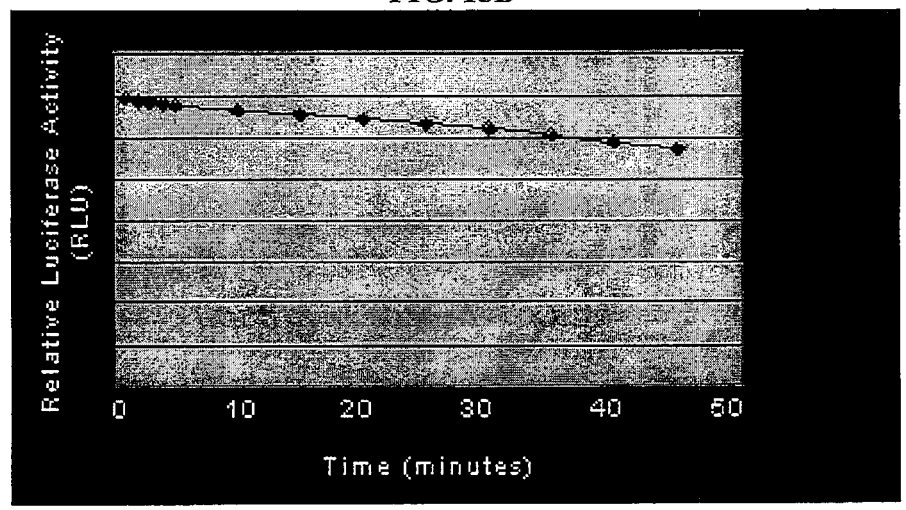

In certain embodiments, *Gaussia* luciferase assays of the invention utilize reagents stabilized with stabilizing agents. In one non-limiting example, the stabilizing agents include NP40 (Sigma) and/or coelenterazine. In certain embodiments, about 5 to about 200 μM coelenterazine is used. In still further embodiments, about 10-150, 20-125, 30-100, 40-75, 50-60 μM coelenterazine is used. In yet further embodiments, about 5, 10, 15, 20, 25, 30, 35, 40, 45, 50, 55, 60, 65, 70, 75, 80, 85, 90, 95, 100 μM coelenterazine is used. Stability of *Gaussia* luciferase assays using the GAR-2 reagent are shown in FIG. 15. Using the GAR-2B version of the *Gaussia* luciferase assay reagent, the bioluminescent signal remains very stable (FIG. 15A) In the absence of the stabilizer, the signal intensity is a little higher initially but decays faster than in the presence of the stabilizer (FIG. 15B). Note that the data presented in FIG. 15A and B is an average of triplicate determinations measured on a Turner TD2020 luminometer. The GAR-2 and GAR-2B reagents are stabilized versions of the GAR-1 reagent discussed in US Pat Appl Publ 2008074485, which is hereby incorporated by reference in its entirety and in particular for all teachings related to reagents for *Gaussia* luciferase assays. The GAR-2 reagent includes the composition GAR-1 with an additional 30 μM coelenterazine. GAR-2B reagent includes the composition GAR-1 with and additional 75 μM coelenterazine. Without being limited by theory, it is possible that the higher (approximately 3-fold) signal intensity seen with the GAR-2B reagent is due to the higher concentration of coelenterazine. FIG. 12B shows the stability of the *Gaussia* luciferase with the GAR-2 reagent including a stabilizer.

Figure 16:
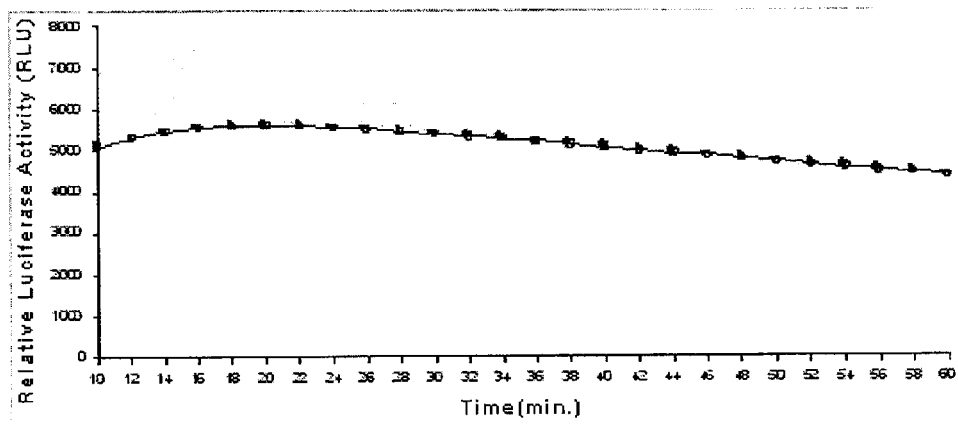
FIG. 16 shows data related to relative luciferase activity of a firefly luciferase assay.

In certain embodiments, stability of firefly luciferase assays is improved using FLAR-1 reagents (Targeting Systems). FIG. 16 shows the results from experiments using the FLAR-1 reagent from Targeting Systems. In the experiments shown in FIG. 16, the FLAR-1 reagent was added to the supernatant cell culture media.

Dual and Triple Luciferase Assays

In some aspects, the present invention provides dual luciferase assays based on spectral resolution of two or more different luciferases. As will be appreciated, these assays can include different wildtype luciferases, different modified luciferases, or a mixture of a wildtype and a modified luciferase. Such assays rely on differences in the emission spectra of the reporters used. In further embodiments, reagents are modified to allow for more efficient multiplexing. For example, when *Gaussia* luciferases are multiplexed with firefly luciferases, EDTA is omitted from the reaction mixture to allow efficient reporter activity.

Figure 13A:
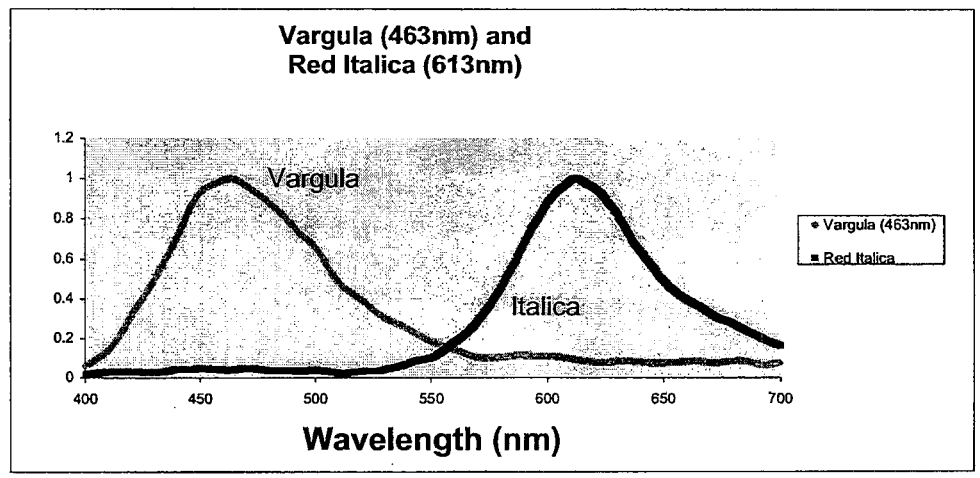
FIG. 13 shows emission spectra from (A) a double reporter assay with *Vargula* and Red *Italica* luciferases and (B) a triple reporter assay with *Vargula*, Green *Renilla* and Red *Italica* Luciferases.

FIG. 13A shows the emission spectra of a dual reporter assay utilizing a *Vargula* and Red *Italica* luciferase of the invention. The luciferases were expressed in samples of transfected cells. The luciferases used in the experiments pictured in FIG. 13A represent a modified red emitting firefly luciferase of the invention that is human codon optimized and intracellular (non-secreted) and a *Cypridina* luciferase of the invention that is from *Cypridina hilgendorfi* modified to be human codon optimized and secreted.

Figure 13B:
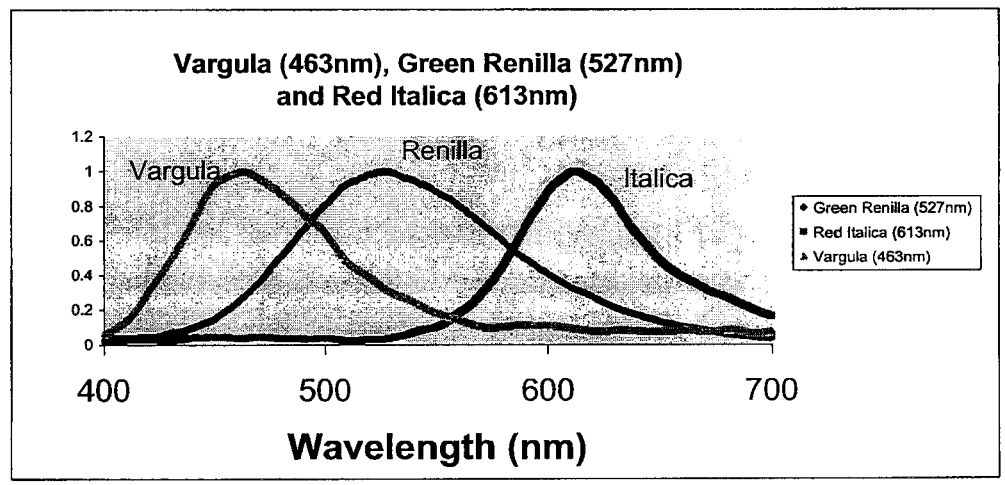

FIG. 13B shows the emission spectra of a triple reporter assay utilizing *Vargula*, Green *Renilla* and Red *Italica* luciferases. These emission spectra were in samples of transfected cell lysates. The *Vargula* and red-emitting firefly luciferases are those as described above for FIG. 13A and the Green *Renilla* luciferase is an improved secreted Green luciferase mutant as described in further detail herein.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

EXAMPLES

Example 1

Transfection of Mammalian Cells with Modified Luciferases

HEK-293 cells were grown in DMEM/10% FBS (fetal bovine serum) and transfected with plasmids expressing either the human codon-optimized or non-human codon optimized forms of the red emitting and green emitting firefly luciferases (from *Luciola Italica*) under control of the CMV promoter. Transfections were performed using the Targefect F-2 reagent (Targeting Systems) using the manufacturers protocols. Forty eight hours post transfection, the cells were lysed using the cell lysis reagent (CLR-1) from Targeting Systems, Santee. 20 µl aliquots of the cell lysate were mixed with 100 µl of the FLAR-1 (firefly luciferase assay reagent from Targeting Systems).

Example 2

*Cypridina* Luciferase Assays with Increased Stability

Compositions were developed for achieving optimal performance of *Cypridina* luciferase assay reagents. These assays had improved stability of the bioluminescent signal without affecting the overall activity of the enzyme.

Vargulin is generally unstable and easily oxidized, making long term storage of this substrate difficult. However, Vargulin stored in an acidic buffer (66 mM monobasic potassium phosphate, pH 6-6.5) and stored at −80° C. was very stable and did not lose activity even when stored for several months. In contrast, Vargulin dissolved in a neutral to basic phosphate buffer (e.g. 200 mM dibasic potassium phosphate (ph 8)) is very unstable and begins to lose activity rapidly within a few hours at room temperature. *Cypridina* luciferase activity was optimal when 200 mM dibasic potassium phosphate was used as the reaction buffer instead of 66 mM monobasic sodium phosphate. Hence 200 mM dibasic potassium phosphate was used as the reaction buffer. Concentrations of be 3-6 nM Vargulin were found to be effective, and these concentrations are much lower than what is generally used in such assays (see for example Wu et al (2007) *Biotechniques*, 42(3):290-292).

The *Cypridina* luciferase assay showed increased stability when sodium chloride was included in the reaction. For example, FIG. 1 shows the relative luciferase stability (RLS) between VLAR-1 (no sodium chloride) and VLAR-2 (VLAR-1+sodium chloride). Sodium chloride clearly stabilized the RLS. For the experiments in FIG. 1, 20 μl of sample was added with 40 μl of VLAR solution for the assay followed by 20 μl of Vargulin substrate.

Figure 5:
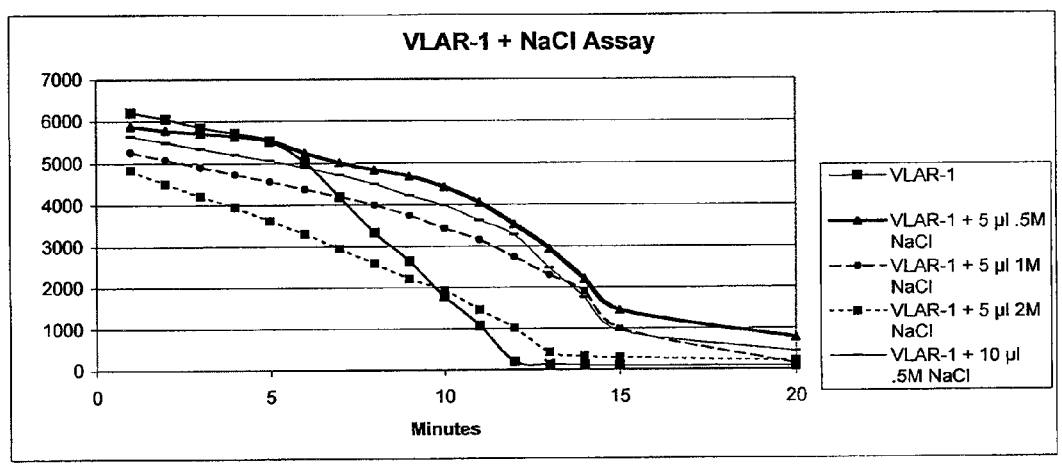
FIG. 5 shows data from a *Cypridina* luciferase assay in varying concentrations of sodium chloride.

FIG. 5 shows a further titration experiment indicating that sodium chloride concentrations of around 0.5M provide increased stability over control reagents with no sodium. Further concentrations that are of use in stabilizing such assays include from about 25 mM to about 750 mM sodium chloride. For experiments in FIG. 5, 5 μl of the indicated concentrations of sodium chloride solutions were added to 35 μl of VLAR buffer (20 mM dibasic potassium phosphate, pH=8.0). The assay was carried out by mixing 20 μl of sample with 40 μl of VLAR buffer (with sodium chloride) and then adding 20 μl of *Cypridina* luciferin.

Further stability of the bioluminescent signal as well as improvement in overall luciferase activity was observed when coelenterazine, another oxidizable luciferin easily prone to oxidation (but not a substrate for *Cypridina* luciferase) m was included in the assay composition. A 15 minute pre-incubtion was found to result in increased stability of the bioluminescent signal using sample volumes between 5 and 20 μl (roughly 40% drop in 26 minutes using an assay volume of 20 μl and 15% drop in 26 minutes using an assay volume of 5 μl—see FIGS. 2A and 2B. A concentration of coelenterazine that worked well to stabilize the reagent was 15 μM. Concentrations in the range of about 10 μM to about 50 μM can also be used. The inclusion of coelenterazine in the composition decreased the background of the assay by more than 10-fold (background reading dropped form 153.6 to 12.4) and also resulted in a 15% increase in the intensity of the bioluminescent signal. Controls in which buffers with identical composition (i.e., inclusion of coelenterazine but omission of *Cypridina* luciferin) showed no activity. Coelenterazine is not a substrate for *Cypridina* luciferase and can be used to safely reduce the background and increase stability when *Cypridina* luciferase is assayed alone or in combination with other luciferases (such as firefly luciferase) which do not use coelenterazine as a substrate. For the experiments shown in FIG. 2, 5 or 20 μl of the sample (media supernatant) was mixed with 40 μl of the VLAR buffer (200 mM dibasic potassium phosphate, 50 mM NaCl). The firefly and *Cypridina* luciferase assay reagents can be mixed into a single solution which can be used to efficiently measure both *Cypridina* luciferase and firefly luciferase activity by spectrally resolving the luciferases using appropriate filers. However, the DTT concentration in the firefly luciferase assay reagent can affect activity in such situations, because the activity of both luciferases is decreased due to interference of DTT (present in low concentration in the firefly assay reagent with the *Cypridina* luciferase assay (there is almost a 10-fold drop in *Cypridina* luciferase activity). However, since the signal intensity of the *Cypridina* luciferase assay is very robust, the signal is still acceptable and improvement in *Cypridina* luciferase activity is observed if the DTT concentration in the firefly luciferase assay reagent is dropped to 2.5 mM (a 3 fold drop in activity of *Cypridina* luciferase is still observed). Single solution based dual assays in which *Cypridina* luciferase is multiplexed with Green emitting *Renilla* luciferase work very well without loss of activity of either *Cypridina* or *renilla* luciferase when the two solutions are mixed.

Example 3

Figure 7:
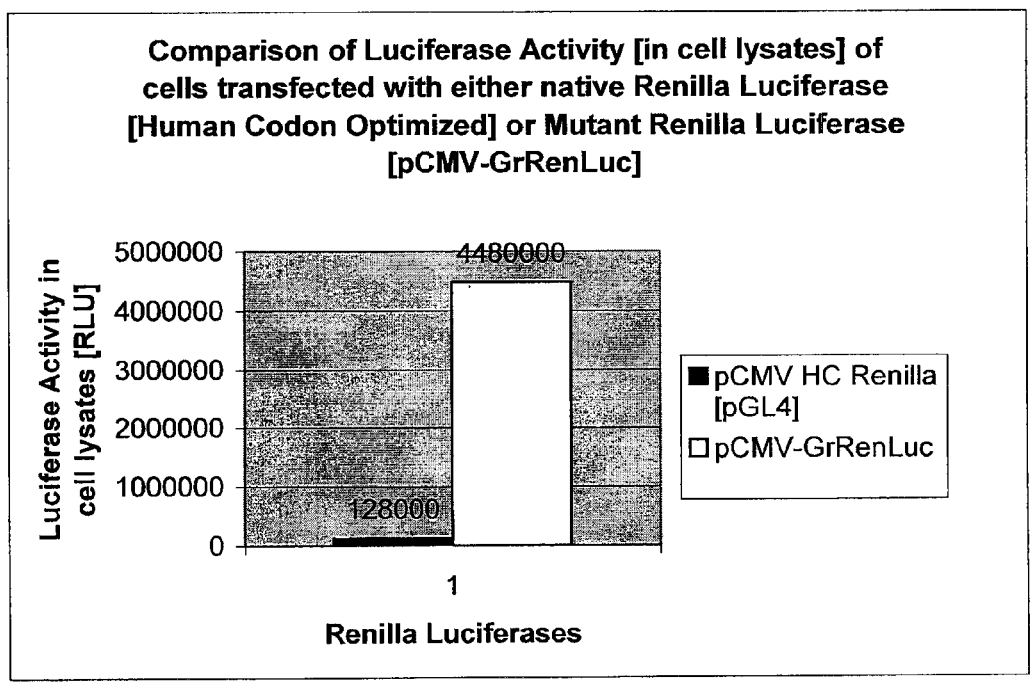
FIG. 7 shows data comparing luciferase activity of native human codon optimized *Renilla* luciferase and a mutant *Renilla* luciferase of the invention.

*Renilla* Luciferase Assays Utilizing Modified *Renilla* Luciferases and Stabilizing Reagents The secreted modified green *Renilla* luciferase of the present invention showed significantly greater activity over wildtype *Renilla* luciferase—see FIG. 7. For the experiments pictured in FIG. 7, HEK 293 cells were transfected with expression vectors expressing either native *Renilla* luciferase or the secreted Green *Renilla* luciferase mutant. Cells were lysed 48 hrs post transfection and assayed for luciferase activity.

Figure 6:
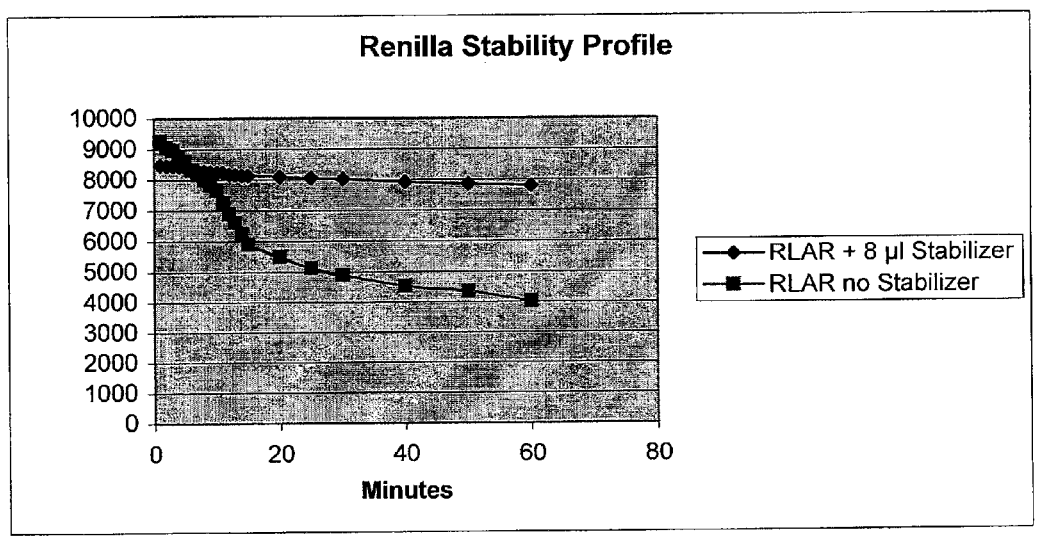
FIG. 6 shows data from a *Renilla* luciferase assay with and without stabilizer (NP40).

Assays with and without stability assay reagents for green *Renilla* luciferase were investigated. FIG. 6 shows that assays conducted with stabilizer showed greater stability than those without. The composition of the *Renilla* luciferase assay reagent (no stabilizer) was: 30 μM coelenterazine, 0.4×PBS (Ca, Mg free), 0.027% NP40. The composition of the *Renilla* luciferase assay reagent (with stabilizer) was: 30 μM coelenterazine, 0.4×PBS (Ca, Mg free), 0.227% NP40. Stabilizer is 2% NP40 (a non-ionic detergent).

Example 4

Kinetics of Different Luciferases

Reactions were set up to measure the kinetics of the luciferase activities of different luciferases in samples of transfected cells. Luciferase activities were assayed using the luciferase assay reagents supplied with the LiveResponse assay kit. These data are shown in FIG. 12A: Red *Luciola* (firefly), luciferase, FIG. 12B *Gaussia Princeps* luciferase (this is FIG. 15C), FIG. 12C: *Cypridina* luciferase, and FIG. 12D: Green *Renilla* luciferase. Data represents mean of triplicate determinations.

Example 5

Comparison of Expression Vectors Expressing Modified *Vargula* Luciferases

Transfection protocols were as follows: HEK-293 cells were grown in DMEM/10% FBS (fetal bovine serum) and transfected with plasmids expressing wither the human codon-optimized to non-human codon optimized forms of native VLuc, HC-VLuc, sequence 1) or modified HC-VLucs under control of the CMV promoter. Transfections were performed using the Targefect F-2 regent (Targeting Systems) using the manufacturers protocols.

Figure 17:
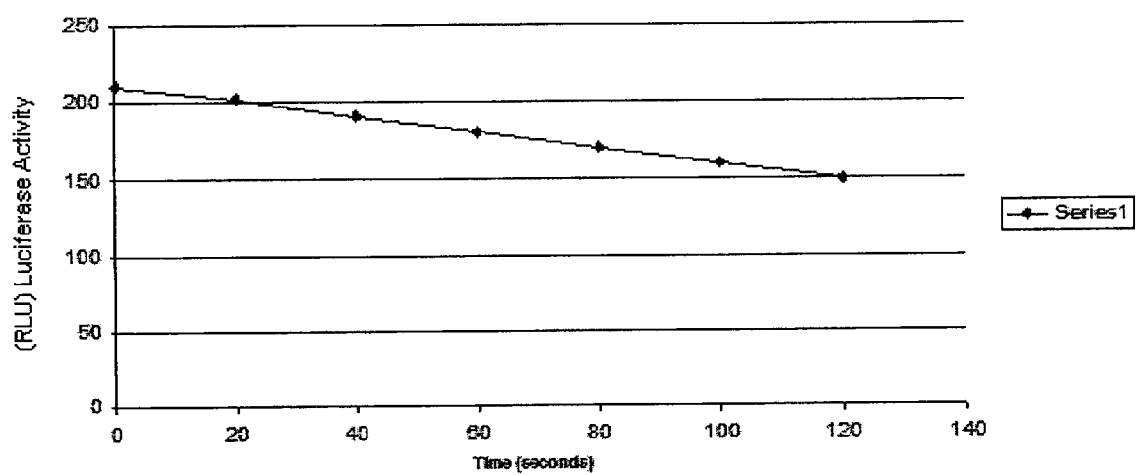
FIG. 17 shows data of relative luciferase activity of a *Cypridina* luciferase assay.

The stability of the bioluminescent signal of *Cypridina* Luciferase assessed using supernatants of HEK293 cells transiently transfected with the pCMV VLuc expression vector is shown in FIG. 17.

Figure 19:
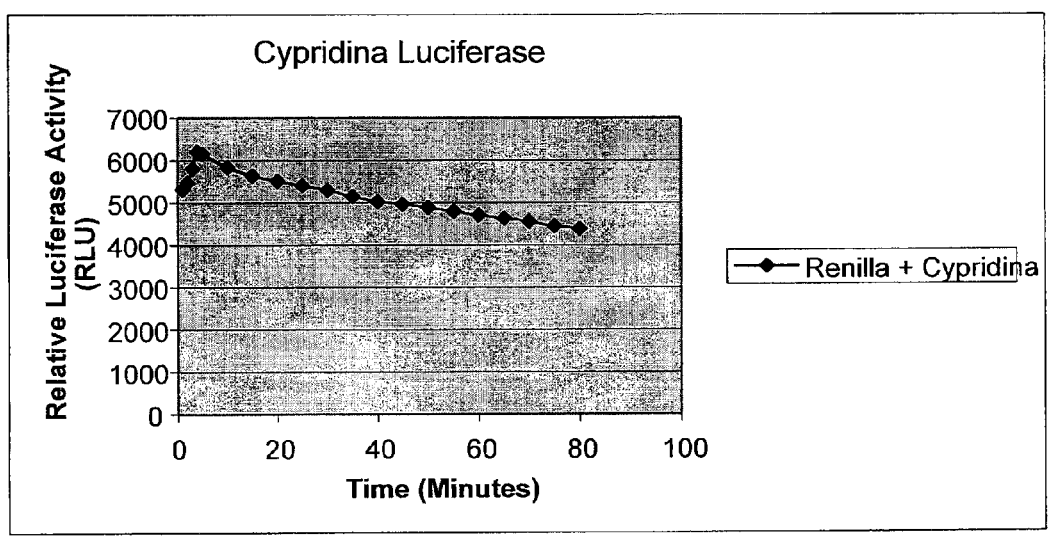
FIG. 19 shows kinetic data for luciferase activity in a *Cypridina* luciferase assay.

In FIG. 19, the stability of the bioluminescent signal of *Cypridina* Luciferase was assessed using supernatants from HEK 293 cells transiently transfected with the pCMV-VLuc expression vector. Samples were assayed using the VLAR-2

(VLAR-1 reagent from Targeting Systems with sodium chloride) of the *Cypridina* luciferase assay reagent.

Human codon optimization of the gene sequence encoding the VLuc led to a 5-fold improvement of luciferase expression in HEK-293 transfected with expression vectors containing the human codon optimized versions of the *vargula* luciferase genes compared to the native sequences (i.e. Non-human codon optimized sequences). Addition of the KDEL sequence at the C-terminal end results in intracellular expression of VLuc.

Example 6

Construction of Blue-Emitting (Blue Shifted) and Green Emitting Mutants of Secreted *Renilla* Luciferase for Use as Secreted Reporters in Single or Multiplexed Luciferase Assays A synthetic signal peptide was deduced by rational design: MLLK VVFA IGCI VVQA (SEQ ID NO: 7). The sequence of this signal peptide was based on rational design using signal sequences from the secretory signals known in the art, including those available at: http://www.unitargeting.com/Resources/Trends07.pdf Blue-Sifted Secreted *Renilla* Luciferase Mutants Secreted mutants were constructed containing signal peptide fused to amino terminal region of the human codon optimized *renilla reniformis* luciferase with the following additional mutations which enable i) efficient refolding after secretion to obtain an active form of the enzyme (Loma Linda paper, cysteine 124 was mutated to alanine) and additional mutations to cause a shift in the emission max of *Renilla* luciferase. MLLK VVFA IGCI VVQA-HCRLuc with following mutations C124A; N53Q; V146M. Emission maxima=475 nm Secreted BLuc Sequence 2: MLLK VVFA IGCI VVQA-HCRLuc with following mutations C124A; N53Q; V146M and the following eight additional mutations A55T, S130A, K136R, A143M, M185V, M253L, S287L. The 8 additional mutations increase intensity of the bioluminescent signal (Emission Maxima 475 nm)

Red Shifted *Renilla* Luciferase Mutants:

Secreted RLuc Sequence 1: MLLK VVFA IGCI VVQA-HCRLuc with following mutations C124A, D162E Secreted RLuc Sequence 2: MLLK VVFA IGCI VVQA-HCRLuc with following mutations C124A; and the following eight additional mutations AI23S/D154M/E155G/D162E/I163L/V185L F262W. Emission Maxima 535 nm Secreted RLuc Sequence 3: MLLK VVFA IGCI VVQA-HCRLuc with following mutations C124A; and the following eight additional mutations AI23S/D154M/E155G/D162E/I163L/V185L. Emission Maxima 535 nm Example 7

Tests for Developing Assays for *Vargula* Luciferase

In some embodiments, different buffer solutions are used to improve assays utilizing wildtype and/or modified luciferases of the invention. In certain embodiments, a 1:1 mixture of 0.1 M Tris HCl and 75 mM sodium phosphate is used as the assay buffer.

Several different parameters were tested to develop an assay for *vargula* luciferase:

Effects of using either an acidic buffer (e.g., potassium phosphate pH 5-6.8), Tris HCl pH 7.4, Tris phosphate buffer pH (8-8.5) as well as varying assay volumes were tested. In general the use of acidic conditions significantly reduced the intensity of the bioluminescent signal (typically 5-10 fold) while increasing the stability somewhat. Using Tris HCL ph 7.4, the activity as the assay buffer resulted in 5-10 fold brighter bioluminescence but the luminescent signal was highly unstable.

Use of a buffer mixture (1:1) of 50 mM Tris HCl, pH 7.4 and 100 mM dibasic sodium phosphate resulted in improved stability of the bioluminescent signal without compromising the intensity of the bioluminescent signal. An interesting finding was that inclusion of 0.2 M NaCl further increased stability of the bioluminescent signal. Lastly the amounts of Vargulin needed for optimal activity using this buffered condition are very low (1-10 nM range) making the assay extremely useful and economical.

Increasing the concentration of Vargulin further did not increase stability of the assay further.

Stock Vargulin substrate solutions stored in an acidic condition pH (5.5-6) were relatively stable over several months when stored at −80° C.

Other parameters tested: Other stabilizers such as DTT (dithiothreitol), detergents like NP-40 or EDTA were unable to increase the intensity of the luminescent signal or improve stability of the assay. EDTA decreased the VLuc activity by at least 5-fold.

Thus one aspect of the invention concerns the following composition and variations thereof: 20 µl of cell supernatant assays with 50 µl of Tris/phosphate buffer, pH 8, 0.2 M NaCl, 10 µl of 5-100 nM vargulin in 66 mM potassium phosphate (monobasic). In certain assays, the effective concentration of vargulin in the assay mix is as low as 20 nM which is approximately 50-fold lower than that reported in the literature (see for example Wu et al (2007) Biotechniques, 42(3):290-292)

Comparison of luciferase activity in cells transfected with *vargula* luciferase with luciferase activity in cells transfected with firefly luciferases from *Photinus pyralis* or *Luciola* Italic showed that *vargula* luciferase was a much more sensitive reporter (10-20 fold improvement in bioluminescent signal compared to firefly luciferase, assay done in HEK-293 cells, all expression vectors were expressed luciferase under control of the CMV promoter). An exemplary assay protocol included: 20 µl aliquots of Cell supernatants (media with 5% serum) were mixed with 100 µl of assay dilution buffer (50 µl of 50 mM TrisHCl, 100 mM dibasic sodium phosphate, pH 8) and 10 µl of vargulin in sodium phosphate buffer pH 6 (final concentration of vargulin in reaction mix 10-25 nM). The sample was mixed well and bioluminescent activity was recorded in a Turner TD2020 luminometer integrated over a 20 sec time interval.

Example 8

Activity in Cell Supernatant and Cell Lysates of Cell Transfected with Either a Plasmid Vector Expressing Secreted *Vargula* Luciferase or an Intracellular Form of *Vargula* Luciferase In cells transfected with the secreted form of modified *vargula* luciferase, 80% of the activity was secreted into the cell supernatant and only 20% is cell-associated.

Figure 18:
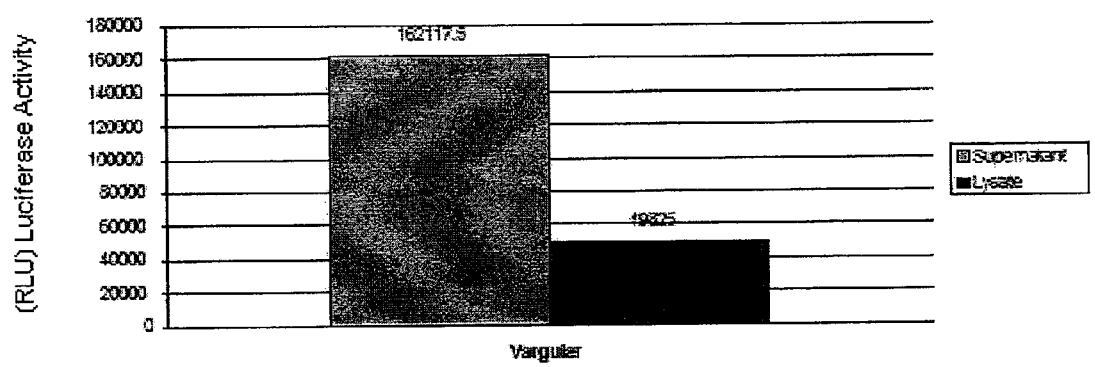
FIG. 18 shows data comparing luciferase activity of a modified *Vargula* luciferase of the invention in the lysate and the supernatant from mammalian cells.

FIG. 18 shows intracellular and secreted *Cypridina* luciferase activity. Luciferase activity in cell supernatants and cell lysates of cells transfected with a plasmid vector expressing secreted *vargula* luciferase. As shown in FIG. 18 cells transfected with the secreted form of modified *vargula* luciferase, 80% of the activity is secreted into the cell supernatant and only 20% is cell-associated.

In cells transfected with *vargula* luciferase modified at the C-terminal end with a KDEL sequence, approximately 95% of the activity was intracellular and 5% is secreted.

Example 8

Development of a Dual Reporter System Based on Blue and Red Shifted Mutants of Secreted *Renilla* Luciferase Secreted mutants: Secreted mutants were constructed containing signal peptide fused to amino terminal region of the human codon optimized *renilla reniformis* luciferase with the following additional mutations which enable i) efficient refolding after secretion to obtain an active form of the enzyme (Cysteine 124 was mutated to alanine) and additional mutations to cause a shift in the emission max of *renilla* luciferase: MLLK VVFA IGCI VVQA-HCRLuc with following mutations: C124A; N53Q; V146M. Emission maxima=475 nm Secreted RLuc Sequence 2: MLLK VVFA IGCI VVQA-HCRLuc with following mutations. C124A; N53Q; V146M and the following eight additional mutations A55T, S130A, K136R, A143M, M185V, M253L, S287L. The 8 additional mutations increase intensity of the bioluminescent signal. Emission Maxima 475 nm RED SHIFTED *RENILLA* LUCIFERASE MUTANTS: Secreted RLuc Sequence 1: MLLK VVFA IGCI VVQA-HCRLuc with following mutations: C124A, D162E Secreted RLuc Sequence 3: MLLK VVFA IGCI VVQA-HCRLuc with following mutations: C124A; and the following eight additional mutations AI23S/D154M/E155G/D162E/I163L/V185L F262W. Emission Maxima 535 nm Secreted RLuc Sequence 4: MLLK VVFA IGCI VVQA-HCRLuc with following mutations: C124A; and the following eight additional mutations. A123S/D154M/E155G/D162E/I163L/V185L. Emission Maxima 535 nm A single solution dual luciferase assay based on secreted *renilla* luciferase blue emitting (emission max at 475 nm) and green emitting mutants (emission max at 535 nm).

The mutations in the above sequences lead to the efficient expression of secreted *renilla* luciferase in the transfected cells. The two luciferases can therefore be used in combination as a dual reporter system and the luciferase activity of each luciferase in the transfected cells can be resolved by using appropriate filters. The reagent compositions for *renilla* luciferase assay reagents are described Walia, US Pat Appl Publ 2008074485, entitled Enhancing a Luminescent Signal, which is incorporated herein by reference in its entirety and in particular for all teachings related to *Renilla* luciferase assay reagents.

Example 9

Development of a Triple Reporter System Based on Red and Green Emitting Firefly Luciferases and *Gaussia* Luciferase/*Renilla* Luciferase Composition of the *Gaussia* luciferase assay reagent (GAR-1) has been described in detail in a US Pat Appl Publ 2008074485, which is hereby incorporated by reference in its entirety and in particular for all teachings related to assay reagents for the *Gaussia* luciferase assay. An assay reagent useful for simultaneous measurement of all there reporters in a single solution was designed by omitting EDTA from the composition of the *Gaussia* luciferase assay reagent and then including all the ingredients necessary for assay of firefly luciferase in a single composition. The rationale behind this is that the EDTA interferes with the firefly luciferase assay (magnesium is an important co-factor for firefly luciferase and EDTA chelates magnesium). The ingredients required for Firefly luciferase assay included in the assay composition were as follows—ATP, DTT. Firefly luciferin, magnesium sulfate, magnesium bromide (helps increase brightness of luminescent signal) and phosphate buffer.

The composition of the single solution for a triple reporter assay for measuring *Gaussia* luciferase or *Renilla* luciferase in combination with red and green emitting firefly luciferase is as follows:

0.1×PBS. 5.4 ml of 5% NP40 diluted to 1000 ml and add the following:

To 800 ml of the above solution add the following:
Tricine 3.227 g (20 mM)
1M Magnesium sulfate 0.7H2O 2.51 ml (2.67 mM
Magnesium bromide 0.6 H2) (1.07 mM)—add 2.14 ml of 500 mM stock solution
25 mM OTT (3.86 g)
530 µM ATP (2.72 g)
CoA (0.18 g)—optional
Adjust with sodium phosphate to pH 7.8
Add 940 µM D-Luciferin (fee acid)—253.81 mg
CDTA-0.8289 g
940 µM D-luciferin (free acid)—253.81 mg
CDTA-0.8289 g
0.8M Tris (0.02 M EDTA)—43.53 ml
Add GAR reagent without EDTA to a total volume of 1 liter
Dilute 100× coelenterazine substrate with the above solution to 1× just before use. Use normal 3 mg/5 ml absolute alcohol acidified with 30 µl of 2N HCl)

NOTE: This assay reagent does not contain enough cell lysis reagents. Hence cells have to be first lysed using 1× Cell Lysis Buffer (compatible with use of all luciferases (prepared from 5× stock solution described below:

Dilute the 5× Cell lysis buffer described below with water to 1× concentration and add to washed cells and shake at 400 rpm for 20 mins to lyse cells.

Composition of 5× Cell Lysis Buffer:
For 1 liter of Buffer
5 ml NP 40 (undiluted)
25 ml Tris HCl ph 8
1.45 g NaCl
50 ml glycerol Example 10

Development of a Single Solution Triple Luciferase Reporter Assay Based on Red and Green Emitting Firefly Luciferases and *Vargula* Luciferase A *vargula* luciferase-based triple reporter system was prepared by first preparing the *vargula* luciferase assay reagent (VLAR-1) and mixing it in a 1:1 ratio with the firely luciferase assay reagent (FLAR-T) to give the triple assay reagent TVLAR-1.

Assay protocol: To 20 µl of cell lysate add 100 µl of the TVLAR-1 reagent and read in the Victor luminometer (Perkin Elmer) or Varian (Promega) using appropriate filters.

Preparation of VLAR-1 Reagent:
Composition of the *Vargula* Luciferase Assay reagent is described below
500 ML OF 0.1 M TRIS HCL PH 8
500 ML of dibasic sodium phosphate 200 mM
200 ml of 5 nM Vargulin in 66 mM potassium phosphate pH 5.5 pH of final solution is 8-8.5
Composition of the FLAR-T Reagent
SOLUTION A: 0.1×PBS. 5.4 ml of 5% NP40 diluted to 1000 ml and add the following:
To 800 ml of the above solution add the following:
Tricine 3.227 g (20 mM)
1M Magnesium sulfate. 7H2O 2.51 ml (2.67 mM)
Magnesium bromide (0.6 H2) (1.07 mM)—add 2.14 ml of 500 mM stock solution
5 mM DTT (in some embodiments, any range between 5 mM and 30 mM can be used, including 5, 10, 15, 20, 25, 26, 27, 28, 29, and 30 mM)
530 µM ATP (2.72 g)
CoA (0.18 g)—optionally omitted
Adjust with sodium phosphate to pH 7.8
Add 940 µM D-Luciferin (free acid)—253.81 mg
CDTA-0.8289 g
940 µM D-luciferin (free acid)—253.81 mg
CDTA-0.8289 g
941 µM D-luciferin (free acid)–253.81 mg
CDTA-0.8289 g
0.8M Tris (0.02 M EDTA)—43.53 ml
ADD SOLUTION A to a total volume of 1 liter NOTE: This assay reagent does not contain enough cell lysis reagents for effective lysis. Hence cells should first be lysed, e.g., using 1× Cell Lys is Buffer (compatible with use of all luciferases (prepared from 1× stock solution described below: Dilute the 5× Cell lysis buffer described below with water to 1× concentration and add to washed cells and shake at 400 rpm for 20 mins to lyse cells.

Composition of 5× cell lysis buffer:
For 1 liter of Buffer
5 ml NP 40 (undiluted)
25 ml Tris HCl ph 8
1.45 o NaCl
50 ml glycerol Composition of Firefly luciferase assay reagent (for use of firefly luciferase as a single reporter gene).
20 mM tricine (179.2 3.55 g)
MgCo3 1.07 mM 0.55 g
Magnesium sulfate 2.7 mM (277 ml)
0.1 mM EDTA
20 mM DTT (4.25 g)
530 µM ATP (3 g)
CoA (0.198 g)
Add disodium phosphate 25 g to ph 7.8
Add 793 ml water before pH
470 µM D Luciferin free acid 279.2 mg
5×CCLR 307 ml
Composition of 5×CCLR:
0.8 M Tris 0.02 M EDTA pH 8-156 ml
Glycerol 500 ml
Triton X100 50 ml
CDTA-7.5 m moles (2.7 g)
DTT 10 mM 1.542 g total vol 1 liter.

Example 11

Figure 12C:
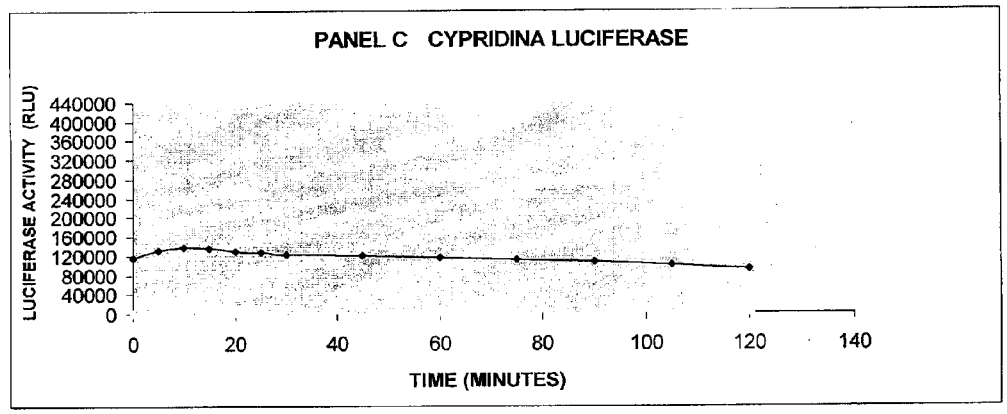
Figure 12D:
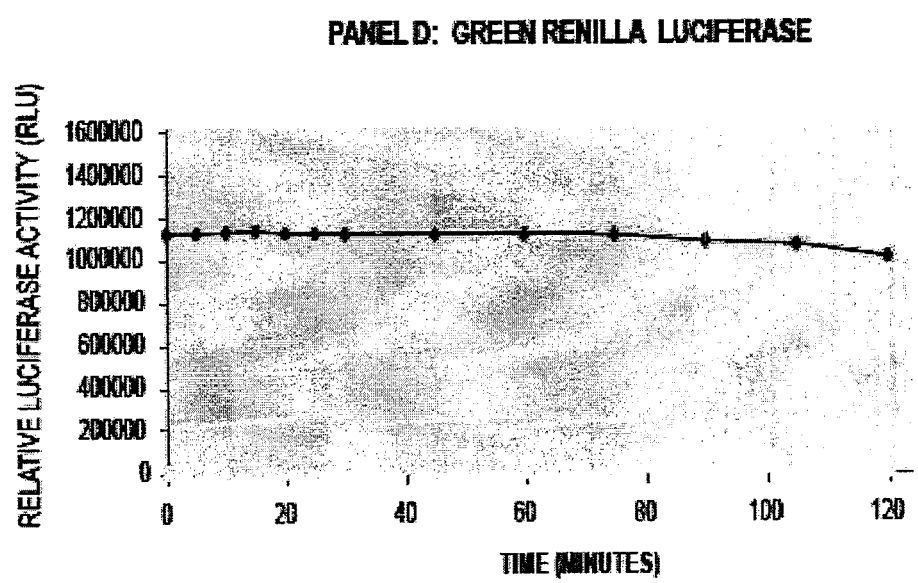
Figure 20A:
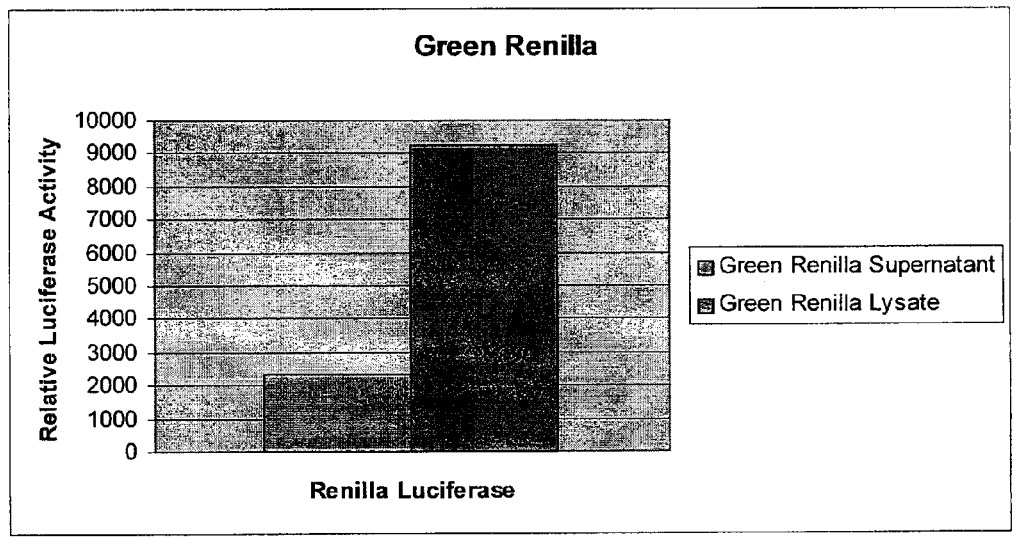
FIG. 20 shows data comparing relative luciferase activity of Green *Renilla* luciferase in the absence (top panel) and presence (bottom) of a stabilizer.
Figure 20B:
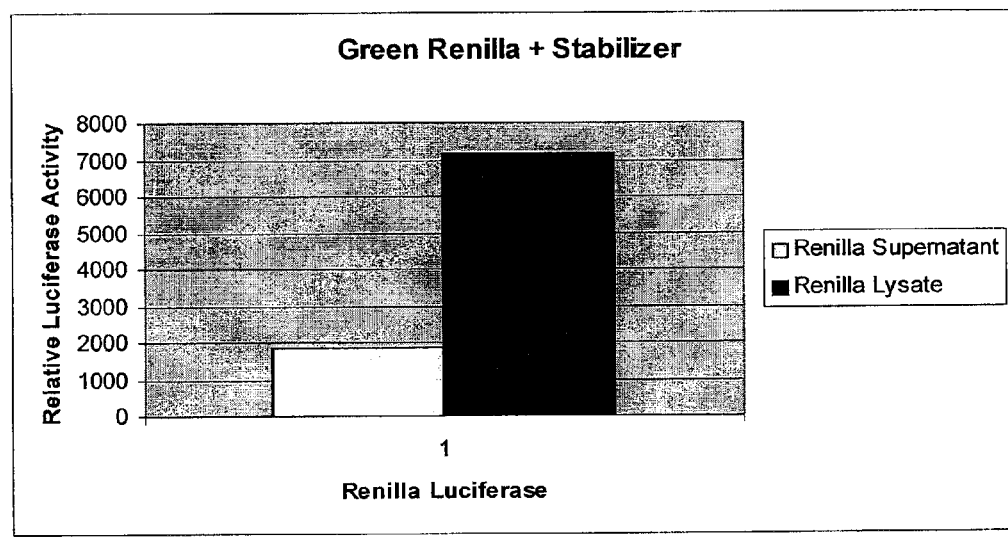
Figure 21:
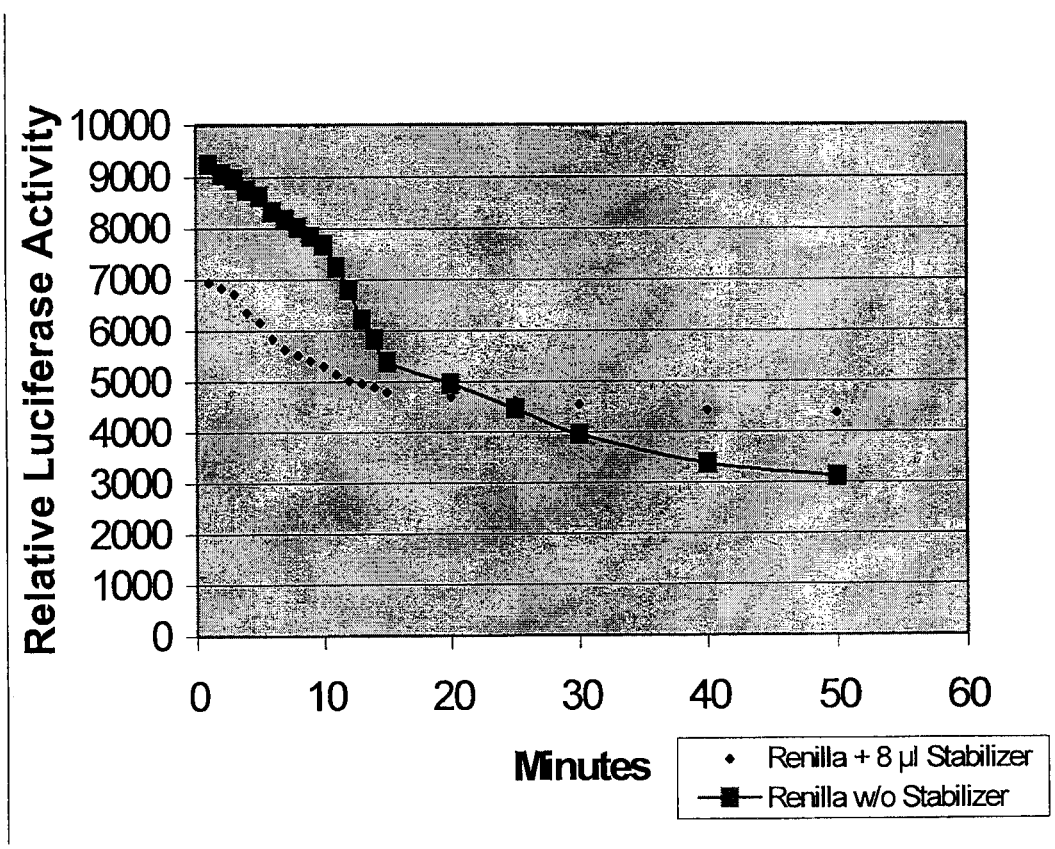
FIG. 21 shows data from a firefly luciferase assay in the presence (square) and absence (diamonds) of a stabilizer.

Development of a Single Solution Triple Luciferase Reporter Assay Based on Red and Green Emitting Firefly Luciferases and *Vargula* Luciferase Addition of stabilizer does not significantly affect (i.e, there is very little decrease in signal intensity) intensity of bioluminescent signal of *Renilla* luciferase in supernatants and lysates. FIG. 20 (top panel) shows a *Renilla* assay performed with 10 µl of *Renilla* Lysate and 20 µl of *Renilla* Supernatant. Assay went as follows: 20 or 10 µl of sample (Supernatant or Lysate), 50 µl of RLAR-1 reagent (Targeting Systems). FIG. 20 (bottom panel) shows *Renilla* Assay was performed using the same volumes of lysate and supernatant as in the experiments in the top panel. Assay protocol was as follows: 10 or 20 µl of lysate or supernatant depending on the assay, 50 µl of the RLAR-1 reagent and an additional 8 µl of RLAR stabilizer for an increased stability profile for a time course reading. The stabilizer lowered the initial RLU reading (decreased from approximately 9000 to approximately 7000 rlu) but showed a much higher level of stability when observed over 30 minutes to 1 hour (FIG. 12C). The RLAR-1 reagent is useful for high throughput screening (HTS) applications in which a large number of samples need to be assayed. In the absence of the stabilizer, the signal intensity decays faster than in the presence of stabilizer (FIG. 21). Note: Data presented is average of triplicate determinations measured on a Turner TD2020 luminometer. In FIG. 21, a time course was taken using the standard protocol of 10 µl lysate, 50 µl of RLAR reagent without stabilizer indicating drop in *Renilla* luciferase activity.

Figure 22:
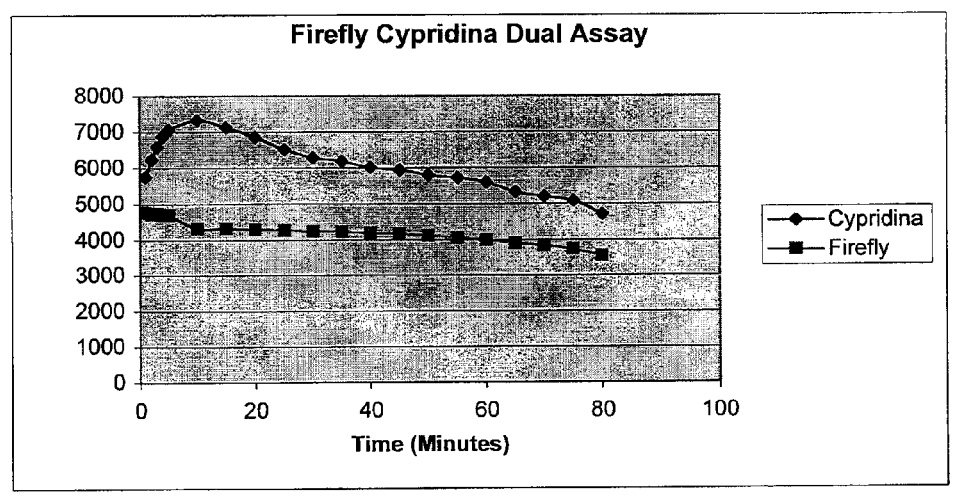
FIG. 22 shows data from a dual assay of the invention utilizing firefly and *Cypridina* luciferases.

FIG. 22 shows the stability of the bioluminescent signal of *Cypridina* luciferase and firefly luciferase using the DLAR-3 reagent. This reagent is useful for HTS applications involving both *Cypridina* luciferase and the red-emitting *Luciola* luciferase. Note: Data presented is average of triplicate determinations measured on a Turner TD2020 luminometer. The DLAR-3 reagent (Targeting Systems) is a dual assay reagent based on secreted *Cypridina* luciferase and a secreted or intracellular red-emitting firefly luciferase.

Figure 28:
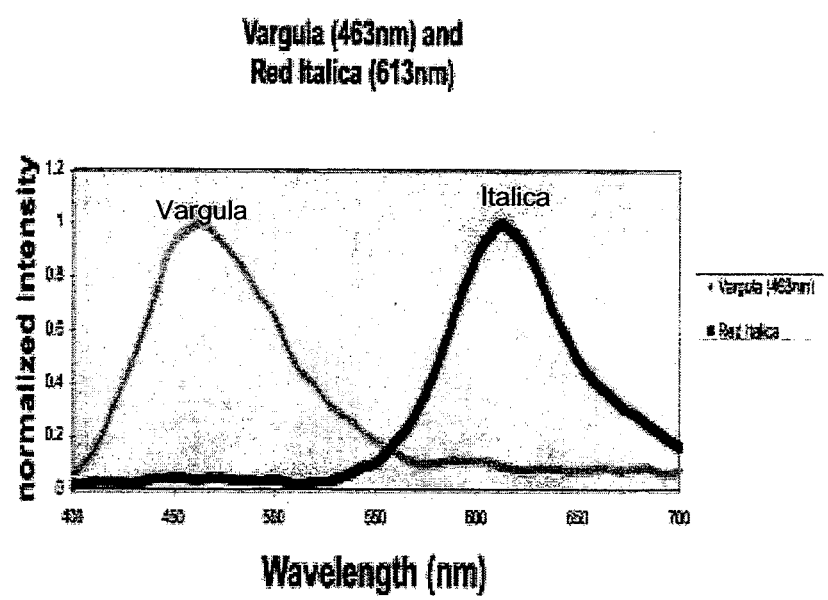
FIG. 28 shows emission spectra from a dual assay of the invention utilizing *Vargula* and Red *Italica* luciferases.
Figure 29A:
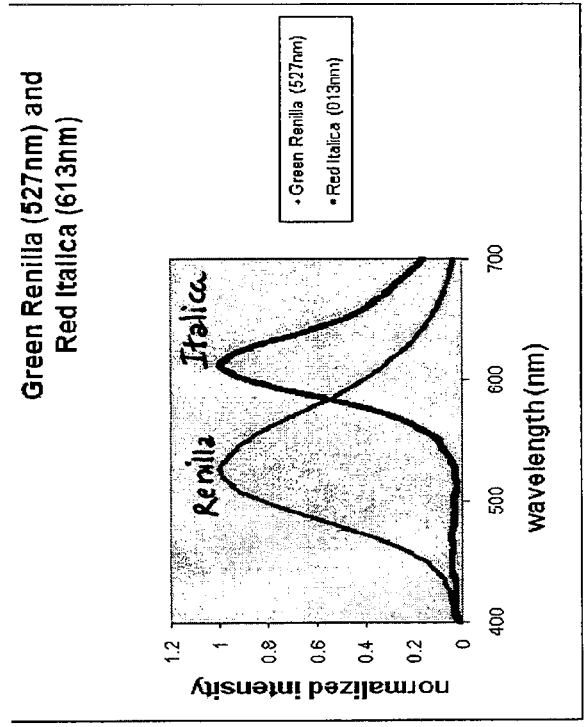
FIG. 29 shows emission spectra emission spectra from a dual assay of the invention utilizing (A) *Gaussia* and Red *Italica* luciferases and (B) Green *Renilla* and Red *Italica* luciferases.
Figure 29B:
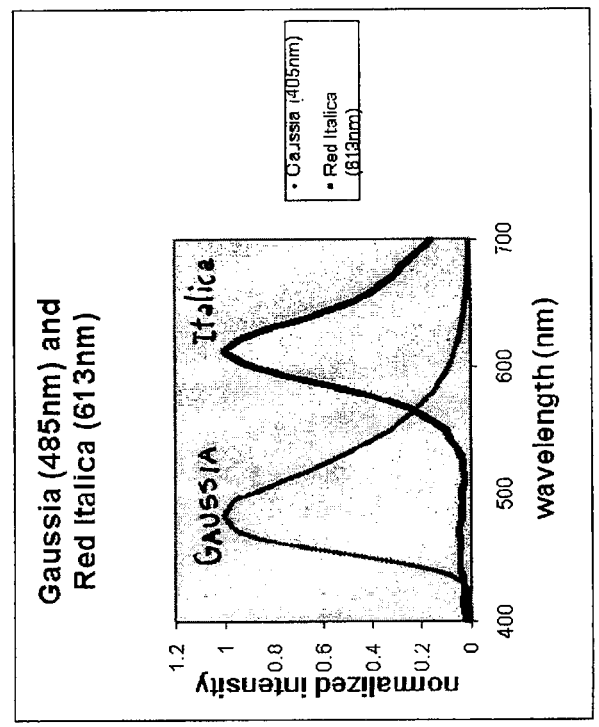

FIG. 28 shows emission spectra of *Cypridina* and Firefly luciferases in samples of transfected cells (lysates or supernatants). The emission spectra were recorded on a Fluorolog-3 spectrofluorometer (Horiba Scientific, Japan) using a liquid nitrogen cooled CCD. The luciferases were assayed by mixing 200 ul of the sample with the appropriate luciferase assay reagent to obtain spectral profiles. Emission max of *Cypridina* Luciferase is 463 nm; Red *Italica* 617 nm.

Example 12

Figure 23A:
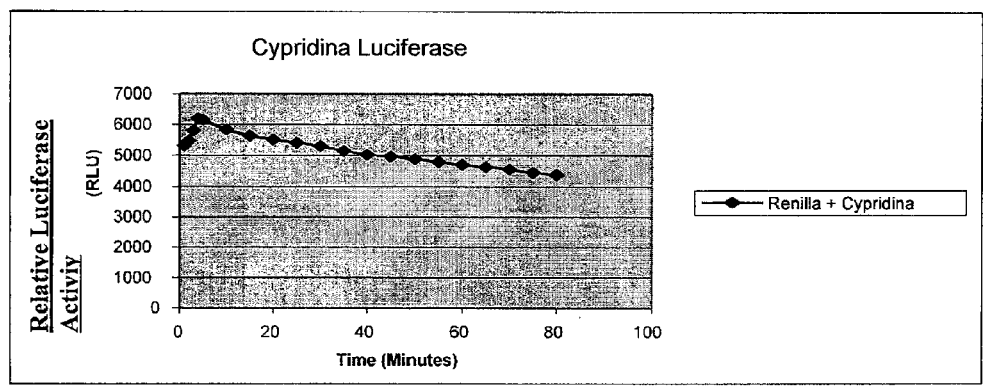
FIG. 23 shows data from a dual assay of the invention utilizing *Cypridina* (Panel A) and *Renilla* (Panel B) luciferases.
Figure 23B:
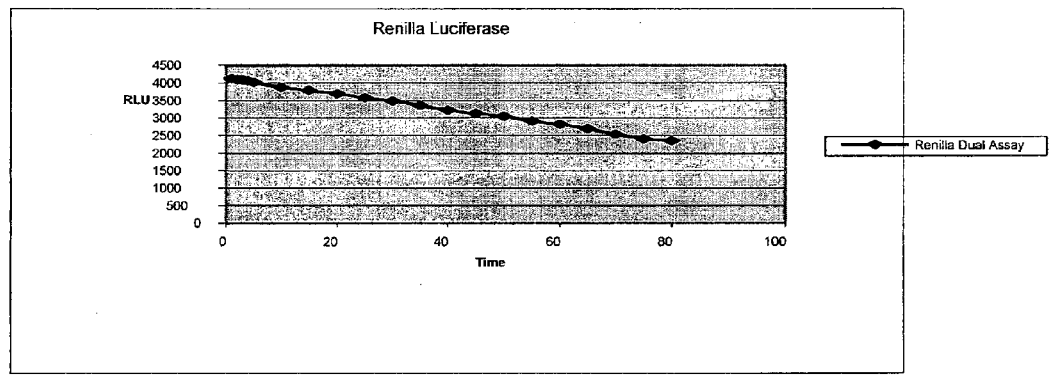

Double and Triple Luciferase Reporter Assays Based on *Renilla* Luciferase, Firefly Luciferase and *Vargula* Luciferase Kinetics of luciferase activity of different luciferase reporters using luciferase assay reagents in the DLAR-5 system are shown in FIG. 23. Reactions were set up to measure the kinetics of the luciferase activities of different luciferases in samples of transfected cells. Luciferase activities were assayed using the DLAR-5 luciferase assay reagents. The decay of the *renilla* luciferase signal shown in Panel B above can be greatly minimized (ie the bioluminescent signal can be rendered much more stable by addition of a *Renilla* luciferase stabilizer to the DLAR-5 buffer.

Figure 24:
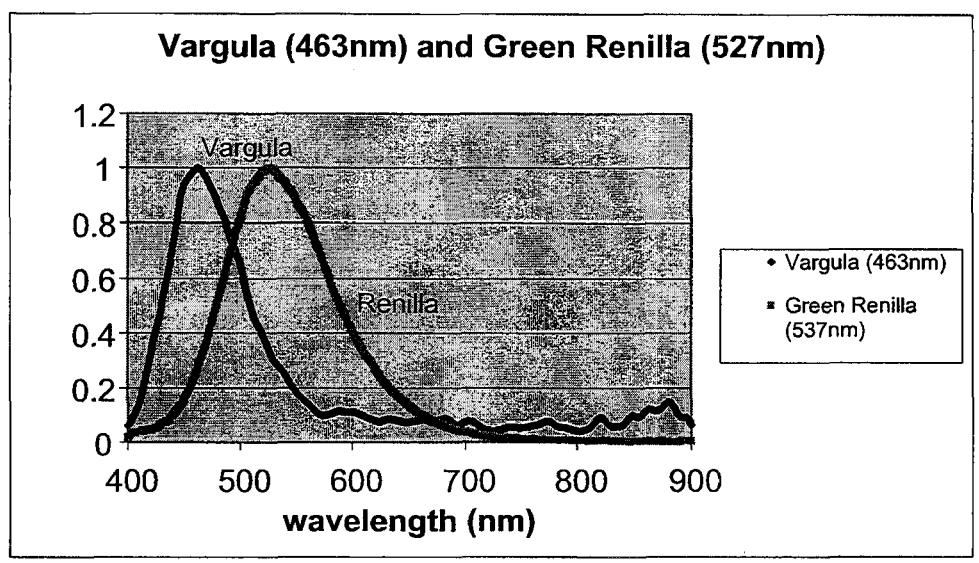
FIG. 24 shows emission spectra from a dual assay of the invention utilizing *Vargula* and Green *Renilla* luciferases.

FIG. 24 shows Emission spectra of different luciferases in samples of transfected cell lysates. Relative luciferase activities of *Cypridina*, Green *Renilla* luciferases were assayed with the appropriate luciferase assay reagent to obtain spectral profiles. The emission max of *Vargula* luciferase is 463 nm; Green *Renilla* luciferase is 527 nm. Note that the data presented in this application is performed with the green-emitting mutant that emits at 527 to 530 nm (this is the variation in emission maxima seen and the luciferase is different in sequence, properties and emission maximum from the 535 nm emitting intracellular green emitting *Renilla* luciferase mutant described in US Patent Publication No.

20090136998, which is hereby incorporated by reference in its entirety and in particular for all teachings related to Green *Renilla* luciferase.

Figure 25:
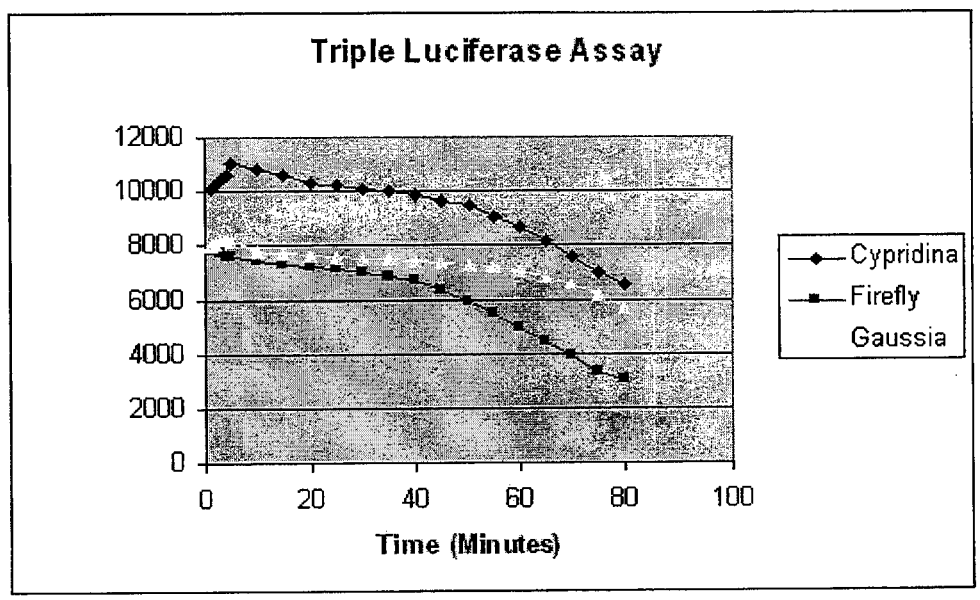
FIG. 25 shows data from a triple assay of the invention utilizing *Cypridina*, firefly and *Gaussia* luciferases.

FIG. 25 shows kinetics of luciferase activity of different luciferase reporters using luciferase assay reagents in the triple reporter system. Reactions were set up to measure the kinetics of the luciferase activities of different luciferases in samples of transfected cells. Luciferase activities were measured using the TLAR luciferase assay reagents (Targeting Systems).

Figure 26:
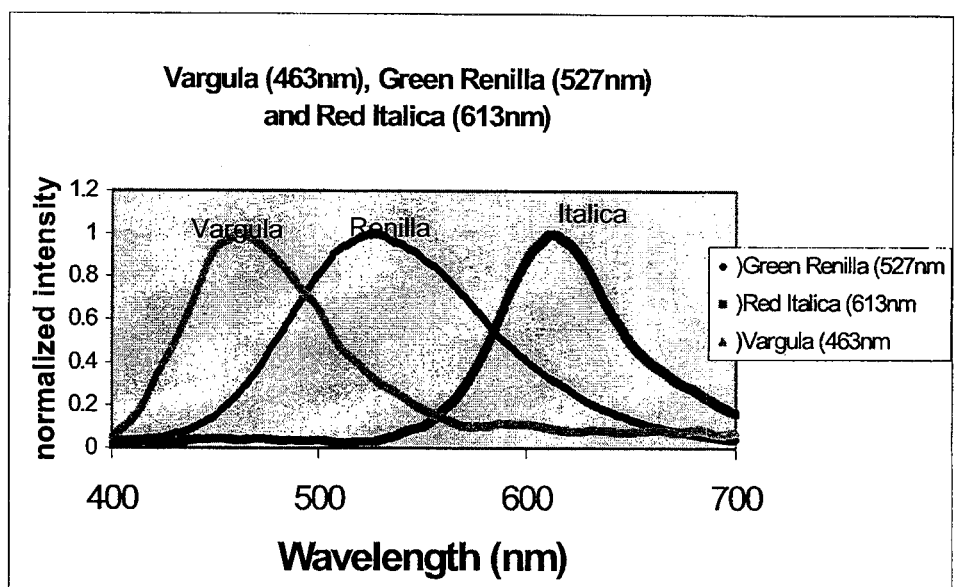
FIG. 26 shows emission spectra from a triple assay of the invention utilizing *Cypridina*, Green *Renilla* and Red *Italica* luciferases.

FIG. 26 shows emission spectra of different luciferases in samples of transfected cell lysates. Relative luciferase activities of *Cypridina*, *Renilla* and Red *Luciola Italia* luciferases were assayed with the appropriate luciferase assay reagent to obtain spectral profiles. The emission max of *Vargula* luciferase is 463 nm; Green *Renilla* luciferase is 527 nm and Red *Luciola Italia* luciferase is 617 nm.

The present invention also provides a single solution-based triple luciferase reporter assay involving *Cypridina* luciferase multiplexed with Green-emitting *Renilla* luciferase and Red-emitting Firefly luciferase. This assay is compatible with high throughput applications. This assay is also optionally in a format where the three luciferases can be assayed separately using three different assay reagents

What is claimed is:

1. A multiplexed luciferase assay composition comprising: multiple luciferase reporters, wherein at least two of the luciferase reporters are selected from the group consisting of a firefly luciferase, a *Renilla* luciferase, a *Gaussia* luciferase and a *Cypridina* (*Vargula*) luciferase, and wherein the different luciferase reporters emit at different wavelengths and/or utilize different substrates, and wherein the firefly luciferase is a red-emitting human codon optimized luciferase encoded by SEQ ID NO:3 with an emission maximum of approximately 617 nm; or wherein the firefly luciferase is a green-emitting human codon optimized luciferase encoded by SEQ ID NO:4 with an emission maximum of approximately 550 nm; or wherein the *Renilla* luciferase comprises A55T, S130A, K136R, A143M, M185V, M253L, and S287L mutations or AI23S, D154M, E155G, D162E, I163L, and V185L mutations compared to wildtype *Renilla* luciferase; or wherein the *Vargula* luciferase is encoded by SEQ ID NO: 6; and wherein at least one of the luciferase reporters comprises a secretory signal, wherein the secretory signal is peptide sequence of SEQ ID NO: 7.

* * * * *